(12) United States Patent
Harris et al.

(10) Patent No.: US 12,042,342 B2
(45) Date of Patent: Jul. 23, 2024

(54) STABILIZER FOR SURGICAL SHAFTS OR CANNULAS

(71) Applicant: Cilag GmbH International, Zug (CH)

(72) Inventors: Demetrius N. Harris, Cincinnati, OH (US); Mark S. Zeiner, Mason, OH (US); Joseph Isosaki, Cincinnati, OH (US); David C. Perdue, Cincinnati, OH (US); Nicholas M. Morgan, West Chester, OH (US); Joshua P. Morgan, Benton, KY (US)

(73) Assignee: Cilag GmbH International, Zug (CH)

( * ) Notice: Subject to any disclaimer, the term of this patent is extended or adjusted under 35 U.S.C. 154(b) by 498 days.

(21) Appl. No.: 17/213,518

(22) Filed: Mar. 26, 2021

(65) Prior Publication Data
US 2021/0338371 A1 Nov. 4, 2021

Related U.S. Application Data

(60) Provisional application No. 63/018,664, filed on May 1, 2020.

(51) Int. Cl.
*A61B 90/50* (2016.01)
*A61B 17/34* (2006.01)

(52) U.S. Cl.
CPC .......... *A61B 90/50* (2016.02); *A61B 17/3423* (2013.01); *A61B 2017/348* (2013.01)

(58) Field of Classification Search
CPC ................. A61B 90/50; A61B 17/3423; A61B 2017/348; A61B 17/3403; A61B 17/3421;
(Continued)

(56) References Cited

U.S. PATENT DOCUMENTS 2,811,042 A * 10/1957 Kenyon ................. G01C 21/18
74/5.22
4,699,616 A 10/1987 Nowak et al.
(Continued)

FOREIGN PATENT DOCUMENTS

| AU | 702882 B2 | 3/1993 |
| CN | 106344126 B | 2/2019 |

(Continued)

OTHER PUBLICATIONS

International Search Report and Written Opinion dated Jul. 22, 2021, for International Application No. PCT/EP2021/061421, 15 pages.

(Continued)

*Primary Examiner* — Tan-Uyen T Ho
*Assistant Examiner* — Bridget E. Rabaglia
(74) *Attorney, Agent, or Firm* — Frost Brown Todd LLP

(57) ABSTRACT

A gyroscopic stabilizer configured to stabilize a surgical instrument relative to a patient includes a frame having a central axis and a hub configured to releasably couple with the surgical instrument. A first gyroscope assembly is coupled with a first frame portion and a second gyroscope assembly is coupled with a second frame portion. Each gyroscope assembly includes a gimbal pivotably coupled with the respective frame portion about a precession axis, a motor, and a rotor rotatably coupled with the motor about a spin axis perpendicular to the respective precession axis. Each gyroscope assembly is operable generate a torque in a torque plane that contains the respective spin axis and the respective precession axis. The torques are configured to resist rotation of the gyroscopic stabilizer relative to the patient about respective device axes that are perpendicular to the central axis and to one another.

20 Claims, 34 Drawing Sheets

(58) Field of Classification Search
CPC .......... A61B 2034/2048; A61B 17/34; A61M 25/00; A61M 25/0097; A61M 25/01
See application file for complete search history.

(56) References Cited

U.S. PATENT DOCUMENTS

| | | |
|---|---|---|
| 5,147,316 A | 9/1992 | Castillenti |
| 5,215,531 A | 6/1993 | Maxson et al. |
| 5,256,147 A | 10/1993 | Vidal et al. |
| 5,263,939 A | 11/1993 | Wortrich |
| 5,267,970 A | 12/1993 | Chin et al. |
| 5,364,372 A | 11/1994 | Danks et al. |
| 5,792,135 A | 8/1998 | Madhani et al. |
| 5,800,451 A | 9/1998 | Buess et al. |
| 5,817,061 A | 10/1998 | Goodwin et al. |
| 5,833,666 A | 11/1998 | Davis et al. |
| 6,638,265 B1 | 10/2003 | Ternamian |
| 7,981,092 B2 | 7/2011 | Duke |
| 8,105,239 B2 | 1/2012 | Specht |
| 8,226,553 B2 | 7/2012 | Shelton, IV et al. |
| 8,251,900 B2 | 8/2012 | Ortiz et al. |
| 8,479,969 B2 | 7/2013 | Shelton, IV |
| 8,568,362 B2 | 10/2013 | Moreno, Jr. et al. |
| 8,573,465 B2 | 11/2013 | Shelton, IV |
| 8,579,807 B2 | 11/2013 | Moreno, Jr. et al. |
| 8,636,686 B2 | 1/2014 | Minnelli et al. |
| 8,690,831 B2 | 4/2014 | Duke |
| 8,783,541 B2 | 7/2014 | Shelton, IV et al. |
| 8,800,838 B2 | 8/2014 | Shelton, IV |
| 10,327,809 B2 | 6/2019 | Buyda et al. |
| 10,792,069 B2 | 10/2020 | Hall et al. |
| 10,820,924 B2 | 11/2020 | Hall et al. |
| 2009/0182282 A1 | 7/2009 | Okihisa et al. |
| 2010/0010449 A1 | 1/2010 | Leibowitz et al. |
| 2013/0060084 A1 | 3/2013 | Fouts et al. |
| 2014/0066953 A1 | 3/2014 | Keating et al. |
| 2016/0015423 A1 | 1/2016 | Ravikumar et al. |
| 2017/0172589 A1 | 6/2017 | Peters et al. |
| 2018/0199959 A1 | 7/2018 | Lee |
| 2018/0206883 A1 | 7/2018 | McIntyre et al. |
| 2019/0000496 A1 | 1/2019 | Shelton, IV et al. |
| 2019/0380742 A1 | 12/2019 | Hall et al. |
| 2021/0338269 A1 | 11/2021 | Scott et al. |
| 2021/0338272 A1 | 11/2021 | Muthuchidambaram et al. |
| 2021/0338273 A1 | 11/2021 | Vijayachandran et al. |
| 2021/0338274 A1 | 11/2021 | Scott et al. |
| 2021/0338275 A1 | 11/2021 | Vijayachandran |
| 2021/0338276 A1 | 11/2021 | Scott |
| 2021/0338278 A1 | 11/2021 | Scott et al. |
| 2021/0338281 A1 | 11/2021 | Mozloom, Jr. et al. |
| 2021/0338282 A1 | 11/2021 | Vijayachandran |
| 2021/0338283 A1 | 11/2021 | McLain |

FOREIGN PATENT DOCUMENTS

| | | |
|---|---|---|
| DE | 202007001745 U1 | 4/2007 |
| EP | 2174602 A1 | 4/2010 |
| WO | WO 1999/052457 A1 | 10/1999 |
| WO | WO 2014/137530 A1 | 9/2014 |
| WO | WO 2015/049391 A1 | 4/2015 |
| WO | WO 2017/132004 A1 | 8/2017 |
| WO | WO 2020/040649 A1 | 2/2020 |

OTHER PUBLICATIONS

International Search Report and Written Opinion dated Aug. 3, 2021, for International Application No. PCT/EP2021/061428, 15 pages.
International Search Report and Written Opinion dated Jul. 16, 2021, for International Application No. PCT/EP2021/061442, 13 pages.
International Search Report and Written Opinion dated Jul. 8, 2021, for International Application No. PCT/EP2021/061447, 15 pages.
International Search Report and Written Opinion dated Jul. 27, 2021, for International Application No. PCT/EP2021/061456, 14 pages.
International Search Report and Written Opinion dated Jul. 13, 2021, for International Application No. PCT/EP2021/061459, 16 pages.
International Search Report and Written Opinion dated Jul. 20, 2021, for International Application No. PCT/EP2021/061466, 17 pages.
International Search Report and Written Opinion dated Jul. 15, 2021, for International Application No. PCT/EP2021/061468, 16 pages.
Veem Gyro White Paper 1403: How Gyros Create Stabilizing Torque; http://veemgyro.com/wp-content/uploads/2015/11/White_Paper_1403-How_Gyros_Create_Stabilizing-Torque.pdf. Accessed on Feb. 17, 2022.
International Search Report and Written Opinion dated Jul. 30, 2021 for Application No. PCT/EP2021/061425, 12 pgs.

* cited by examiner

STABILIZER FOR SURGICAL SHAFTS OR CANNULAS

PRIORITY

This application claims the benefit of U.S. Prov. App. No. 63/018,664, entitled "Stabilizer for Surgical Shafts or Cannulas," filed May 1, 2020, the disclosure of which is incorporated by reference herein.

BACKGROUND

Some surgical procedures may require a clinician to access a surgical site via the abdominal cavity of a patient. To gain such access, an opening is first formed through the abdominal wall tissue overlying the abdominal cavity. In some surgical procedures (referred to as "laparoscopic" or "endoscopic" surgeries), a relatively small opening is made through the abdominal wall tissue, and the surgical site is then accessed with elongate instruments inserted through an access device generally referred to as a "trocar" positioned within the opening. Traditional trocars generally include a cannula assembly and an obturator that is removably received within a working channel of the cannula assembly. In use, the obturator is mated with the cannula assembly, and the combined structure (i.e., the trocar) is directed by a clinician downwardly through the abdominal wall of the patient such that the distal ends of the obturator and the cannula assembly extend into the abdominal cavity. The clinician then withdraws the obturator from the cannula assembly so that surgical instruments may be directed downwardly through the working channel of the cannula assembly to access the surgical site.

Merely exemplary versions of trocars, components thereof, and other varieties of surgical access devices are disclosed in U.S. Pat. No. 7,981,092, entitled "Vibratory Trocar," issued Jul. 19, 2011; U.S. Pat. No. 8,226,553, entitled "Access Device with Insert," issued on Jul. 24, 2012; U.S. Pat. No. 8,251,900, entitled "Surgical Access Devices and Methods Providing Seal Movement in Predefined Paths," issued on Aug. 28, 2012; U.S. Pat. No. 8,579,807, entitled "Absorbing Fluids in a Surgical Access Device," issued on Nov. 12, 2013; U.S. Pat. No. 8,568,362, entitled "Surgical Access Device with Sorbents," issued on Oct. 29, 2013; U.S. Pat. No. 8,636,686, entitled "Surgical Access Device," issued on Jan. 28, 2014; U.S. Pat. No. 8,690,831, entitled "Gas Jet Fluid Removal in a Trocar," issued on Apr. 8, 2014; and U.S. Pat. Pub. No. 2019/0000496, entitled "Method of Suturing a Trocar Path Incision," published Jan. 3, 2019. The disclosure of each of the above-cited U.S. Patents and Publications is incorporated by reference herein.

While various kinds of surgical instruments, including surgical access devices and end effectors, and other associated components have been made and used, it is believed that no one prior to the inventor(s) has made or used the invention described in the appended claims.

BRIEF DESCRIPTION OF THE DRAWINGS

The accompanying drawings, which are incorporated in and constitute a part of this specification, illustrate embodiments of the invention, and, together with the general description of the invention given above, and the detailed description of the embodiments given below, serve to explain the principles of the present invention.

Figure 1:
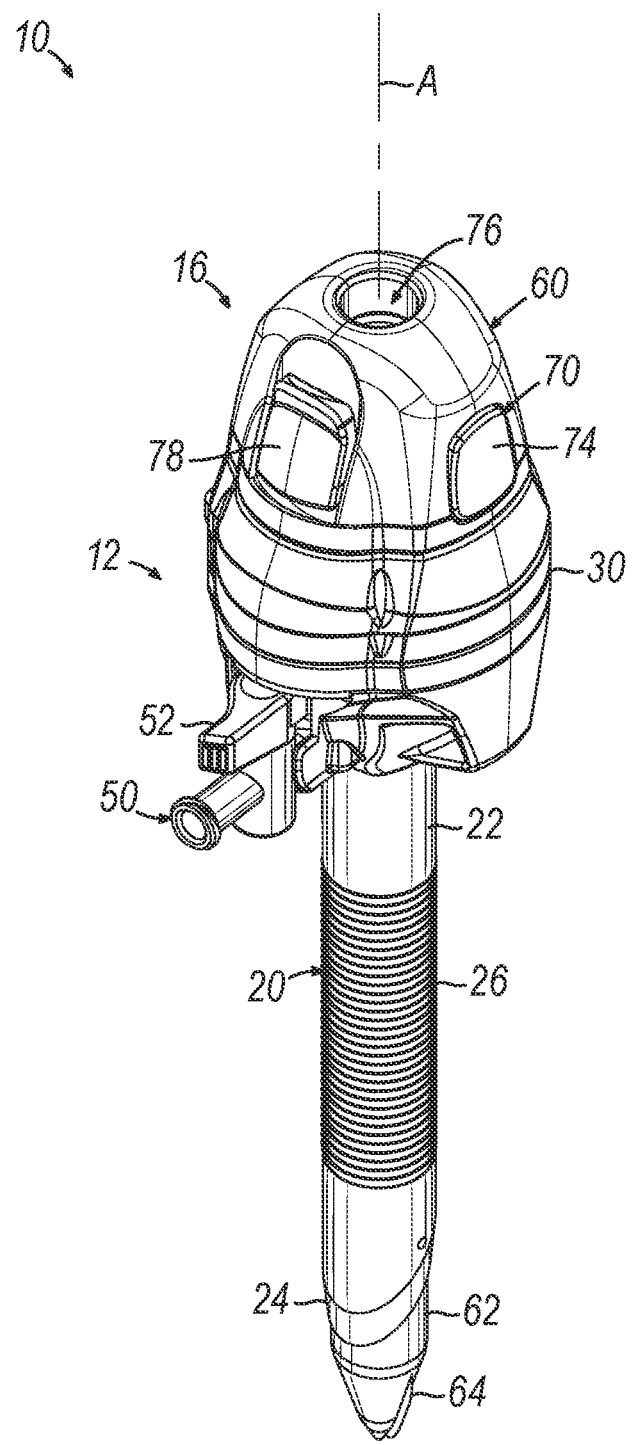
FIG. 1 depicts a perspective view of an exemplary trocar having a cannula assembly and an obturator shown in an assembled state.

The drawings are not intended to be limiting in any way, and it is contemplated that various embodiments of the invention may be carried out in a variety of other ways, including those not necessarily depicted in the drawings. The accompanying drawings incorporated in and forming a part of the specification illustrate several aspects of the present invention, and together with the description serve to explain the principles of the invention; it being understood, however, that this invention is not limited to the precise arrangements shown.

DETAILED DESCRIPTION

The following description of certain examples of the invention should not be used to limit the scope of the present invention. Other examples, features, aspects, embodiments, and advantages of the invention will become apparent to those skilled in the art from the following description, which is by way of illustration, one of the best modes contemplated for carrying out the invention. As will be realized, the invention is capable of other different and obvious aspects, all without departing from the invention. Accordingly, the drawings and descriptions should be regarded as illustrative in nature and not restrictive.

For clarity of disclosure, the terms "proximal" and "distal" are defined herein relative to a surgeon, or other operator, grasping a surgical device. The term "proximal" refers to the position of an element arranged closer to the surgeon, and the term "distal" refers to the position of an element arranged further away from the surgeon. Moreover, to the extent that spatial terms such as "top," "bottom," "upper," "lower," "vertical," "horizontal," or the like are used herein with reference to the drawings, it will be appreciated that such terms are used for exemplary description purposes only and are not intended to be limiting or absolute. In that regard, it will be understood that surgical instruments such as those disclosed herein may be used in a variety of orientations and positions not limited to those shown and described herein.

Furthermore, the terms "about," "approximately," and the like as used herein in connection with any numerical values or ranges of values are intended to encompass the exact value(s) referenced as well as a suitable tolerance that enables the referenced feature or combination of features to function for the intended purpose(s) described herein.

I. Exemplary Single-Use and Reusable Trocars

FIGS. 1-5 depict exemplary surgical access devices in the form of a single-use first trocar (10) and a reusable second trocar (110), each configured to provide surgical site access in a laparoscopic surgical procedure. Each trocar (10, 110) includes a cannula assembly (12, 112) having a working channel (14, 114), and an obturator (16, 116) configured to be removably inserted coaxially into the working channel (14, 114) so that the assembled trocar (10, 110) may be directed distally through the abdominal wall of a patient and into the abdominal cavity, for example as described below in connection with FIGS. 3A-3D.

A. Exemplary Single-Use Trocar

Figure 2:
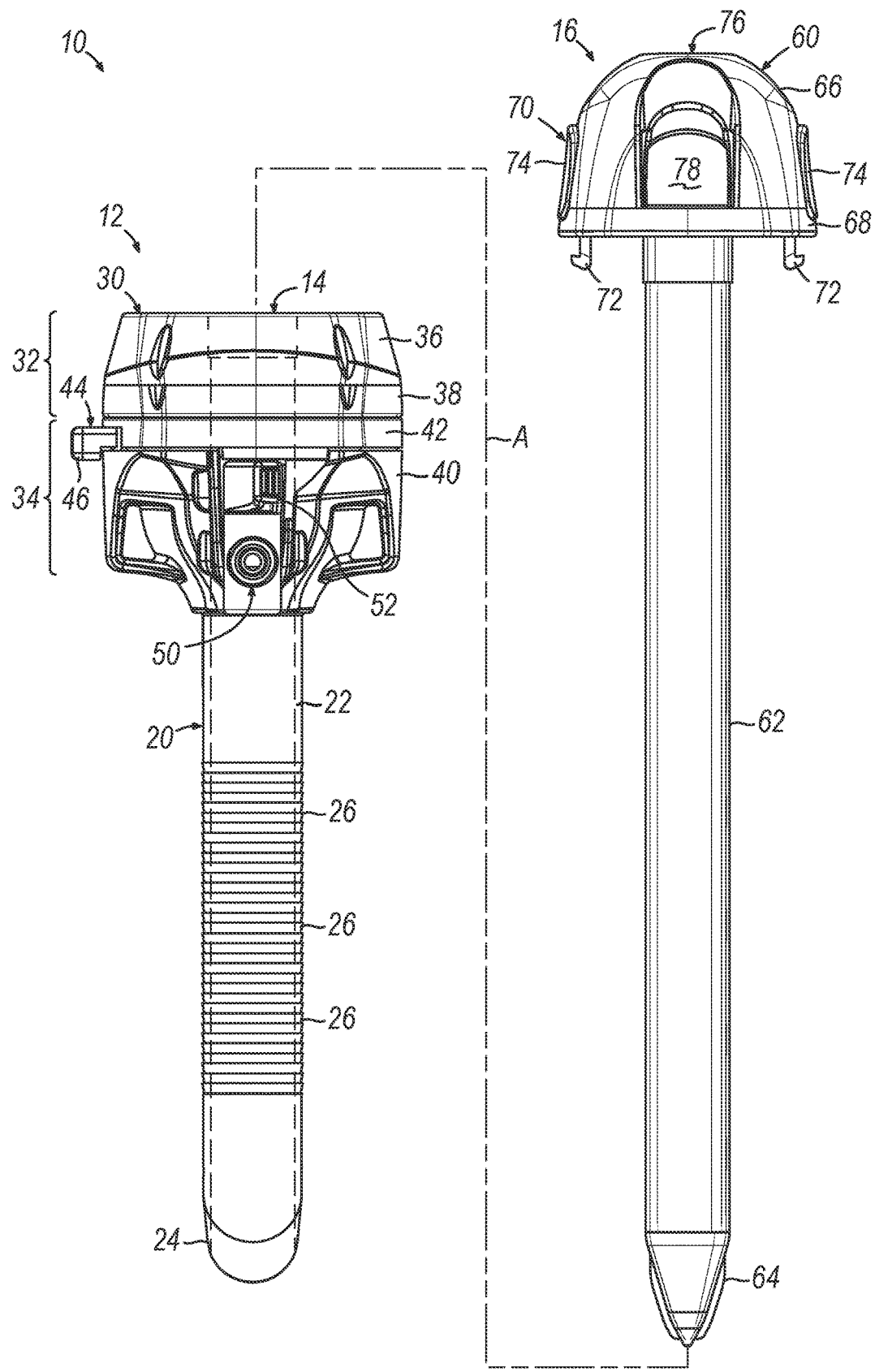
FIG. 2 depicts a side elevational view of the cannula assembly and the obturator of FIG. 1 in a disassembled state.

As shown in FIGS. 1-2, cannula assembly (12) of single-use trocar (10) includes a cannula (20) and a seal housing (30). Cannula (20) and seal housing (30) cooperate to define working channel (14), which extends longitudinally along a central axis (A) of trocar (10). In particular, working channel (14) is defined by a lumen of cannula (20) in communication with a hollow interior of seal housing (30). Cannula assembly (12) is configured to receive elongate surgical instruments distally through working channel (14) to provide access to surgical sites within the abdominal cavity of a patient. As described in greater detail below, seal housing (30) houses a pair of seal structures defining a seal assembly configured to maintain insufflation of the patient's abdominal cavity while permitting passage of surgical instruments and tissue fragments along working channel (14).

Cannula (20) of the present version may include a bell-shaped hub (not shown) at a proximal end thereof, and an elongate cylindrical tube (22) extending distally from the hub and terminating at an angled cannula tip (24). An outer surface of cannula tube (22) includes a plurality of tissue gripping features in the form of annular ribs (26) arranged axially along a medial portion of cannula tube (22). Ribs (26) are configured to grip the layers of abdominal wall tissue through which cannula (20) is inserted, and thereby assist in stabilizing cannula (20) in axial and radial directions while cannula (20) is positioned within the opening formed in the abdominal wall of a patient.

More specifically, tissue gripping ribs (26) of the present example are formed as annular scallops in the sidewall of cannula tube (22) such that each rib (26) tapers radially inwardly in a distal direction from a radially outermost edge of the rib (26). The radially outermost edges of ribs (26) are thus generally flush with the non-ribbed proximal and distal portions of cannula tube (22). The resulting configuration of ribs (26) promotes advancement of cannula tube (22) through tissue layers in a distal direction and resists retraction of cannula tube (22) through the tissue layers in a reverse, proximal direction. Advantageously, this configuration protects against unintended withdrawal of cannula tube (22) from the abdominal wall of patient during a surgical procedure. It will be appreciated, however, that cannula tube (22) may be provided with various other types of tissue gripping features in other versions of trocar (10). For instance, cannula tube (22) may include a tissue gripping feature in the form of one or more helical ribs that extend around at least a medial portion of cannula tube (22), and which may be scalloped similar to ribs (26).

Seal housing (30) of cannula assembly (12) includes a proximal housing portion (32) and a distal housing portion (34) to which proximal housing portion (32) is removably attached. Proximal housing portion (32) includes a proximal head (36) and a distal base (38) secured together. Distal housing portion (34) includes a distal shroud (40) that encircles the proximal hub (not shown) of cannula (20), a cap plate (42) secured to a proximal end of distal shroud (40), and a latch ring (44) rotatably disposed therebetween and having a radially outwardly projecting tab (46). Latch ring (44) is selectively rotatable via tab (46) about the central axis (A) of trocar (10) between a locked position and an unlocked position. In the locked position, latch ring (44) locks proximal housing portion (32) to distal housing portion (34). In the unlocked position, latch ring (44) permits separation of proximal housing portion (32) from distal housing portion (34), for example to directly access a distal seal structure (not shown) housed within distal housing portion (34). In some versions, distal shroud (40) may be formed integrally with the proximal end of cannula tube (22) such that distal shroud (40) is a component of cannula (20).

Though not shown, proximal housing portion (32) houses a proximal (or "outer") seal structure, and distal housing portion (34) houses a distal (or "inner") seal structure, both arranged along the central axis (A) of trocar (10). The proximal and distal seal structures cooperate to define a seal assembly that maintains insufflation of the patient's abdominal cavity during a surgical procedure while permitting passage of surgical instruments and tissue fragments along working channel (14). For instance, the proximal seal structure may include an annular seal member configured to sealingly engage the shaft of a laparoscopic surgical instrument directed through working channel (14). The distal seal structure may include a duckbill seal member configured to maintain working channel (14) in a sealed stated in the absence of a surgical instrument shaft.

Cannula assembly (12) further includes an insufflation port (50) operatively coupled with the proximal end of cannula (20) and having an adjustable valve in the form of a stopcock (52). Insufflation port (50) is configured to direct insufflation fluid, such as carbon dioxide, from a fluid source (not shown) distally through working channel (14) and into the patient's abdominal cavity to thereby expand (or "insufflate") the cavity with the fluid. This expansion of the abdominal cavity creates additional space for performing a laparoscopic surgical procedure with improved ease.

As shown in FIGS. 1 and 2, obturator (16) of trocar (10) includes a proximal head (60), an elongate cylindrical shaft (62) extending distally from head (60), and a tapered distal tip (64). Obturator shaft (62) is configured to be received within working channel (14) of cannula assembly (12) such that obturator tip (64) extends through and distally of cannula tip (24). Obturator head (60) includes a domed upper body (66), a base plate (68), and an actuatable latch member (70), which includes a pair of latch arms (72) and a corresponding pair of latch buttons (74). Latch arms (72) are configured to be captured within respective slots (not shown) formed in a top surface of seal housing head (36) to couple obturator (16) with cannula assembly (12). Latch buttons (74) are actuatable to release latch arms (72) from the slots and thereby permit separation of obturator (16) from cannula assembly (12). Obturator (16) further includes a central passage (76) that extends longitudinally through obturator head (60) and obturator shaft (62), and is configured to receive an endoscope (not shown) therein to provide visualization during insertion of trocar (10) through the abdominal wall of a patient. A clamp lever (78) of obturator head (60) is pivotable to selectively fix the endoscope within central passage (76). Central passage (76) and clamp lever (78) are merely optional features and may be omitted from obturator (16) in other versions.

Cannula assembly (12) and obturator (16) may be constructed to be disposed of after a single use with a patient. In other versions, one or more components of trocar (10) may be suitably constructed to withstand sterilization and multiple reuses, for example as described in greater detail below in connection with trocar (110) of FIGS. 4-5.

B. Exemplary Deployment of Trocar Into Patient Abdominal Cavity

FIGS. 3A-3D illustrate an exemplary method of accessing an abdominal cavity (1) of a patient through the patient's abdominal wall (2) with trocar (10) described above. It will be appreciated that abdominal wall (2) includes outward superficial layers and inward deep layers. Superficial layers generally include an outer layer of skin (3) and an inner layer of fat (4); whereas the deeper layers include alternating layers of muscle (5) and fascia (6), which are fibrous and flexible with relatively higher tensile strength than the superficial layers.

Figure 3A:
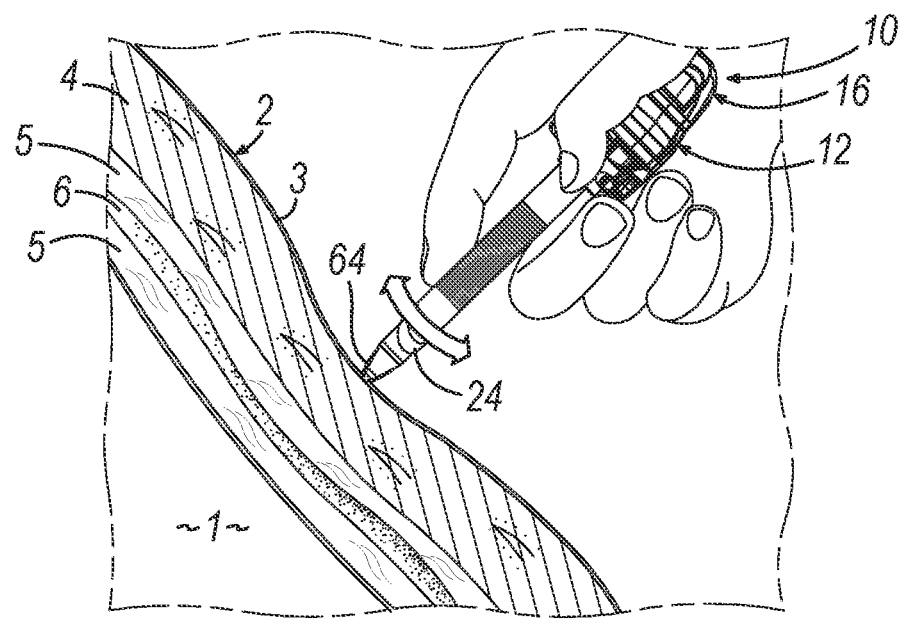
FIG. 3A depicts a side sectional view of the trocar of FIG. 1 being manipulated by a clinician through tissue layers of an abdominal wall.
Figure 3B:
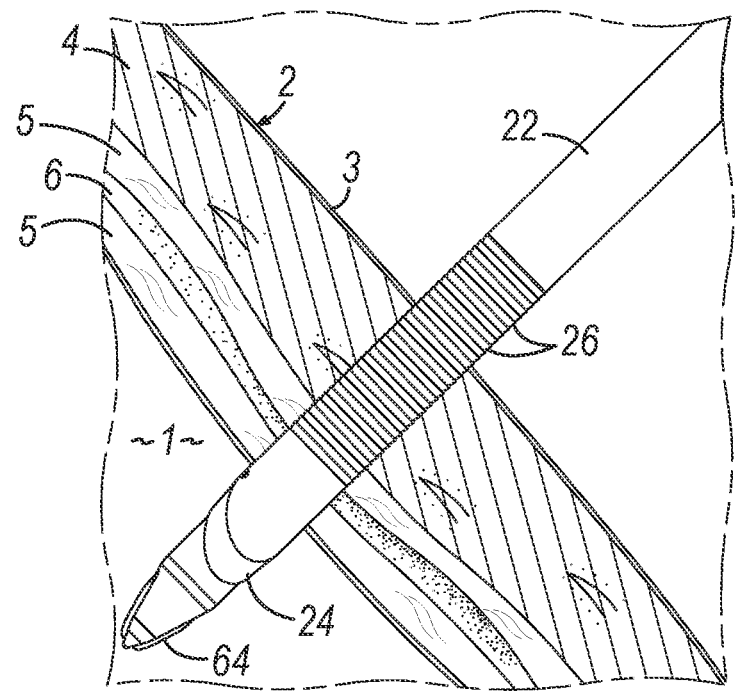
FIG. 3B depicts an enlarged side sectional view of the trocar of FIG. 1, showing a distal end of the trocar received within the abdominal cavity of FIG. 3A.
Figure 3C:
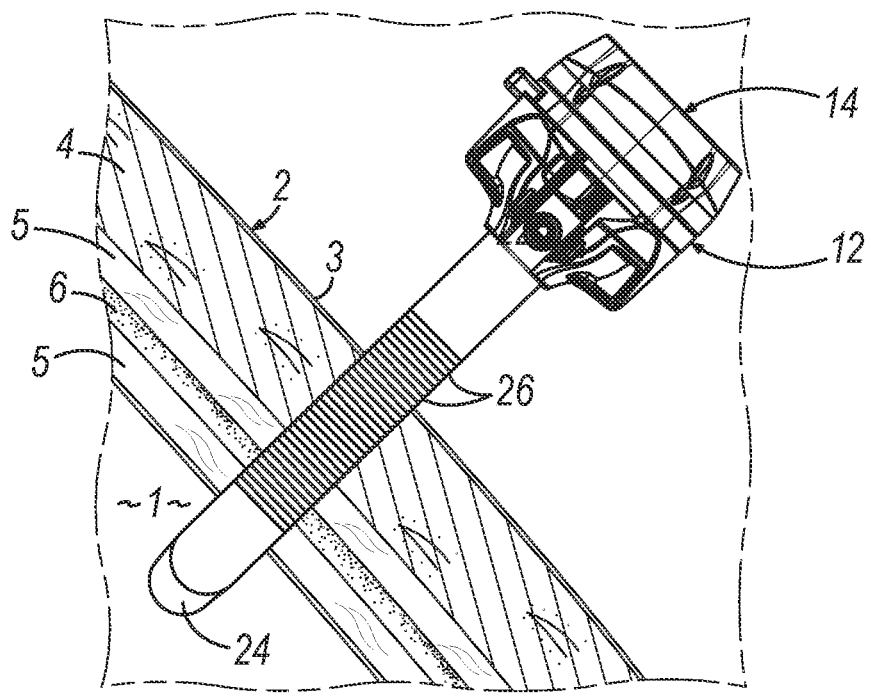
FIG. 3C depicts a side sectional view of the cannula assembly of FIG. 1, showing the cannula assembly remaining positioned within the abdominal wall of FIG. 3A following detachment and removal of the obturator.
Figure 3D:
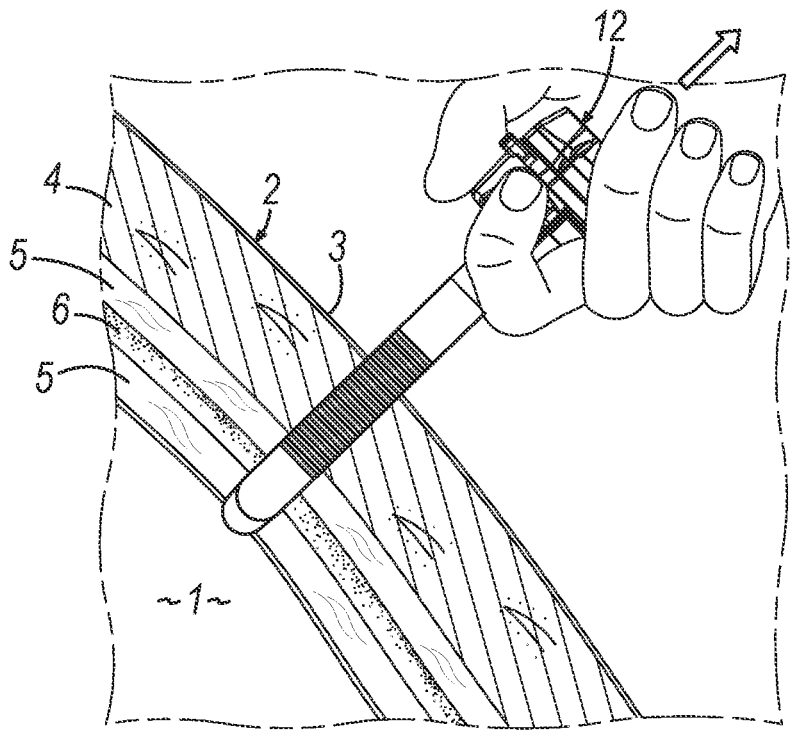
FIG. 3D depicts a side sectional view of the cannula assembly of FIG. 1 being withdrawn proximally from the abdominal wall of FIG. 3A.

As shown in FIG. 3A, with obturator (16) received within cannula assembly (12) and connected to seal housing (30), a clinician manipulates trocar (10) via obturator head (60) and seal housing (30) to urge obturator tip (64) against skin (3) and inward toward abdominal cavity (1) while rotating trocar (10) back and forth. Continued inward urging of trocar (10) further directs obturator tip (64) and cannula tip (24) distally through the layers of fat (4) and fascia (5) and into cavity (1), as shown in FIG. 3B. As discussed above, this step may be facilitated with visualization provided by an endoscope (not shown) mounted within obturator (16). Once cannula (20) has reached a desired depth of insertion into cavity (1), the clinician releases obturator head (60) from seal housing (30) via depression of latch buttons (74), and then withdraws obturator (16) from proximally from cannula assembly (12), as shown in FIG. 3C. This renders working channel (14) of cannula assembly (12) free to receive surgical instruments distally therethrough for performing the laparoscopic surgical procedure. As described above, tissue engagement ribs (26) provided on cannula tube (22) grip the layers of tissue (3, 4, 5) of abdominal wall (2), thus providing cannula assembly (12) with at least a minimum degree of stability relative to abdominal wall (2). Upon completion of the laparoscopic surgical procedure, the clinician grasps seal housing (30) and withdraws cannula assembly (12) proximally from abdominal wall (2), as shown in FIG. 3D.

C. Exemplary Reusable Trocar Having Disposable Seal Assembly

Figure 4:
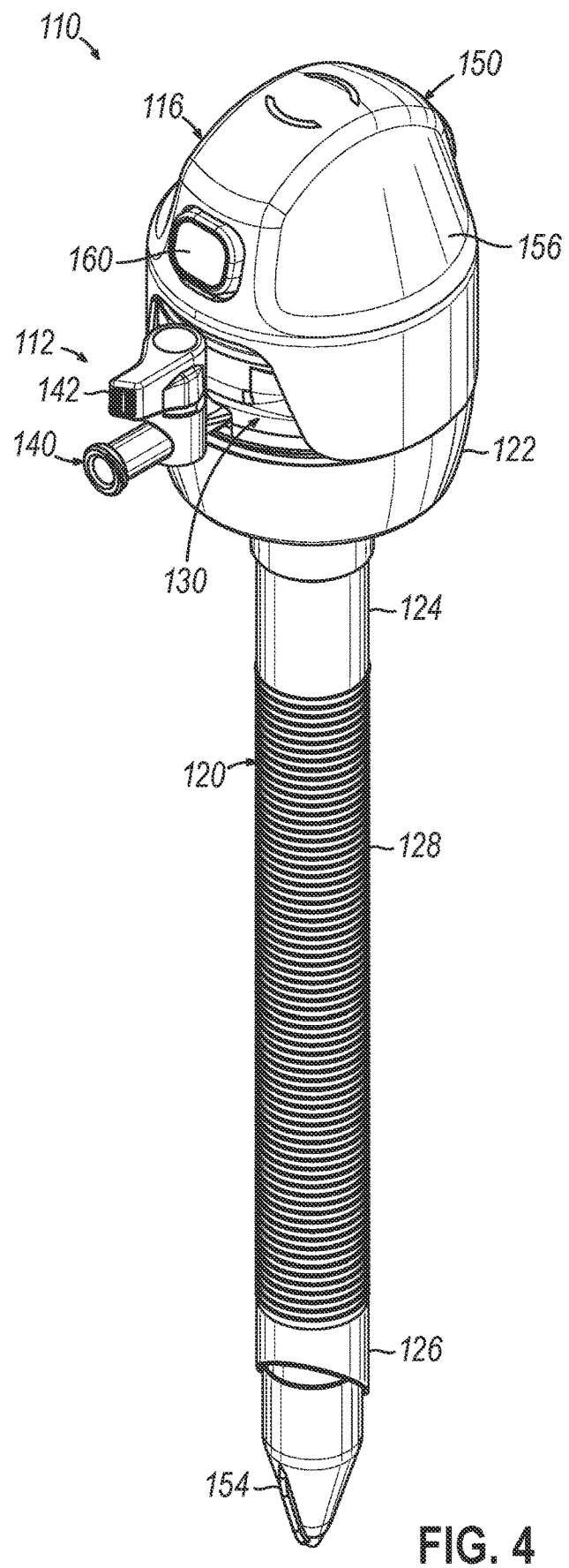
FIG. 4 depicts a perspective view of another exemplary trocar having a cannula assembly and an obturator shown in an assembled state.
Figure 5:
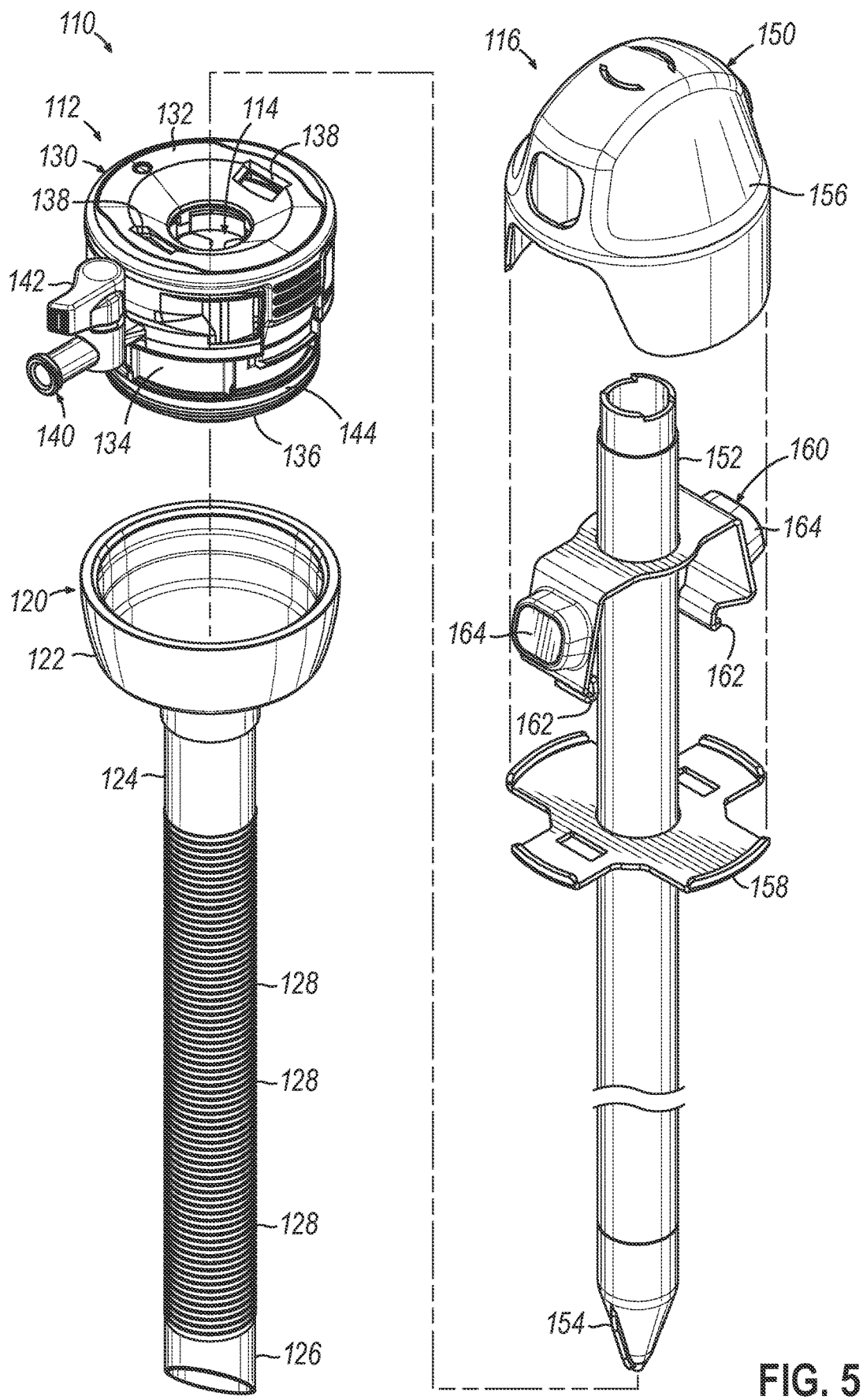
FIG. 5 depicts a perspective view of the cannula assembly and the obturator of FIG. 4 in a disassembled state, showing a reusable cannula and a disposable seal assembly of the cannula assembly separated from one another, and showing the obturator in an exploded state.

In some instances, it may be desirable to configure a trocar such that one or more components thereof may be sterilized and reused for multiple surgical procedures, while one or more other components may be easily and economically disposed of and replaced after each procedure. FIGS. 4-5 show another exemplary trocar (110) that is configured in such a manner, and which is similar in structure and function to trocar (10) described above except as otherwise described below.

Similar to trocar (10), trocar (110) includes a cannula assembly (112) having a working channel (114) and an obturator (116) configured to be inserted into cannula assembly (112) coaxially along working channel (114). Cannula assembly (112) includes a cannula (120) having a bell-shaped hub (122) at a proximal end thereof, and an elongate cylindrical tube (124) extending distally from hub (122) and terminating at an angled cannula tip (126). An outer surface of cannula tube (124) includes a plurality of tissue gripping features in the form of annular ribs (128) arranged axially along a medial portion of cannula tube (124) and which are similar to ribs (26) described above.

Cannula assembly (112) further includes a seal assembly (130). Unlike the seal assembly defined by seal housing (30) of trocar (10), seal assembly (130) is constructed as a modular, replaceable unit configured to releasably mate with proximal hub (122) of cannula (120). As shown best in FIG. 5, seal assembly (130) of the present example generally includes an upper frame member (132), a middle frame member (134), and a lower frame member (136) secured relative to one another in a coaxial arrangement. Though not shown, a proximal (or "outer") seal structure is supported within upper frame member (132), and a distal (or "inner") seal structure is supported within lower frame member (136). Such seal structures may be similar in structure and function to the proximal and distal seal structures of trocar (10) described above. Seal assembly (130) further includes an insufflation port (140) having an adjustable valve in the form of a stopcock (142).

A lower portion of seal assembly (130) distal to insufflation port (140) is configured to seat within proximal hub (122) of cannula (120) such than an annular seal member (144) disposed circumferentially about the lower portion sealingly engages an inner surface of cannula hub (122). In this manner, an interior of seal assembly (130) fluidly communicates with a lumen of cannula (120) to define a working channel (114) of cannula assembly (112) through which insufflation fluid, surgical instruments, and tissue fragments may be directed in the manners generally described above in connection with trocar (10). Seal assembly (130) may be further configured in accordance with one or more teachings of U.S. Pat. Pub. No. 2019/0090905, entitled "Trocar Seal Assemblies," published Mar. 28, 2019, the disclosure of which is incorporated by reference herein; and/or U.S. Pat. Pub. No. 2019/0380742, entitled "Asymmetric Shaft Seal," published Dec. 19, 2019, the disclosure of which is incorporated by reference herein.

As shown best in FIG. 5, obturator (116) of trocar (110) includes a proximal head (150), an elongate cylindrical shaft (152) extending distally from head (150), and a tapered tip (154) at a distal end of shaft (152). Obturator head (150) includes a domed upper body (156), a base plate (158), and an actuatable latch member (160), which includes a pair of downwardly extending latch arms (162) and a corresponding pair of latch buttons (164). Latch arms (162) are configured to be captured within respective slots (138) formed in a top surface of upper frame member (132) of seal assembly (130) to couple obturator (116) with cannula assembly (112). Latch buttons (164) are actuatable to release latch arms (162) from slots (138) and thereby permit separation of obturator (116) from cannula assembly (112).

Cannula (120) and obturator (116) of the present example are suitably constructed of a robust material, such as surgical steel, such that they may be sterilized and reused for multiple surgical procedures. In contrast, as described above, seal assembly (130) is constructed as a disposable unit, intended to be separated from cannula (120) and replaced after each procedure. For instance, seal assembly (130) may be constructed of various polymeric materials, including plastics and rubbers, such that seal assembly (130) may be easily manufactured and sold at a price point that renders seal assembly (130) suitable for disposal after a single use, similar to trocar (10) described above.

II. Gyroscopic Stabilization of Surgical Instruments

As described above, trocar cannulas (20, 120) each include a tissue gripping stability feature in the form of annular ribs (26, 128). Ribs (26, 128) (also referred to as stability threads) are configured to grip the various tissue layers of a patient's abdominal wall (2) and thereby assist in maintaining a user-defined angular of the corresponding cannula assembly (12, 112) relative to the patient during a surgical procedure. In some instances, however, ribs (26, 128) may be ineffective to inhibit gravity-induced tip (also referred to as tilt) of cannula assembly (12, 112) toward abdominal wall (2) and away from the user-defined orientation, particularly when a surgeon releases cannula assembly (12, 112) from his or her grasp to perform another task. Accordingly, it may be desirable to couple cannula assembly (12, 112) with a device configured to assist in maintaining a user-defined orientation of cannula assembly (12, 112) relative to the patient.

Figure 6:
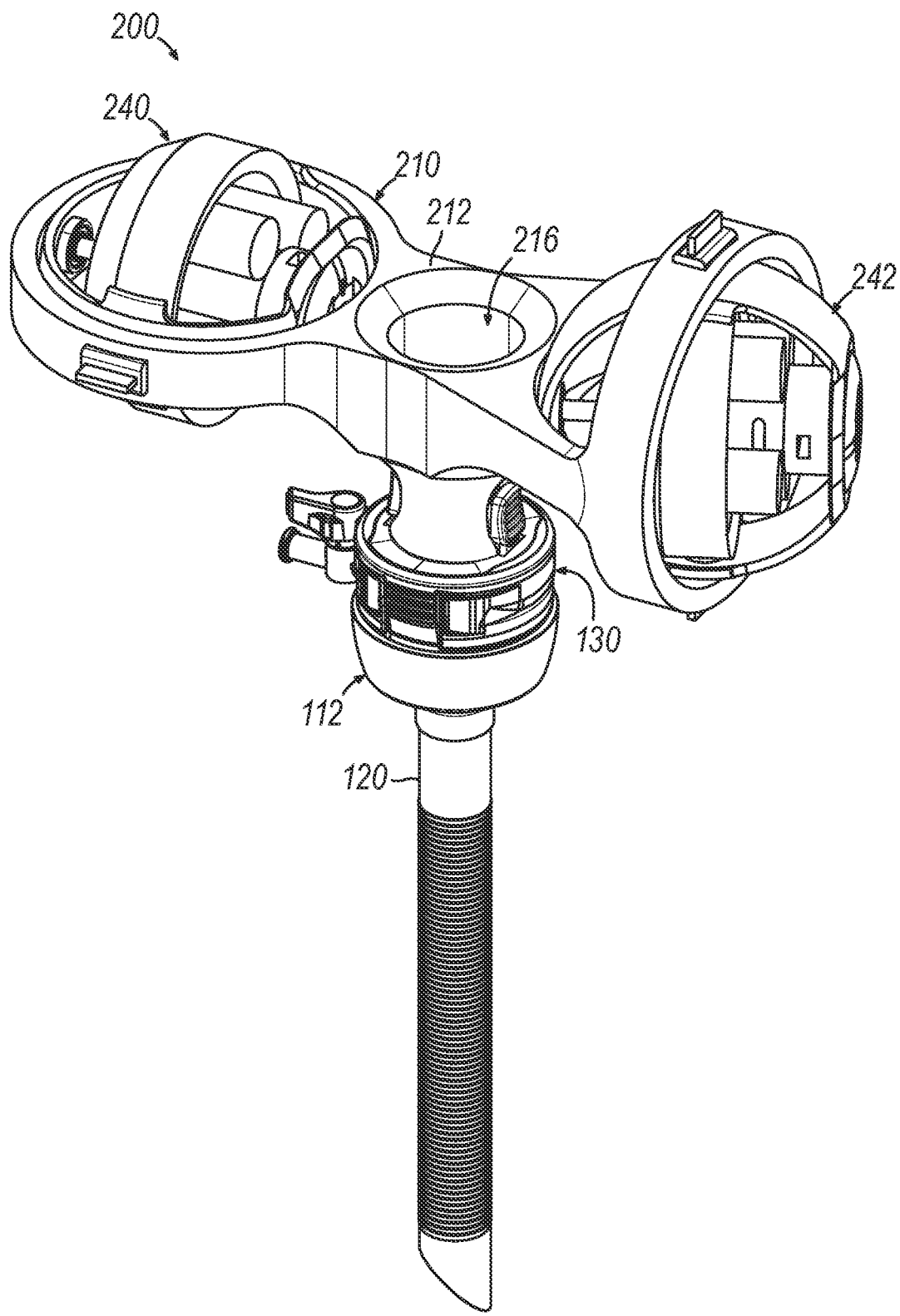
FIG. 6 depicts a perspective view of an exemplary gyroscopic surgical instrument assembly that includes a gyroscopic stabilizer releasably coupled with a surgical instrument in the form of the cannula assembly of FIG. 4.

FIG. 6 shows an exemplary gyroscopic surgical instrument assembly (200) that includes cannula assembly (112) of trocar (110), described above, in combination with an exemplary gyroscopic stabilizer (210). As described in greater detail below, gyroscopic stabilizer (210) is operable to maintain a user-defined angular orientation (i.e., tilt angle) of cannula assembly (112) relative to a patient when a surgeon has released cannula assembly (112) from his or her grasp or control, thus enabling the surgeon to safely perform other surgical tasks without having to manually maintain or otherwise monitor the angular orientation of cannula assembly (112). More specifically, gyroscopic stabilizer (210) leverages the principle of conservation of angular momentum to counteract externally applied torques due to gravitational forces, tissue reactive forces, and unintentional user input forces, for example. In some instances, gyroscopic stabilizer (210) may be controlled to detect and facilitate surgical movements applied to cannula assembly (112) by a surgeon via a laparoscopic surgical instrument directed through cannula assembly (112).

Figure 13A:
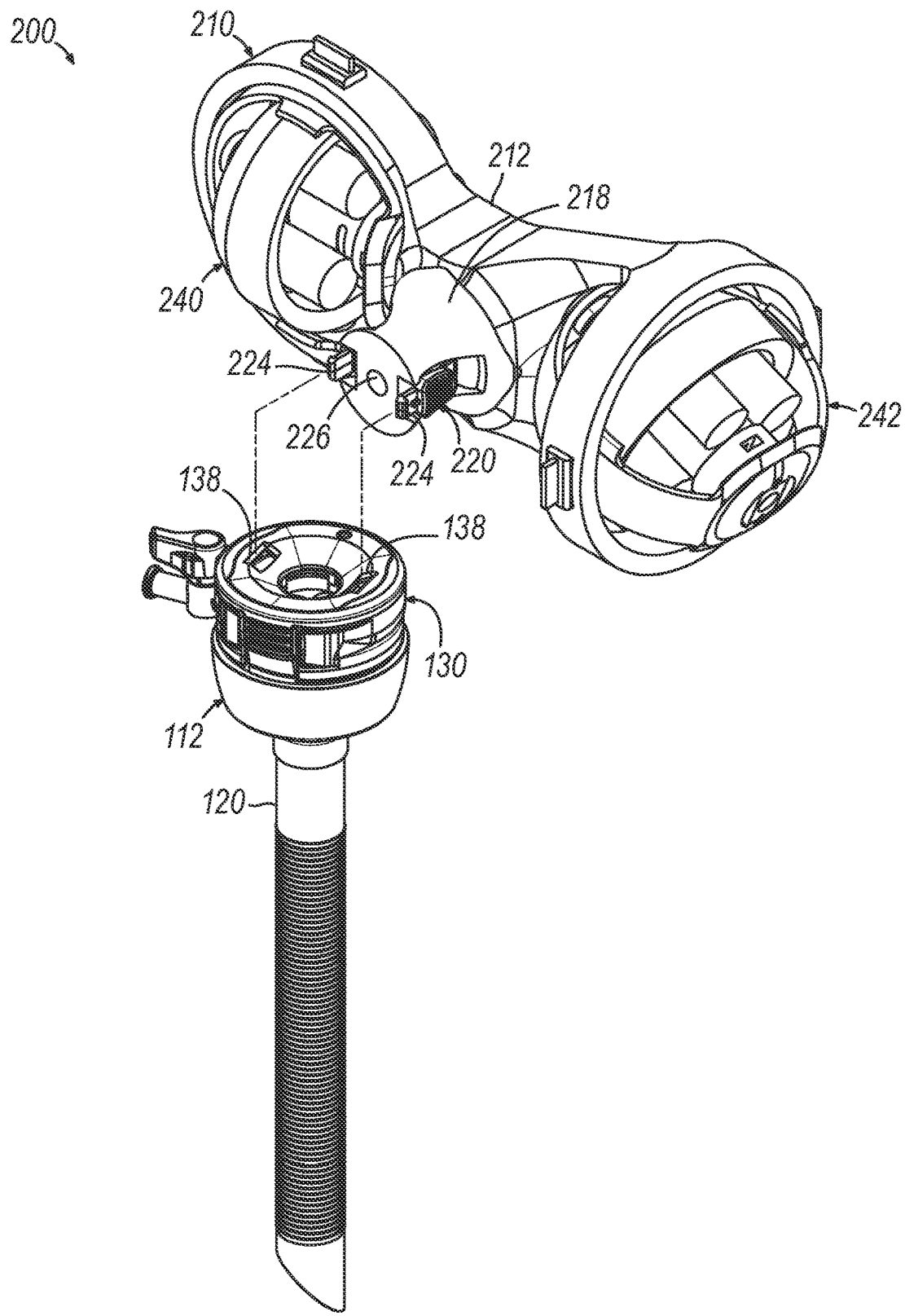
FIG. 13A depicts a perspective view of the gyroscopic surgical instrument assembly of FIG. 6 in a disassembled state, showing the gyroscopic stabilizer being aligned with and coupled to the cannula assembly.

Gyroscopic stabilizer (210) is shown and described herein, particularly with reference to FIG. 13A, in connection with stabilizing a first surgical instrument in the form of cannula assembly (112) and a second surgical instrument in the form of a laparoscopic instrument (290) directed distally through cannula assembly (112). However, it will be appreciated that gyroscopic stabilizer (210) and its variations disclosed herein may also be used to stabilize various other types of trocar cannula assemblies, as well as various types of elongate, non-trocar surgical instruments in combination with or independently of a trocar cannula assembly. For instance, as described below in connection with FIG. 14, gyroscopic stabilizer (210) may be configured to couple with and stabilize a laparoscopic instrument (290) independently of cannula assembly (112). Accordingly, it will be understood that gyroscopic stabilizer (210) may have various suitable uses and applications in the surgical field other than those specifically disclosed herein.

A. Structural Overview of Exemplary Gyroscopic Stabilizer

Figure 7:
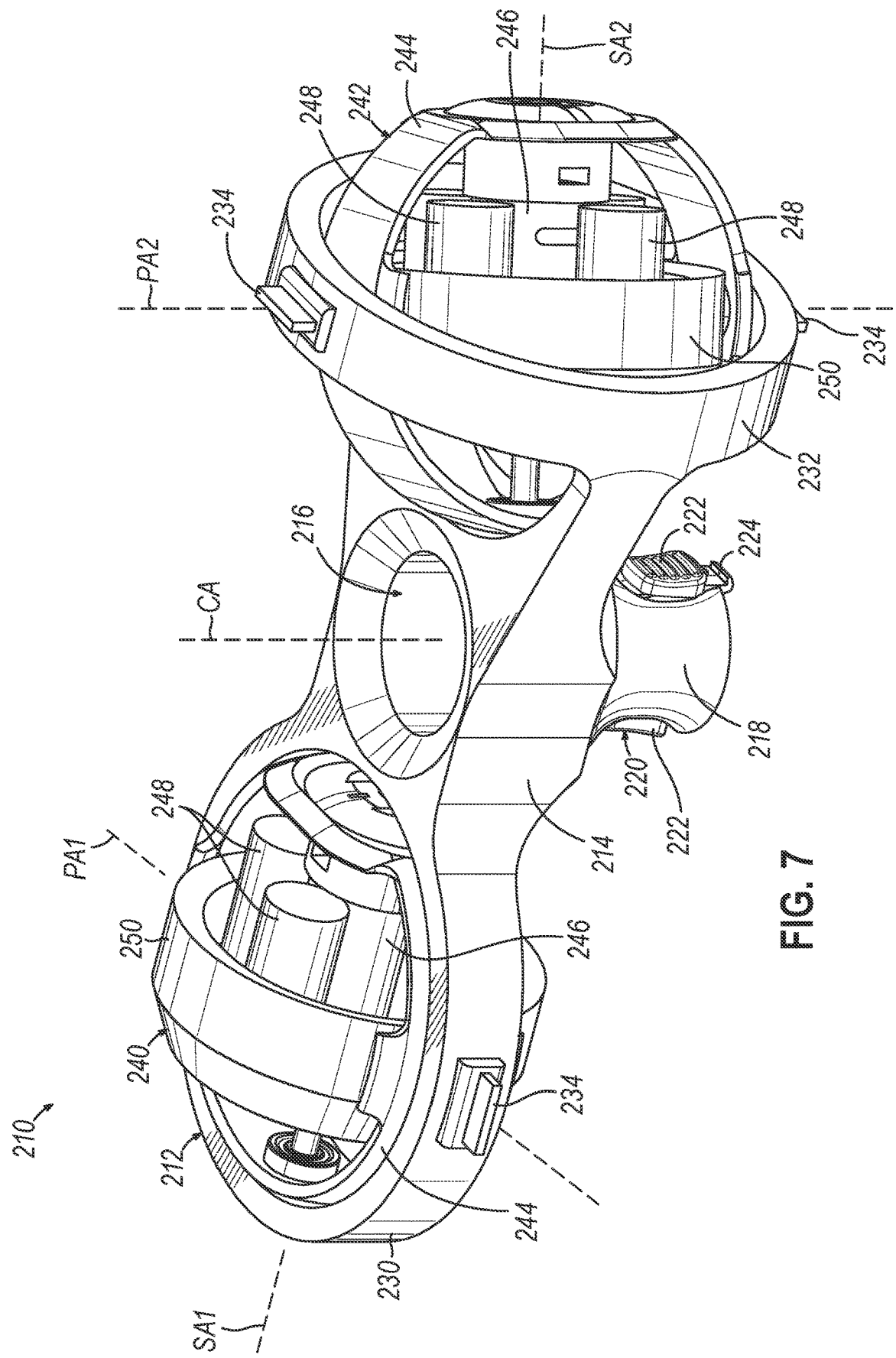
FIG. 7 depicts a perspective view of the gyroscopic stabilizer of FIG. 6, shown having a frame, a first gyroscope assembly coupled with a first frame portion, and a second gyroscope assembly coupled with a second frame portion.
Figure 8:
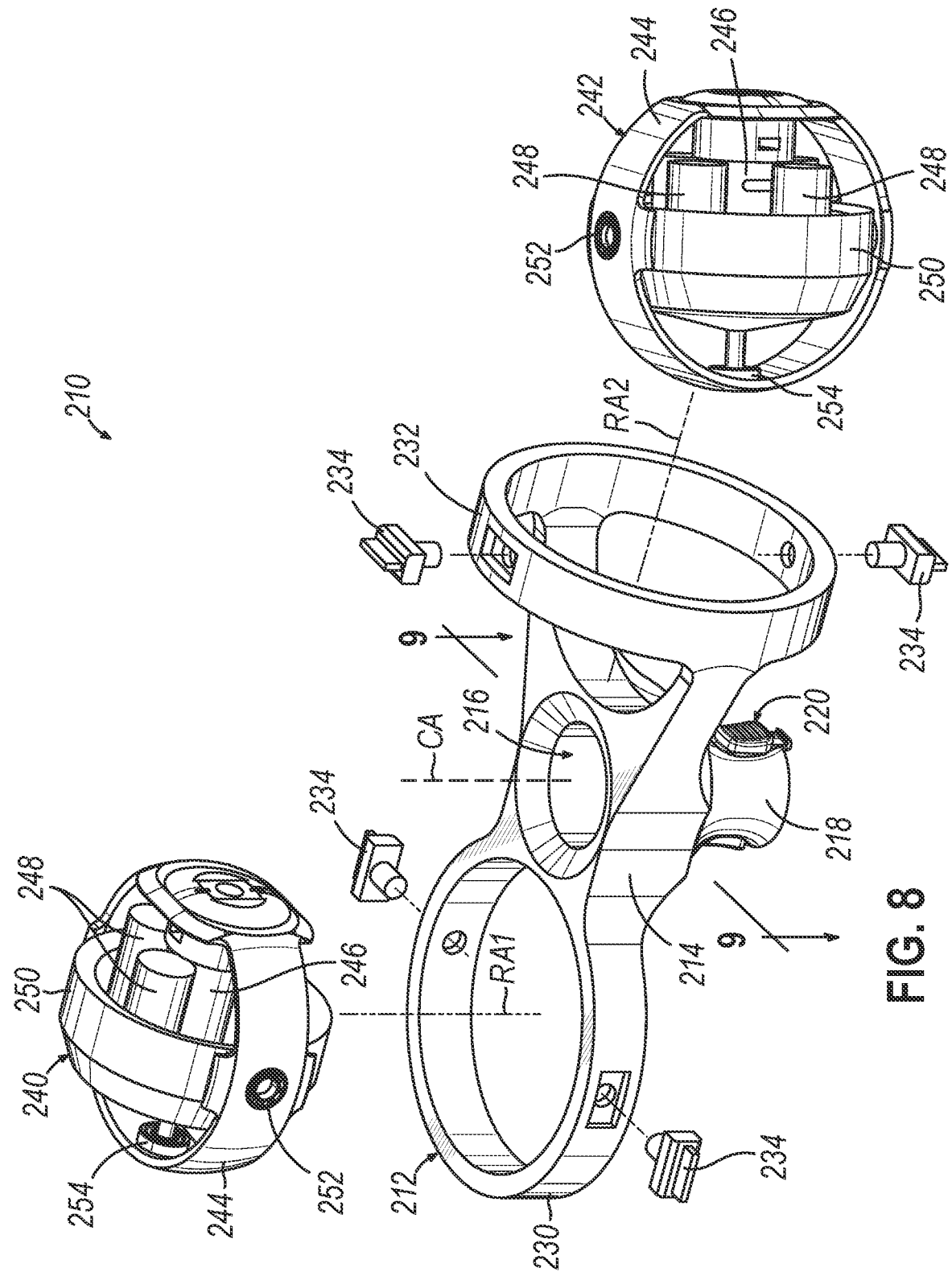
FIG. 8 depicts a partially exploded perspective view of the gyroscopic stabilizer of FIG. 6, showing the first gyroscope assembly separated from the first frame portion and the second gyroscope assembly separated from the second frame portion.

As shown best in FIGS. 7 and 8, gyroscopic stabilizer (210) of the present version includes a frame (212), a first gyroscope assembly (240) movably coupled with a first portion of frame (212), and a second gyroscope assembly (242) movably coupled with a second portion of frame (212).

Frame (212) of the present version is formed as a unitary structure having a central hub (214) that defines a central axis (CA) of frame (212) and includes a cylindrical central passage (216), which extends distally through hub (214) along central axis (CA). A generally cylindrical collar (218) extends distally from an underside of central hub (214) along central axis (CA) and houses an instrument coupling mechanism in the form of an actuatable latch member (220). Latch member (220) includes a pair of buttons (222) and a corresponding pair of downwardly depending latch arms (224). Latch buttons (222) are selectively actuatable by a user to couple and decouple latch arms (224) with a proximal end of cannula assembly (112), for example as shown and described below in connection with FIG. 13A. In this manner, collar (218) serves to releasably attach gyroscopic stabilizer (210) to cannula assembly (112), as well as elevate gyroscope assemblies (240, 242) above the proximal end of cannula assembly (112) to prevent interference. Various other types of instrument coupling mechanisms configured to couple gyroscopic stabilizer (210) with a cannula assembly (112) and/or other types of surgical instruments will be readily apparent to those of ordinary skill in the art in view of the teachings herein.

Figure 9:
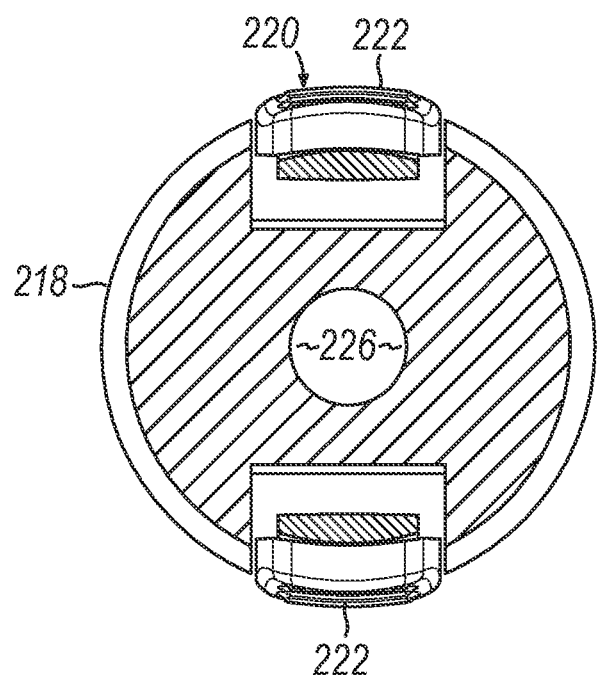
FIG. 9 depicts a top sectional view of a hub collar portion of the gyroscopic stabilizer of FIG. 6, taken along section line 9-9 in FIG. 8.

Referring briefly to FIG. 9, collar (218) includes a central bore (226) aligned coaxially with central passage (216) of hub (214) along central axis (CA). Central bore (226) of the present example has a smaller diameter than central passage (216) and is sized to slidably receive a shaft of a surgical instrument, such as a laparoscopic instrument in the form of a surgical stapler or an electrosurgical instrument, for example. In some versions, central bore (226) may be sized to engage the outer shaft surface of such a surgical instrument with a predetermined degree of friction, or with no friction.

As shown in FIGS. 7 and 8, stabilizer frame (212) further includes a first gyroscope support member in the form of a first ring member (230) disposed radially outwardly of a first side of central hub (214), and a second gyroscope support member in the form of a second ring member (232) disposed radially outwardly of an opposed second side of central hub (214). First and second ring members (230, 232) are diametrically opposed from one another about central axis (CA). First ring member (230) is oriented generally horizontally and coplanar with central hub (214), such that first ring member (230) extends circumferentially about a first ring member axis (RA1) that is parallel to and radially outwardly of central axis (CA). Conversely, second ring member (232) is oriented generally vertically and perpendicular to central hub (214), such that second ring member (232) extends circumferentially about a second ring member axis (RA2) that intersects central axis (CA) and first ring member axis (RA1) perpendicularly. Accordingly, first and second ring members (230, 232) of the present example are angled relative to one another by 90 degrees. Furthermore, first and second ring members (230, 232) are aligned with one another such that second ring member axis (RA2) lies within a horizontal mid-plane of first ring member (230).

First gyroscope assembly (240) is encircled by and pivotably coupled to first ring member (230) of stabilizer frame (212) about a first pivot axis referred to herein as a first precession axis (PA1). Similarly, second gyroscope assembly (242) is encircled by and pivotably coupled to second ring member (232) of stabilizer frame (212) about a second pivot axis referred to herein as a second precession axis (PA2). Accordingly, first and second gyroscope assemblies (240, 242) are diametrically opposed from one another and spaced equidistantly apart from one another about central axis (CA). As described in greater detail below in connection with FIG. 13B, each gyroscope assembly (240, 242) is configured to pivot, or "precess," relative to the respective ring member (230, 232) about its respective precession axis (PA1, PA2). The pivotable coupling between each gyroscope assembly (240, 242) and its respective ring member (230, 232) is provided by a pair of pivot post elements (234) that extend radially inwardly through diametrically opposed sides of the ring member (230, 232), toward the respective ring member axis (RA1, RA2). The inner end of each pivot post element (234) is received by a respective bearing of the respective gyroscope assembly (240, 242).

In the present example, first precession axis (PA1) extends horizontally along a diameter of first ring member (230), thus intersecting first ring member axis (RA1) perpendicularly. Second precession axis (PA2) extends vertically along a diameter of second ring member (232), thus intersecting second ring member axis (RA2) perpendicularly. Additionally, first precession axis (PA1) extends parallel to a vertical mid-plane of second ring member (232), and second precession axis (PA2) extends parallel to a horizontal mid-plane of first ring member (230). Accordingly, first and second precession axes (PA1, PA2) of the present example are angled relative to one another by 90 degrees.

In the present version of gyroscopic stabilizer (210), each gyroscope assembly (240, 242) is configured in the same manner. As shown best in FIGS. 10 and 11, each gyroscope assembly (240, 242) includes a gimbal (244), a motor (246) mounted to gimbal (244), a power source in the form of a plurality of batteries (248) arranged circumferentially about motor (246), and a rotor (250) (also referred to as a "flywheel") rotatably coupled with motor (246).

Gimbal (244) of the present version has an annular shape and a convex outer surface that facilitates pivoting (or "precessing") of gimbal (244) relative to the respective frame ring member (230, 232) without interference. Gimbal (244) further includes a pair of pivot bearings (252) configured to pivotably couple with the inner ends of pivot post elements (234) to enable pivoting of gimbal (244) relative to ring member (230, 232), and a single spin bearing (254) configured to pivotably couple with rotor (250). Spin bearing (254) is spaced equidistantly between pivot bearings (252) along a spin axis (SA1, SA2) about which rotor (250) is configured to rotate. Gimbal (244) further includes a motor support flange (256) diametrically opposed from spin bearing (254) and having an opening (258) configured to securely receive a motor mount cap (260). Motor mount cap (260) is configured to receive and support motor (246) and batteries securely relative to gimbal (244) and includes internal passages (262) configured to house electrical connectors (not shown) routed between motor (246) and batteries (248).

Motor (246) of the present example may be in the form of a brushed or brushless direct-current (DC) motor and includes an output shaft (264) fitted with a first drive coupling feature in the form of a pinion gear (266). Pinion gear (266) is configured to mate with a second drive coupling feature of rotor (250), described below. Each battery (248) may be rechargeable or non-rechargeable and may have an output voltage of approximately 3 volts, for example. In the present version, each gyroscope assembly (240, 242) includes four 3 volt batteries (248) connected to one another in series, thus providing a total output voltage of 12 volts for powering the respective motor (246). It will be appreciated that various other types and configurations of batteries may utilized for powering motors (246) in other versions. For instance, gyroscopic stabilizer (210) may include a single power source operable to power both motors (246). Additionally, though not shown, each gyroscope assembly (240, 242) may further include a switch configured to be actuated by a user to selectively power the respective motor (246) with the respective batteries (248) and thereby activate stabilization. In some versions, gyroscopic stabilizer (210) may include a single switch (not shown) configured to control power directed to both motors (246).

Figure 10:
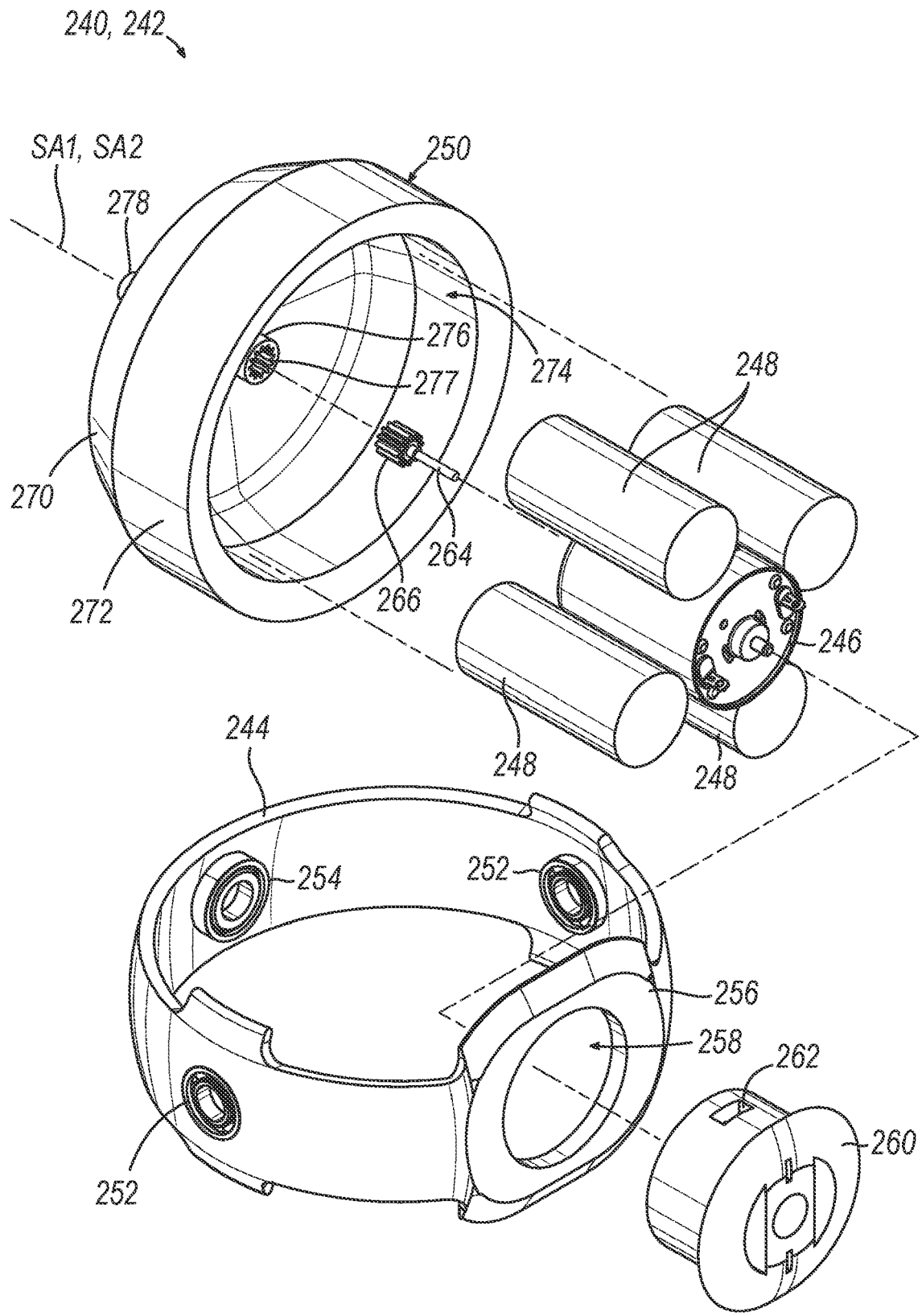
FIG. 10 depicts a partially exploded perspective view of a gyroscope assembly of the gyroscopic stabilizer of FIG. 6, showing additional details of the gyroscope assembly.
Figure 11:
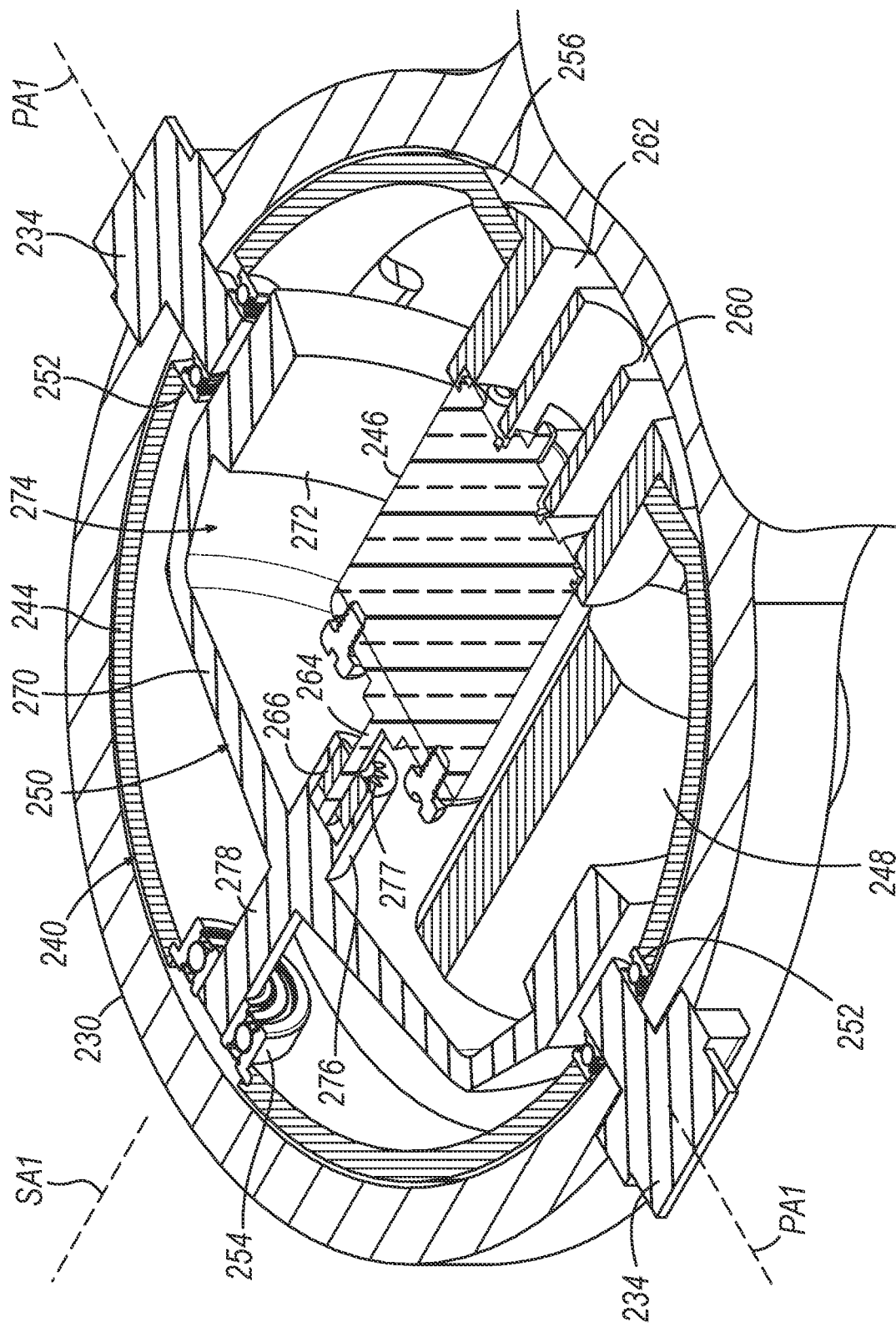
FIG. 11 depicts a top sectional view of the first gyroscope assembly and the first frame portion of the gyroscopic stabilizer of FIG. 6, taken along a plane defined by a spin axis and a precession axis of the gyroscope assembly.

As shown in FIGS. 10 and 11, rotor (250) (or "flywheel") of the present version is formed as a unitary structure having a bowl or truncated cup-like shape and radial symmetry about a central rotational axis, referred to herein as a spin axis (SA1, SA2). In particular, rotor (250) has a domed body portion (270), a ring portion (272) defining a circular opening to an inner cavity (274) of rotor (250), a drive coupling post (276) projecting axially into inner cavity (274) along the respective spin axis (SA1, SA2), and a spin post (278) projecting axially away from domed body portion (270) along spin axis (SA1, SA2). Spin post (278) is configured to be received by and rotatably couple with spin bearing (254) of gimbal (244) to enable rotation of rotor (250) relative to gimbal (244) about spin axis (SA1, SA2). Drive coupling post (276) includes a bore having a plurality of internal gear teeth (277) and is configured to receive and mate with pinion gear (266) of motor output shaft (264), thereby establishing a secure drive connection between motor (246) and rotor (250). Various other suitable types of drive connections between motor (246) and rotor (250) will be readily apparent to those of ordinary skill in the art in view of the teachings herein, for example as described below in connection with FIG. 12.

As shown best in FIG. 11, motor (246) and batteries (248) are supported by motor mount cap (260) such that motor (246) and batteries (248) are positioned along the respective spin axis (SA1, SA2) and at least partially within inner cavity (274) of rotor (250), such that ring portion (272) of rotor (250) is configured to rotate about motor (246) and batteries (248). This arrangement advantageously promotes a compact configuration of gyroscope assembly (240, 242).

As shown in FIG. 11, ring portion (272) of rotor (250) is generally aligned with precession axis (PA1, PA2) and may be formed with a thicker sidewall than domed body portion (270) to thereby concentrate the mass of rotor (250) along precession axis (PA1, PA2). Rotor (250) may be formed of one or more materials selected to provide rotor (250) with a suitable mass and resulting moment of inertia (also referred to as "rotational inertia") for generating stabilization torque in the manner described below. In some versions, rotor (250) may be formed entirely of a single metal, such as aluminum or steel. In other versions, domed body portion (270) may be formed of a first material having a first density, and ring portion (272) may be formed of a second material having a second density greater than the first density. By way of example only, domed body portion (270) may comprise a polymer, and ring portion (272) may comprise a metal.

Figure 12:
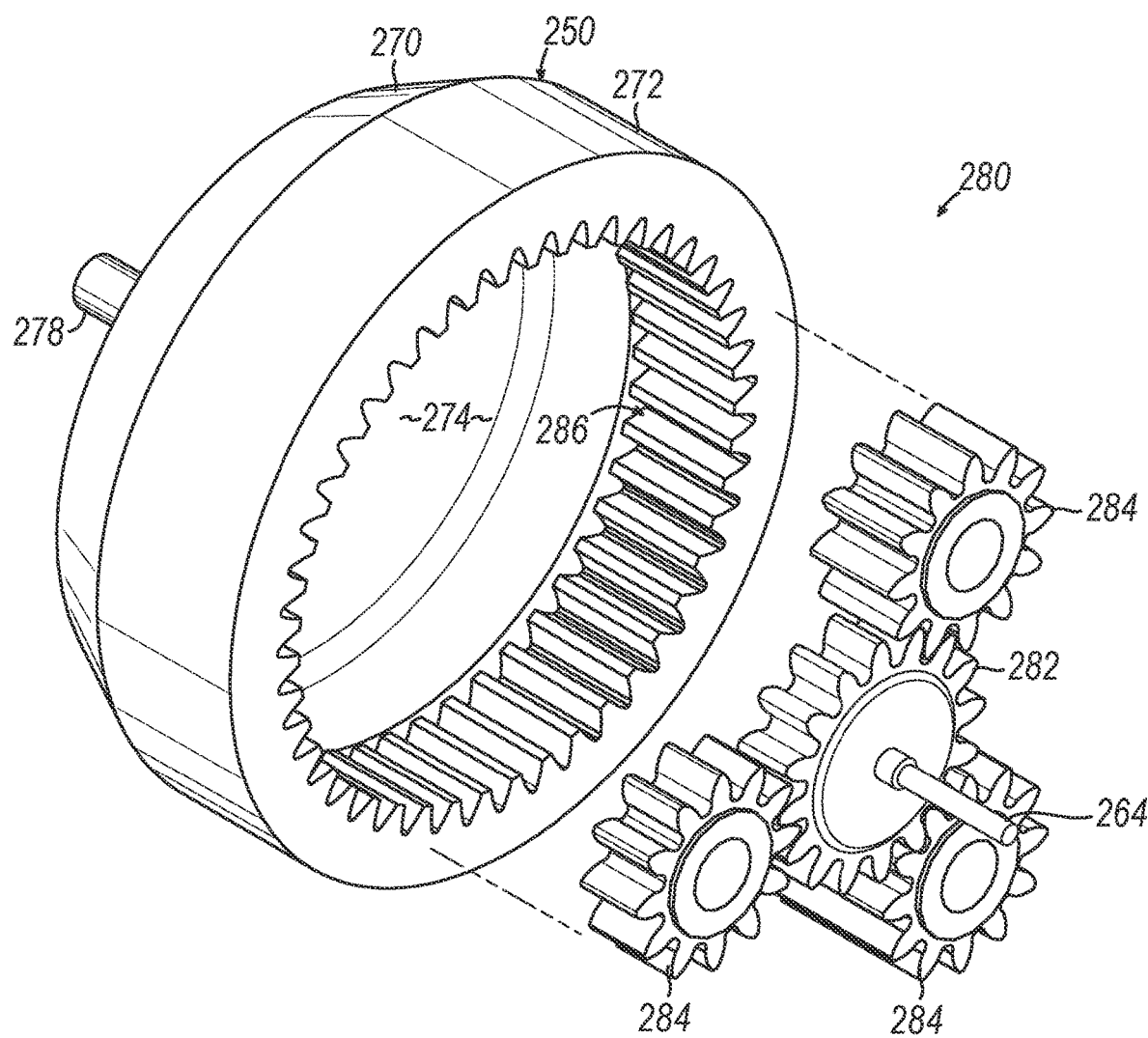
FIG. 12 depicts an exploded perspective view of an exemplary alternative drive coupling between a rotor and a motor of the gyroscope assembly of FIG. 10.

FIG. 12 shows an exemplary alternative drive coupling mechanism (280) configured to rotatably couple rotor (250) with motor (246). Drive coupling mechanism (280) is in the form of a planetary gear assembly having a central sun gear (282) coupled with motor output shaft (264), a plurality of planet gears (284) spaced circumferential about and in meshing engagement with sun gear (282), and a ring gear (286) integrated into the inner surface of rotor ring portion (272). As noted above, it will be understood that various other types of drive coupling mechanism may be implemented for rotatably coupling rotor (250) with motor (246).

B. Functional Overview of Exemplary Gyroscopic Stabilizer

Having described exemplary structural features of gyroscopic stabilizer (210) above in connection with FIGS. 6-12, exemplary operation of gyroscopic stabilizer (210) will now be described in connection with FIGS. 13A-14. As shown in FIG. 13A, gyroscopic stabilizer (210) is coupled with trocar cannula assembly (112) by directing latch arms (224) of latch member (220) into slots (138) formed in the proximal end of seal assembly (130). This yields the gyroscopic surgical instrument assembly (200) shown in FIGS. 6 and 13B in which central axis (CA) of gyroscopic stabilizer (210) is aligned coaxially with central axis (A) of cannula assembly (112). In this assembled configuration, central passage (216) and central bore (226) of stabilizer (210) communicate with working channel (114) of cannula assembly (112) through the open proximal end of seal assembly (130).

Figure 13B:
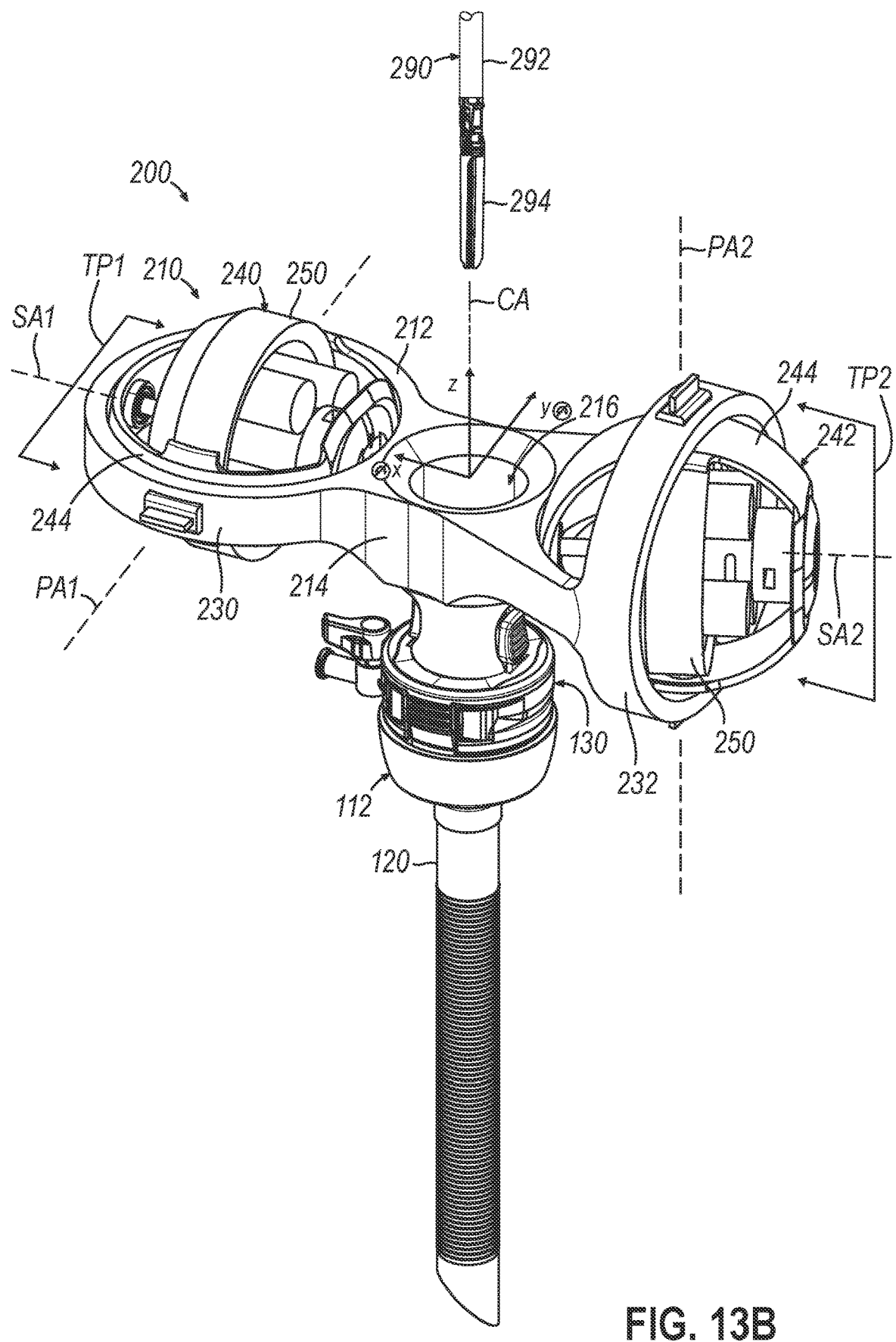
FIG. 13B depicts a perspective view of the gyroscopic surgical instrument assembly of FIG. 6 in an assembled state, showing a distal portion of an exemplary second surgical instrument being aligned with a central axis of the assembly for insertion distally through the gyroscopic stabilizer and the cannula assembly, and showing exemplary first and second torque planes in which the gyroscopic stabilizer is configured to generate stabilization torque for stabilizing the cannula assembly and the second surgical instrument relative to a patient.
Figure 14:
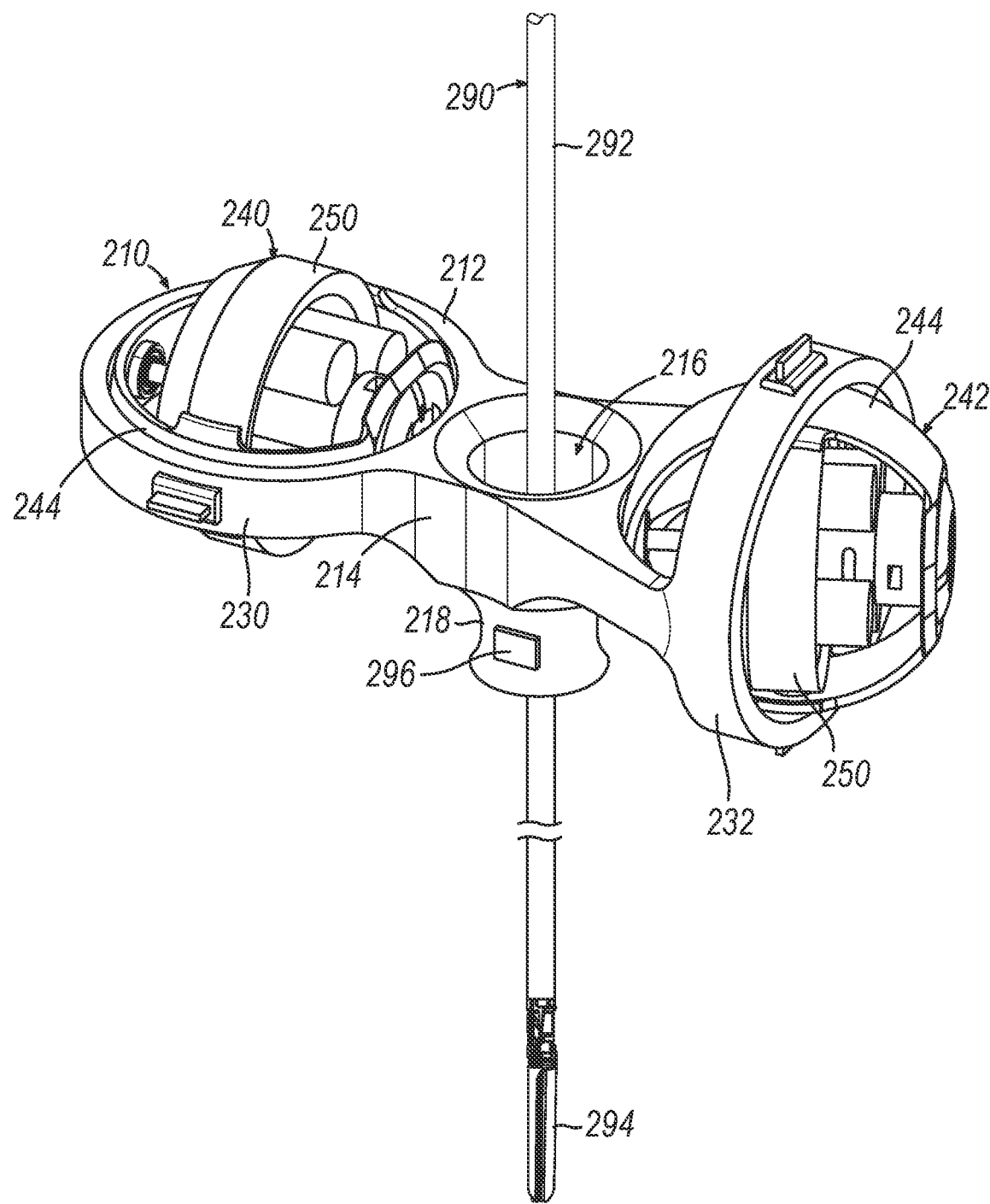
FIG. 14 depicts a perspective view of the gyroscopic stabilizer of FIG. 6 coupled to a shaft of the second surgical instrument of FIG. 13B without the cannula assembly of FIG. 4.

As shown in FIG. 13B, a laparoscopic surgical instrument (290) may then be directed downwardly through stabilizer hub (214) and cannula assembly (112) along the coaxial central axes (A, CA) for accessing a surgical site within the abdominal cavity (1) of a patient (see, e.g., FIG. 3C). Surgical instrument (290) of the present example includes a body assembly (not shown) configured to be grasped by a surgeon or supported by a robot; an elongate shaft (292) extending distally from the body portion; and an end effector (294) at a distal end of shaft (292). By way of example only, end effector (294) may be operable to grasp, manipulate, staple, cut, collect, and/or seal tissue. In that regard, and by way of example only, it will be appreciated that laparoscopic surgical instrument (290) may be in the form of a surgical stapling instrument, an ultrasonic surgical instrument, an electrosurgical instrument, a tissue suturing instrument, a tissue grasping instrument, a clip applying instrument, a tissue collecting instrument, or various other types of laparoscopic surgical instruments readily apparent those of ordinary skill in the art in view of the teachings herein. For instance, surgical instrument (290) may be in the form of any of the laparoscopic surgical instruments made available by Ethicon LLC of Guaynabo, Puerto Rico.

As described briefly above, gyroscopic stabilizer (210) in an activated (i.e., powered) state is operable to maintain a user-defined angular orientation of the surgical instrument with which stabilizer (210) is coupled by counteracting external torques applied to the surgical instrument, for example due to gravity. More specifically, as shown in the exemplary application of stabilizer (210) depicted in FIG. 13B, first gyroscope assembly (240) is operable to generate a first gyroscopic torque in a first torque plane (TP1) that contains first spin axis (SA1) and first precession axis (PA1). A component of this first gyroscopic torque is a first stabilization torque, which is configured to inhibit rotation (i.e., tilting) of stabilizer (210), and thus cannula assembly (112) and surgical instrument (290), about the illustrated x-axis defined by stabilizer frame (212). Second gyroscope assembly (242) is operable to generate a second gyroscopic torque in a second torque plane (TP2) that contains second spin axis (SA2) and second precession axis (PA2). A component of this second gyroscopic torque is a second stabilization torque, which is configured to inhibit rotation (i.e., tilting) of stabilizer (210), and thus cannula assembly (112) and surgical instrument (290), about the illustrated y-axis defined by stabilizer frame (212).

Each gyroscope assembly (240, 242) is configured to pivot (i.e., "precess") within and relative to its respective stabilizer frame ring member (230, 232) in response to an external force (e.g., gravity) applied to stabilizer (210) or cannula assembly (112). In this manner, each torque plane (TP1, TP2) pivots about its respective precession axis (PA1, PA2) to reorient the stabilization torque generated and thereby counteract the externally applied force to maintain the user-defined angular orientation of gyroscopic stabilizer (210), cannula assembly (112), and surgical instrument (290) relative to a patient. As described in greater detail below, the precession of gyroscope assemblies (240, 242) may be controlled to selectively vary the magnitude and/or direction of the stabilization torque output by gyroscope assemblies (240, 242) when activated.

Each gyroscope assembly (240, 242) of gyroscopic stabilizer (210) is operable to generate stabilization torque via the law of conservation of angular momentum, as will be understood by persons of ordinary in the art. In particular, the rotor (250) of each gyroscope assembly (240, 242) has a moment of inertia (also referred to as "rotational inertia") determined by a mass and a radius of the rotor (250). For versions of rotor (250) having a majority of its mass concentrated within ring portion (272), the moment of inertia (I) of rotor (250) may be approximated based on the radius (R) and mass (M) of ring portion (272), as follows:

$$I = MR^2$$

When rotor (250) is rotated by motor (246) about the respective spin axis (SA1, SA2) at a spin speed ($\omega_s$), rotor (250) has an angular momentum (K), as follows:

$$K = I \times \omega_s$$

An external torque (e.g., due to gravity) applied to gyroscopic stabilizer (210) induces precession of each gyroscope assembly (240, 242), and specifically gimbal (244), relative to frame (212) about its respective precession axis (PA1, PA2) at a precession rate ($\omega_p$). Precession rate ($\omega_p$) refers to rate at which a gimbal (244), and thus the respective gyroscope assembly (240, 242), pivots relative to frame (212) about the respective precession axis (PA1, PA2).

Precession rate ($\omega_p$) and angular momentum (K) cooperate to generate a gyroscopic torque ($\tau_{gyro}$) acting in the respective torque plane (TP1, TP2), as follows:

$$\tau_{gyro}=\omega_p \times K$$

As noted above, a component of the gyroscopic torque ($\tau_{gyro}$) is a stabilization torque ($\tau_{stab}$) configured to counteract an external torque applied to gyroscopic stabilizer (210). Stabilization torque ($\tau_{stab}$) may be quantified as a function of a precession angle ($\alpha_p$) assumed by a gyroscope assembly (240, 242) in a fully precessed state. More specifically, precession angle ($\alpha_p$) refers to an angular orientation of gimbal (244) relative to the respective stabilizer frame ring member (230, 232) and about the respective precession axis (PA1, PA2) when the respective gyroscope assembly (240, 242) is in a fully precessed state. Stabilization torque ($\tau_{stab}$) may be expressed as follows:

$$\tau_{stab}=\tau_{gyro}\times \sin(\alpha_p)$$

As described briefly above, gyroscopic stabilizer (210) may be employed to stabilize a variety of surgical instrument types, such as the laparoscopic surgical instrument (290) shown in FIG. 13B, in combination with or independently of a cannula assembly (12, 112). In that regard, and as shown in FIG. 14, gyroscope stabilizer (210) may further include a locking mechanism (294) (shown schematically) configured to releasably and frictionally engage an elongate shaft (292) of surgical instrument (290) to inhibit relative movement between gyroscopic stabilizer (210) and surgical instrument (290). Locking mechanism (294) of the present version is shown disposed on a side portion of collar (218), though it will be appreciated that locking mechanism (294) may be disposed on various other portions of stabilizer frame (212) in other versions. Locking mechanism (294) may include one or more clamping features and/or various other suitable frictional engagement features readily apparent to those of ordinary skill in the art in view of the teachings herein.

C. Exemplary Gyroscopic Surgical Instrument Stabilization System with Centralized Control and Related Sensor and Control Features As described above, gyroscopic stabilizer (210) may include one or more switches (not shown) actuatable by a user to selectively energize and deenergize motors (246) of gyroscope assemblies (240, 242) and thereby activate (i.e., power) and deactivate (i.e., depower) the stabilization function of gyroscopic stabilizer (210). In some instances, it may be desirable to provide more advanced levels of control over the function of gyroscopic stabilizer (210).

Figure 15:
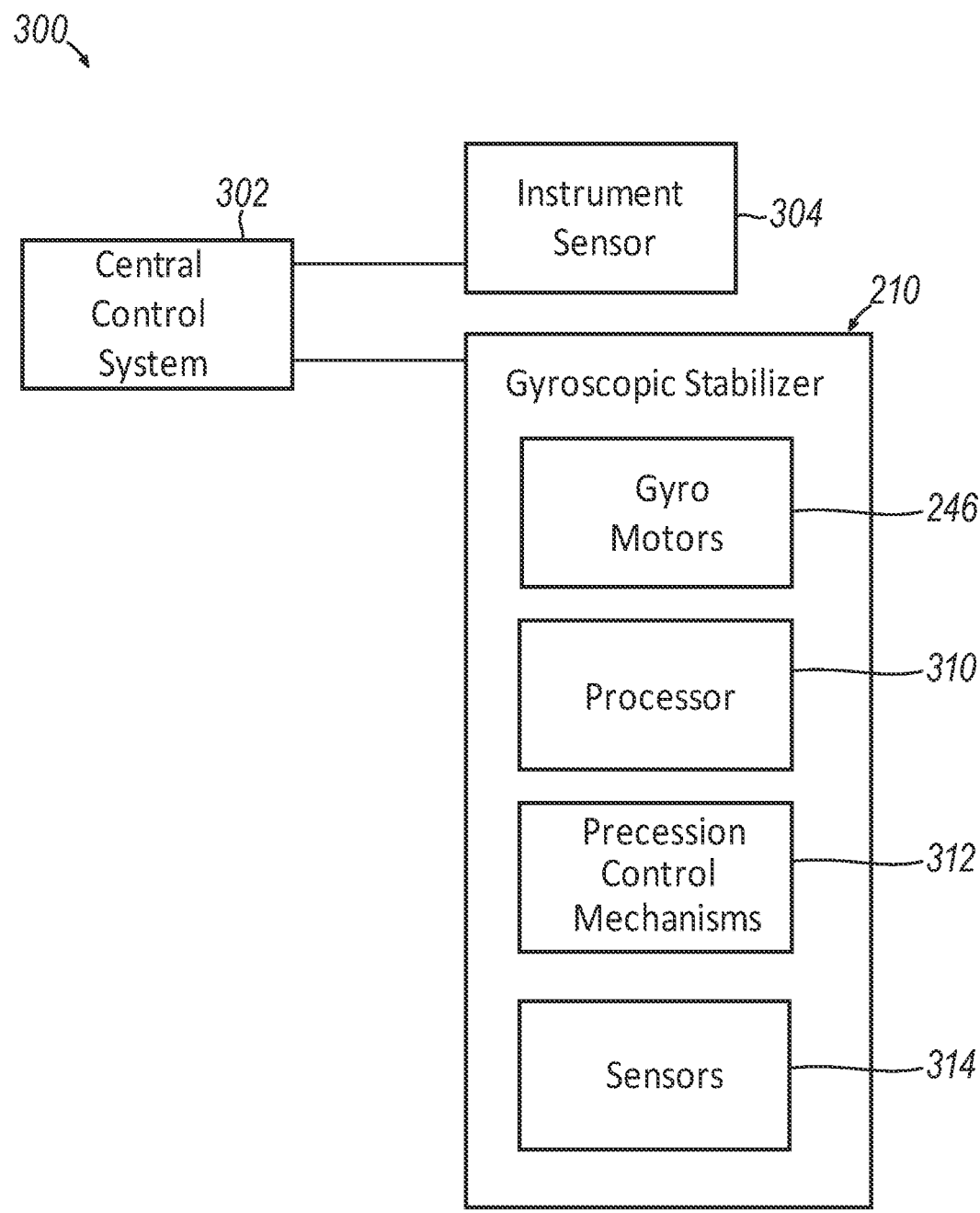
FIG. 15 depicts a schematic view of an exemplary gyroscopic surgical instrument stabilization system.

FIG. 15 shows an exemplary gyroscopic surgical instrument stabilization system (300) that includes a central control system (302) (also referred to as a "mantle"), an optional surgical instrument sensor (304) in communication with central control system (302), and an exemplary variation of gyroscopic stabilizer (210) in communication with central control system (302), with each of the system components being arranged separately from one another. The communication between central control system (302) and gyroscopic stabilizer (210), and between central control system (302) and instrument sensor (304), may be provided by respective wireless connections, such as Bluetooth. Alternatively, one or more wired connections may be used.

As shown schematically, gyroscopic stabilizer (210) includes gyroscope assembly motors (246), a processor (310), one or more precession control mechanisms (312), and one or more sensors (314). Each precession control mechanism (312) is configured to control the precession rate and/or precession angle of a respective gyroscope assembly (240, 242). For instance, each precession control mechanism (312) may be in the form of a precession axis brake operable to brake precession speed of the respective gyroscope assembly (240, 242), or a servo motor operable to provide active precession control of a respective gyroscope assembly (240, 242), for example as described in greater detail below in connection with FIG. 26. By way of example only, stabilizer sensors (314) may include an accelerometer for sensing linear acceleration of gyroscopic stabilizer (210) and a gyroscope sensor for sensing angular orientation of gyroscopic stabilizer (210). Processor (310) is operable to communicate with motors (246), precession control mechanisms (312), sensors (314), and central control system (302).

Central control system (302) may be configured selectively toggle stabilizer (210) between a "clutched" mode and an "unclutched" mode depending on certain conditions. In the "clutched" mode, gyroscope assemblies (240, 242) of stabilizer (210) are free to precess about precession axes (PA1, PA2) without restriction and thus generate maximum stabilization torques to counteract external torques applied to stabilizer (210). As a result, stabilizer (210) is maintained in the most recent user-defined angular orientation relative to a patient such that the surgical instrument with which stabilizer (210) is coupled may be disengaged by the surgeon without tipping over. Advantageously, this enables the surgeon to safely perform other surgical tasks without having to manually maintain or otherwise monitor the angular orientation of the surgical instrument. In the "unclutched" mode, gyroscope assemblies (240, 242) are controlled to generate less stabilization torque and thereby permit a surgeon to more easily reorient stabilizer (210), for example while manipulating a surgical instrument to which stabilizer (210) is attached. However, gyroscope assemblies (240, 242) may still remain active enough in the unclutched mode to effectively eliminate the weight component of stabilizer (210) as would otherwise be sensed by the surgeon. As described in greater detail below, such limitation of stabilization torque output in the unclutched mode may be achieved by limiting the precession rate of one or both gyroscope assemblies (240, 242) relative to stabilizer frame (212), and/or limiting a rotational speed of one or both motors (246) and thus a spin speed of the respective rotor (250) about spin axes (SA1, SA2).

Figure 16:
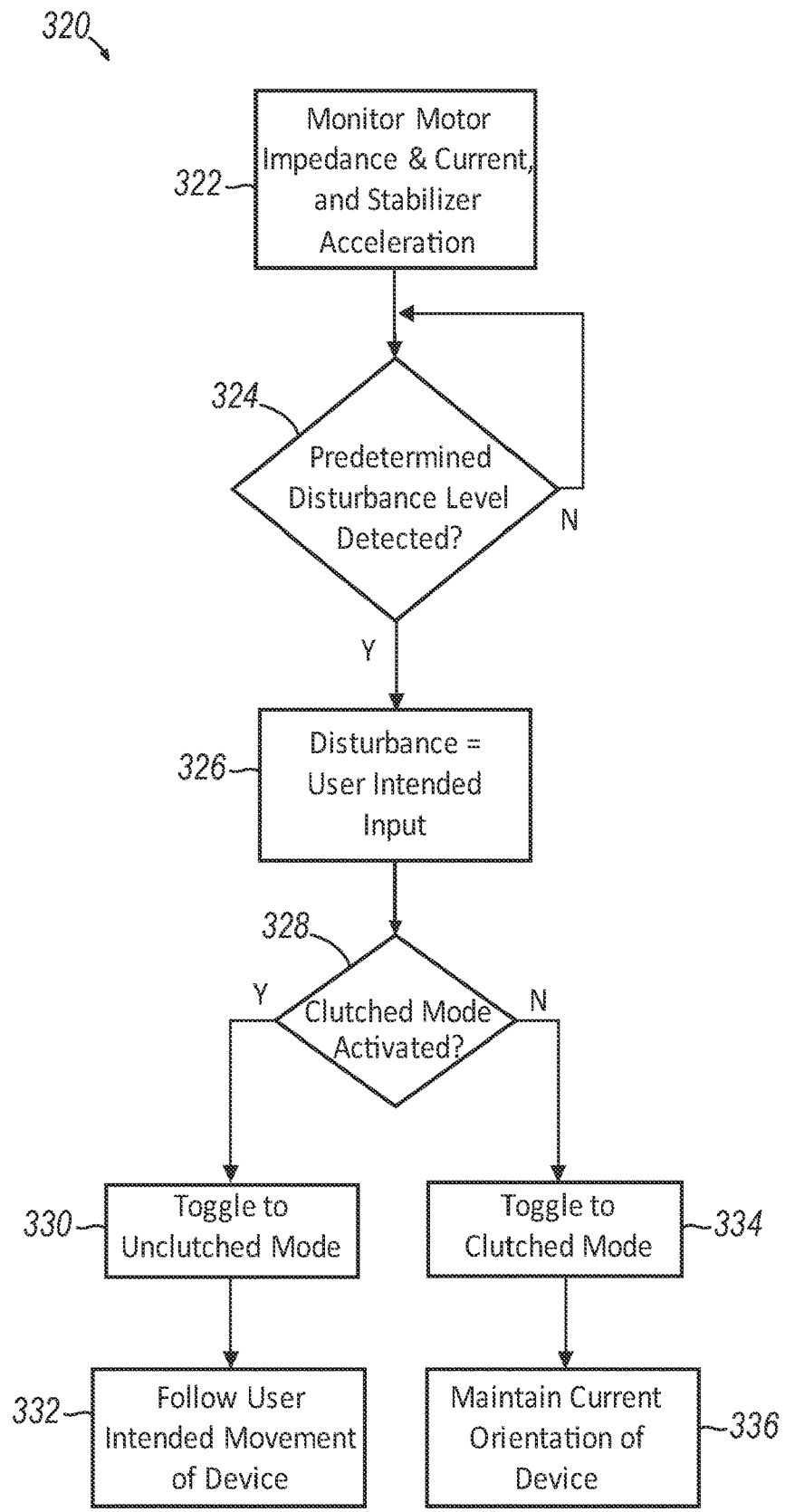
FIG. 16 depicts a diagrammatic view of an exemplary method of controlling the gyroscopic stabilizer of FIG. 6 as a component of the gyroscopic surgical instrument stabilization system of FIG. 15.

FIG. 16 shows an exemplary method (320) of controlling gyroscopic stabilizer (210) with central control system (302) of gyroscopic surgical instrument stabilization system (300) to toggle between the clutched mode and the unclutched mode. At step (322), central control system (302) monitors the electrical impedance and current drawn by motors (246), as well as a linear acceleration of stabilizer (210) as measured by sensor (314). At step (324), central control system (302) evaluates whether a predetermined level of disturbance has been detected in any of the monitored conditions of step (322). If "no" at step (324), control system (302) continues to monitor for such a disturbance. If "yes" at step (324), central control system (302) determines at step (326) that the detected disturbance is the result of a user-intended input applied to stabilizer (210), such that stabilizer (210) should be toggled from its current clutched/unclutched state, to the opposite unclutched/clutched state. By way of example only, the predetermined levels of disturbance may be selected to correspond to a user-intended movement in the form of a user tapping a portion of stabilizer (210) or the surgical instrument coupled with stabilizer (210), or sliding a surgical instrument longitudinally through stabilizer (210) and a trocar cannula assembly to which stabilizer (210) is attached.

At step (328), central control system (302) evaluates whether gyroscopic stabilizer (210) is currently in the clutched mode. If "yes" at step (328), then control system (302) toggles stabilizer (210) to the unclutched mode at step (330), and stabilizer (210) permits user-intended input movements at step (332). If "no" at step (328), meaning that stabilizer (210) is in the unclutched mode, then control system (302) toggles stabilizer (210) to the clutched mode at step (336), and stabilizer (210) maintains its current user-defined angular orientation at step (336).

Figure 17:
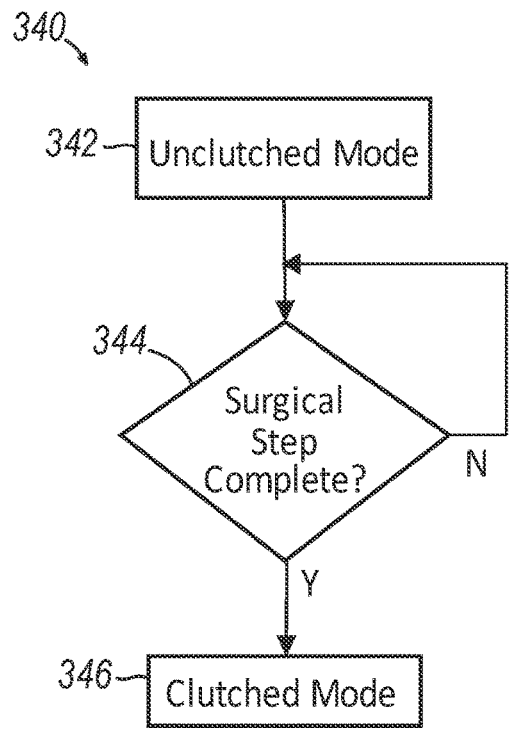
FIG. 17 depicts a diagrammatic view of another exemplary method of controlling the gyroscopic stabilizer of FIG. 6 as a component of the gyroscopic surgical instrument stabilization system of FIG. 15.

FIG. 17 shows another exemplary method (340) of controlling gyroscopic stabilizer (210) with central control system (302) of gyroscopic surgical instrument stabilization system (300). At step (342), central control system (302) places stabilizer (210) in the unclutched mode such that the surgical instrument with which stabilizer (210) is coupled may be easily manipulated by a surgeon for performing a surgical step. At step (344), control system (302) evaluates whether the surgical step is complete based on readings provided by stabilizer sensors (314) and/or instrument sensor (304). If "no" at step (344), control system (302) maintains stabilizer (210) in the unclutched mode and continues to monitor for whether the surgical step is complete. If "yes" at step (344), control system (302) toggles stabilizer (210) into the clutched mode at step (346) so that stabilizer (210) maintains its most recent user-defined angular orientation relative to the patient.

Figure 18:
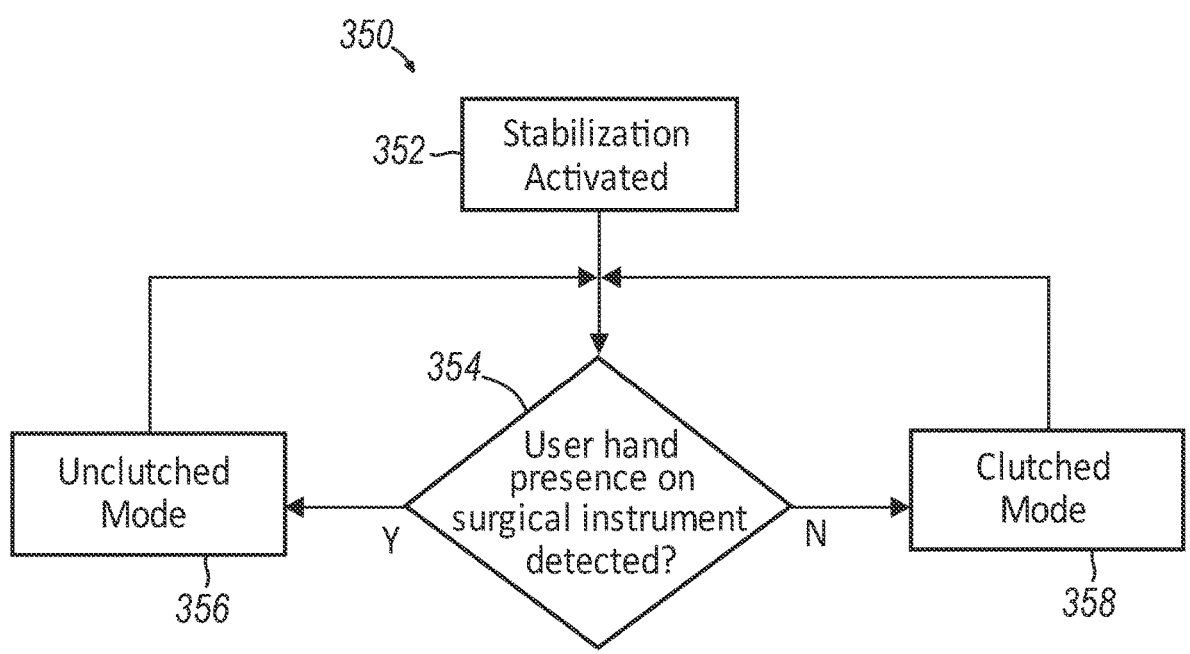
FIG. 18 depicts a diagrammatic view of another exemplary method of controlling the gyroscopic stabilizer of FIG. 6 as a component of the gyroscopic surgical instrument stabilization system of FIG. 15.

FIG. 18 shows yet another exemplary method (350) of controlling gyroscopic stabilizer (210) with central control system (302) of gyroscopic surgical instrument stabilization system (300). At step (352), gyroscope assemblies (240, 242) are activated, either manually by a user or automatically by control system (302) in response to detection of an environmental condition, so that motors (246) rotate rotors (250) to generate gyroscopic torque. Once activated, gyroscopic stabilizer (210) may default to the clutched mode to maintain its current angular orientation relative to a patient. At step (354), control system (302) evaluates via instrument sensor (304) whether a surgeon's hand has engaged the surgical instrument with which stabilizer (210) is coupled. If "yes" at step (354), control system (302) places or otherwise maintains stabilizer (210) in the unclutched mode at step (356). If "no" at step (354), control system (302) places or otherwise maintains stabilizer (210) in the clutched mode at step (358). After completing one of steps (356, 358), control system (302) returns to step (354) to monitor for the presence of a surgeon's hand on the surgical instrument and then act accordingly in a continuous loop while stabilizer (210) remains activated.

Figure 19:
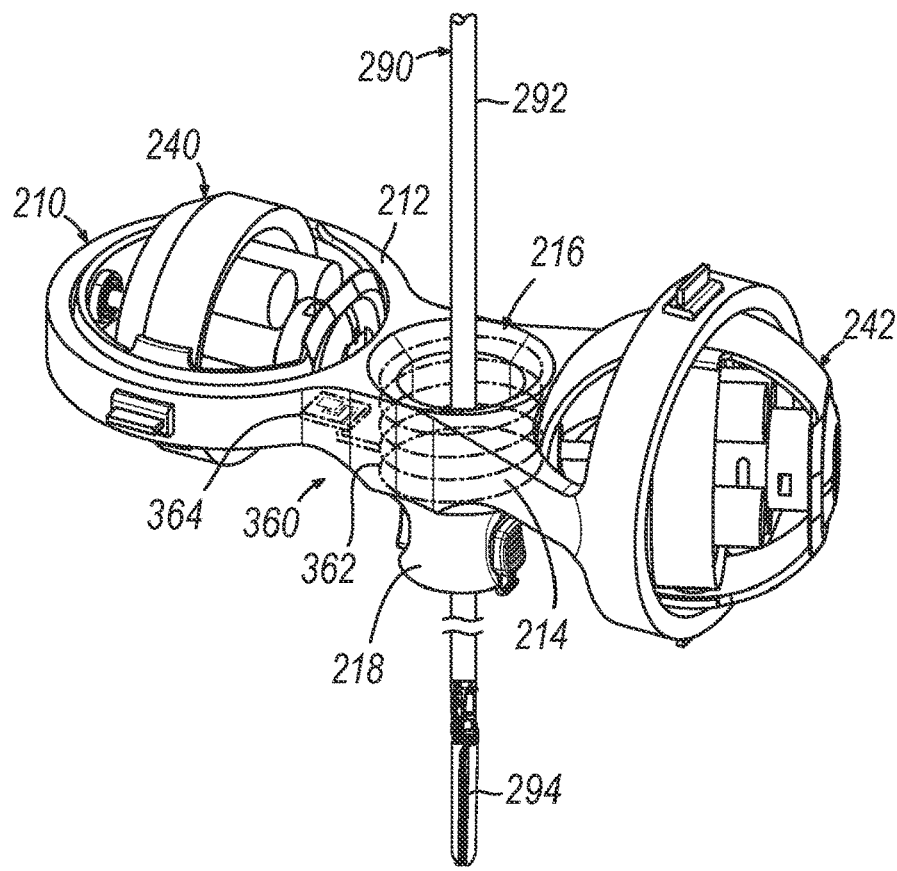
FIG. 19 depicts a perspective view of another exemplary gyroscopic stabilizer in combination with the second surgical instrument of FIG. 13B, showing a surgical instrument detection sensor assembly of the gyroscopic stabilizer in phantom.
Figure 20:
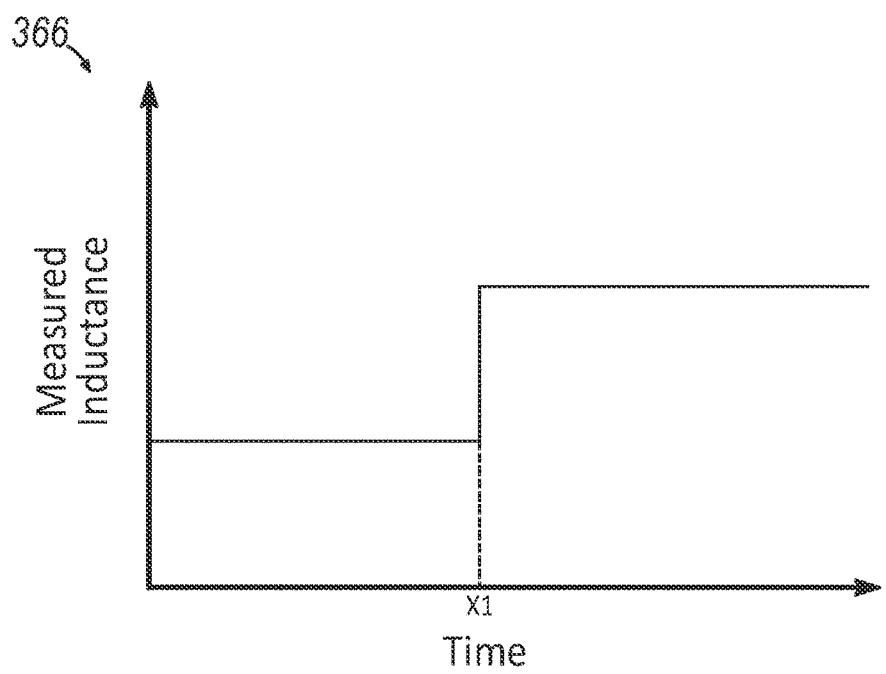
FIG. 20 depicts an exemplary line graph showing a measured electrical impedance of the surgical instrument detection sensor of FIG. 19 over time.

FIG. 19 shows another exemplary variation of gyroscopic stabilizer (210) in which stabilizer (210) includes a surgical instrument detection sensor assembly (360) having an inductive instrument detection sensor in the form of a wire coil (362) coupled with a printed circuit board assembly (364) housed within stabilizer frame (212). More specifically, wire coil (362) is embedded within a cylindrical sidewall of hub (214) that surrounds central passage (216), such that wire coil (362) encircles the central axis (CA) of frame (212). Sensor assembly (360) is configured to detect, via electromagnetic induction, a sudden presence or absence of a surgical instrument (290) within central passage (216). For instance, as illustrated by the exemplary graph (366) in FIG. 20, an inductance of wire coil (362) as measured by circuit board assembly (364) increases at time (X1) when surgical instrument (290) is directed distally through central passage (216) of stabilizer (210). This change in inductance is communicated as a signal to central control system (302), which may then act in response. For example, control system (302) may activate or deactivate gyroscope assemblies (240, 242), or toggle stabilizer (210) between the clutched and unclutched modes.

Figure 21:
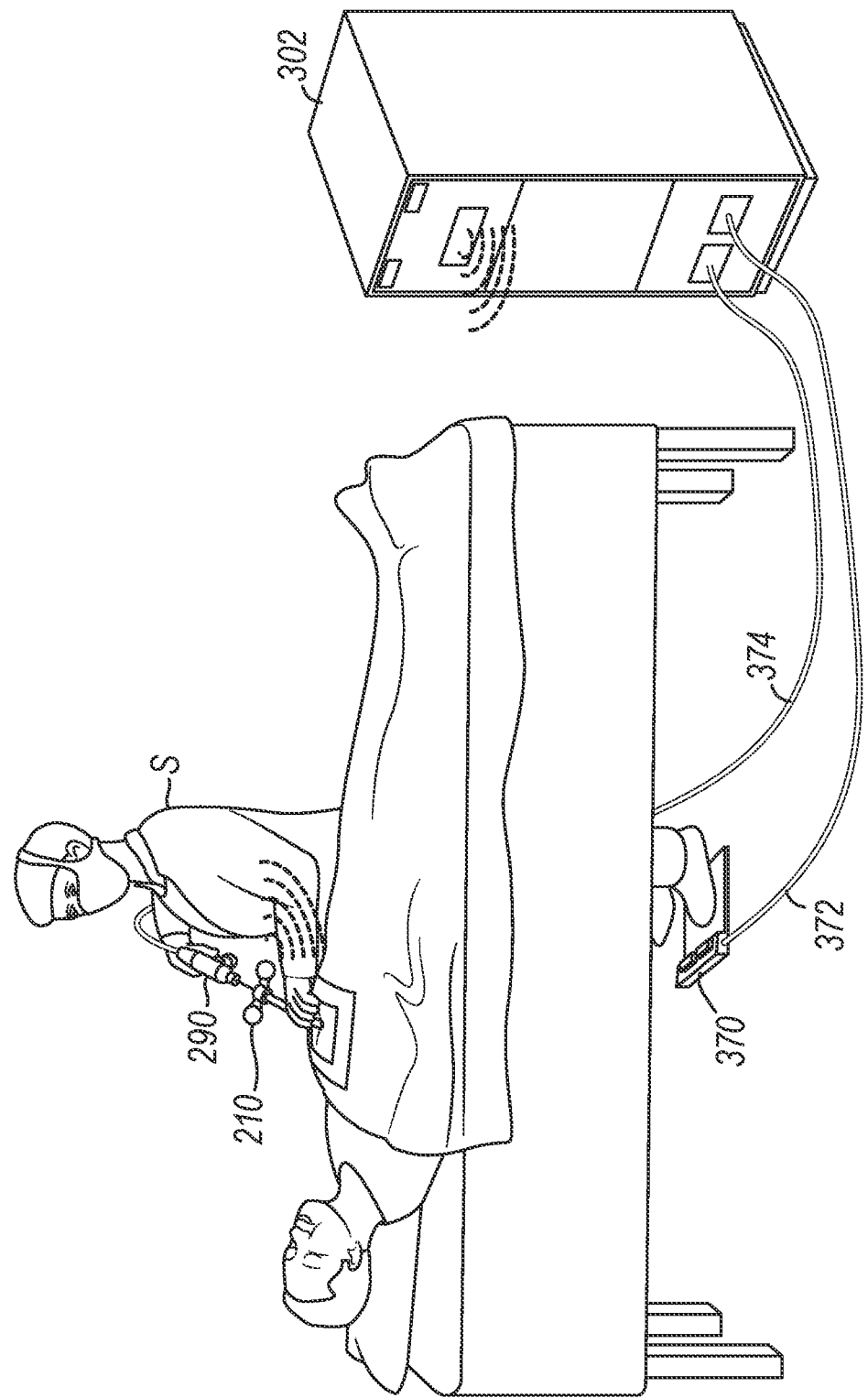
FIG. 21 depicts a schematic perspective view of an exemplary version of the gyroscopic surgical instrument stabilization system of FIG. 15, shown having a surgeon detection mechanism.

FIG. 21 shows an exemplary variation of gyroscopic surgical instrument stabilization system (300), in which system (300) further includes a foot pedal device (370) coupled with central control system (302) via a first cable (372). Gyroscopic stabilizer (210) is shown mounted to an exemplary laparoscopic surgical instrument (290), which is coupled with central control system (302) via a second cable (374) that may provide power to surgical instrument (290) as well as communication between surgical instrument (290) and control system. Gyroscopic stabilizer (210) is shown in wireless communication with control system (302). Food pedal device (370) is selectively actuatable by the foot of a surgeon (S) to indicate to control system (302) the surgeon's presence at the operating table (376). Control system (302) may control gyroscopic stabilizer (210) according to one or more predetermined algorithms based on the presence or absence of surgeon (S) as indicated by a signal provided to control system (302) by foot pedal device (370). For instance, upon detecting the presence of surgeon (S) at operating table (376) via foot pedal device (370), control system (302) may automatically activate stabilizer (210). Conversely, upon detecting the absence of surgeon (S) at operating table (376) via foot pedal device (370), control system (302) may automatically deactivate stabilizer (210).

Figures 22, 23:
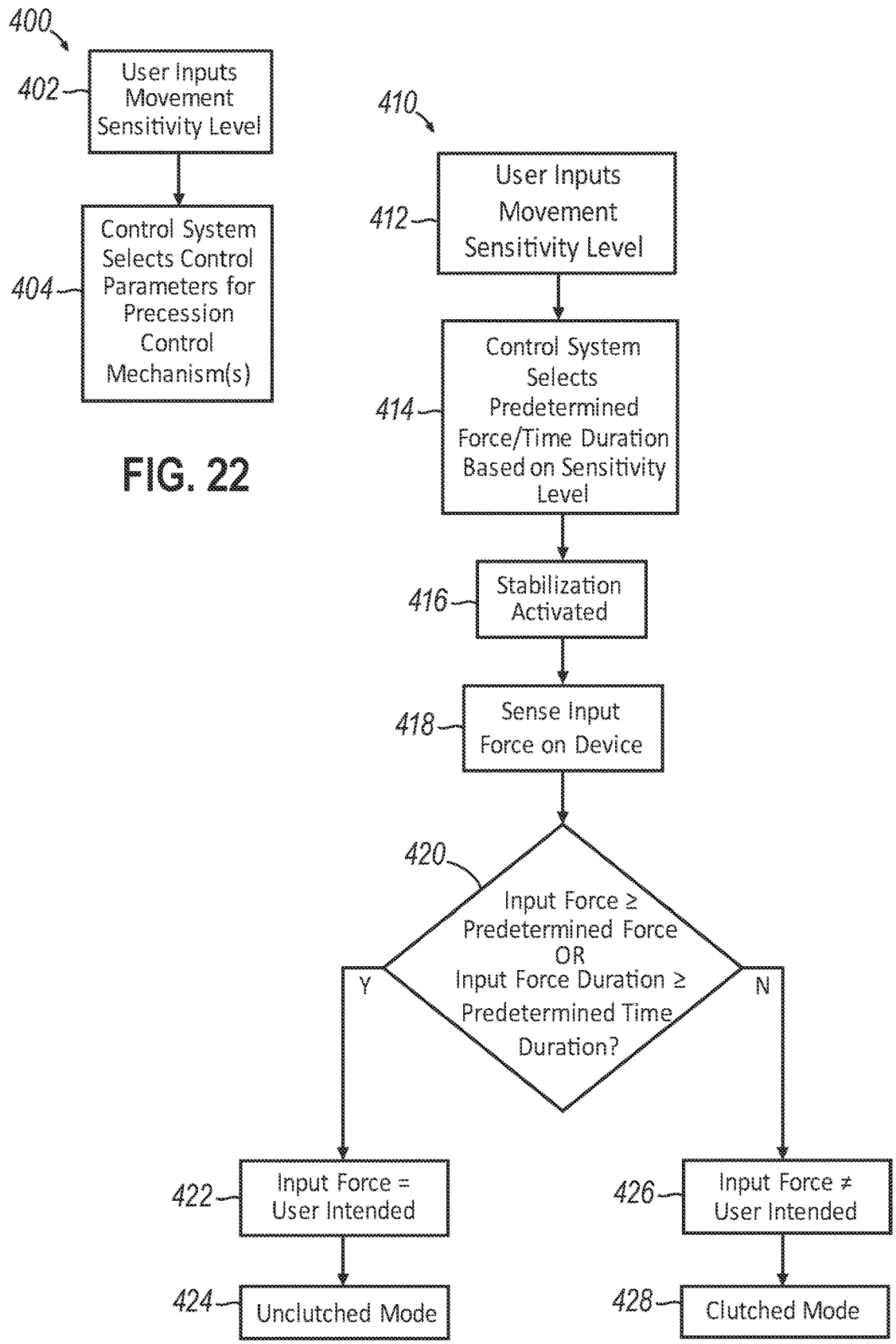
FIG. 22 depicts a diagrammatic view of another exemplary method of controlling the gyroscopic stabilizer of FIG. 6 as a component of the gyroscopic surgical instrument stabilization system of FIG. 15.
FIG. 23 depicts a diagrammatic view of another exemplary method of controlling the gyroscopic stabilizer of FIG. 6 as a component of the gyroscopic surgical instrument stabilization system of FIG. 15.

In some instances, it may desirable to provide a user with the ability to vary the magnitude and/or duration of a predetermined force effective to trigger control system (302) to toggle gyroscopic stabilizer (210) between the clutched and unclutched modes in response to application of the predetermined force (e.g., by a surgeon) to stabilizer (210) or to a surgical instrument with which stabilizer (210) is coupled. FIGS. 22 and 23 show exemplary methods (400, 410) of controlling gyroscopic stabilizer (210) with central control system (302) in such a manner.

FIG. 22 illustrates simplified method (400), in which a user inputs a desired movement sensitively level to central control system (302) at step (402), for example via a graphical user interface or other user input feature (not shown) that communicates with control system (302). The input movement sensitivity level indicates at least one of a minimum magnitude or a minimum duration of the predetermined force effective to trigger control system (302) to toggle gyroscopic stabilizer (210) between the clutched and unclutched modes in response to application of the predetermined force (e.g., by a surgeon) to stabilizer (210) or a corresponding surgical instrument, for example as sensed by instrument sensor (304) and/or stabilizer sensors (314). At step (404), control system (302) then selects one or more suitable parameters for controlling gyroscopic stabilizer (210) based on the movement sensitivity level input by the user.

FIG. 23 shows method (410) in the form of an exemplary detailed variation of method (400). At step (412) of method (410), a user inputs a desired movement sensitively level into central control system (302). Based on the input sensitivity level, at step (414) control system (302) selects a minimum input force magnitude and/or a minimum input force time duration. Control system (302) then activates (i.e., powers) gyroscopic stabilizer (210) at step (416). At step (418), control system (302) senses an input force applied to gyroscopic stabilizer (210) and/or to the surgical instrument with which stabilizer (210) is coupled. It will be appreciated that the sensed input force may be the result of contact with one or more of a variety of structures, such as the surgeon or the patient, for example.

At step (420) of method (410), control system (302) evaluates the sensed input force relative to the minimum input force magnitude and the minimum input force time duration selected in step (414) to determine whether the input force was a user-intended input force, and thus whether control system (302) should provide gyroscopic stabilizer (210) in the clutched or unclutched mode. More specifically, control system (302) evaluates at step (420) if a magnitude of the sensed input force is greater than or equal to the minimum input force magnitude, and/or if a time duration of the sensed input force is greater than or equal to the minimum input force time duration. If "yes" at step (420), control system (302) determines at step (422) that the sensed input force was in fact a user-intended input force, and thus control system (302) proceeds to place gyroscopic stabilizer (210) in the unclutched mode at step (424) so that that a surgeon may easily manipulate the surgical instrument(s) to which stabilizer (210) is attached. If "no" at step (420), control system (302) determines at step (426) that the sensed input force was not a user-intended force, such as an unintended user input force caused by accidental bumping of stabilizer (210) or the corresponding surgical instrument(s). As a result, control system (302) places stabilizer (210) in, or otherwise directs stabilizer (210) to maintain, the clutched mode at step (428) so that stabilizer (210) maintains a user-defined angular orientation relative to the patient while the surgeon performs other surgical tasks not involving the surgical instrument(s) with which stabilizer (210) is coupled.

Figure 24:
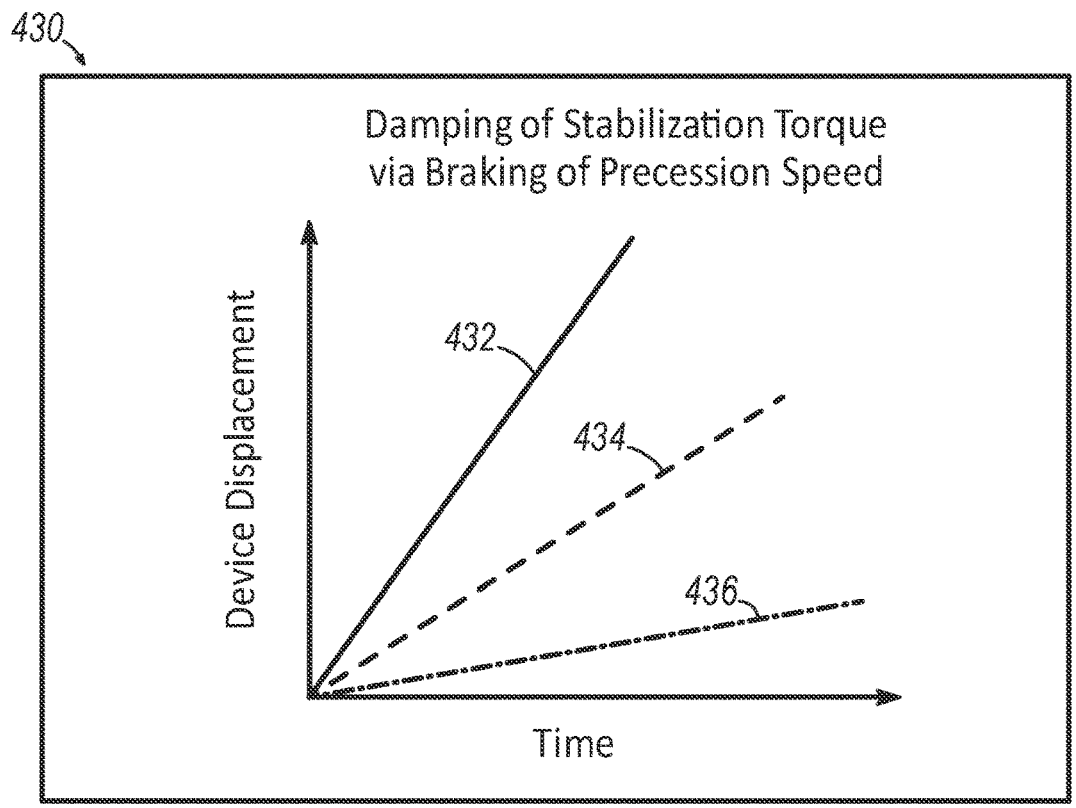
FIG. 24 depicts an exemplary line graph showing performance of the gyroscopic stabilizer of FIG. 6 according to an exemplary version of the method of FIG. 22.
Figure 25:
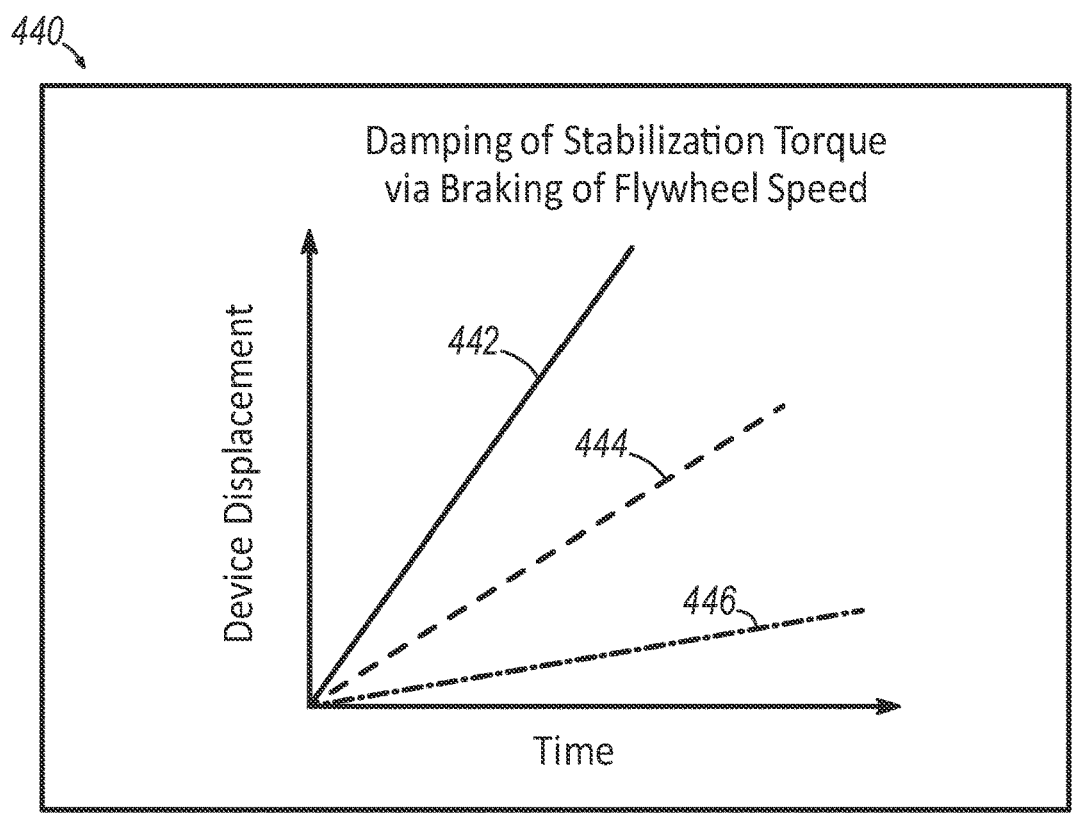
FIG. 25 depicts an exemplary line graph showing performance of the gyroscopic stabilizer of FIG. 6 according to another exemplary version of the method of FIG. 22.

FIGS. 24 and 25 show line graphs (430, 440) illustrating exemplary positional displacement of gyroscopic stabilizer (210) relative to a patient over time in response to a constant external input force applied to stabilizer (210) and/or to the surgical instrument securely attached to stabilizer (210) (e.g., cannula assembly (112)), and when various input movement sensitivity levels are specified by a user. In general, it will be understood that a particular input movement sensitivity level specified by the user may dictate the input force conditions under which stabilizer (210) may toggle between the clutched mode and the unclutched mode; or alternatively, dictate a maximum magnitude of stabilization torque permitted to be generated by gyroscope assemblies (240, 242) when in the unclutched mode. The exemplary curves of line graphs (430, 440) illustrate the latter scenario.

As shown in FIG. 24, graph (430) illustrates exemplary device displacement during damping of stabilization torque generated by gyroscope assemblies (240, 242) in the unclutched mode, via braking of the rate at which gyroscope assemblies (240, 242) are permitted to precess (i.e., pivot) relative to stabilizer frame (212) about precession axes (PA1, PA2). Curve (432) represents a relatively high input movement sensitivity level that yields approximately 80% braking of the precession rate. Curve (434) represents a lower input movement sensitivity level that yields approximately 40% braking of the precession rate. Curve (436) represents an even lower input movement sensitivity level that yields approximately 10% braking of the precession rate. The x-axis represents the lowest possible input movement sensitivity level that yields 0% braking of the precession rate.

As shown in FIG. 25, graph (440) illustrates exemplary device displacement during damping of stabilization torque generated by gyroscope assemblies (240, 242) in the unclutched mode, via braking of the speed at which rotors (250) (or "flywheel") spin about spin axes (SA1, SA2). Curve (442) represents a relatively high input movement sensitivity level that yields approximately 80% braking of the rotor spin rate. Curve (444) represents a lower input movement sensitivity level that yields approximately 40% braking of the rotor spin rate. Curve (446) represents an even lower input movement sensitivity level that yields approximately 10% braking of the rotor spin rate. The x-axis represents the lowest possible input movement sensitivity level that yields 0% braking of the rotor spin rate.

In configurations in which one or both gyroscope assemblies (240, 242) includes a braking mechanism for breaking a spin rate of rotor (250), such braking may be accomplished via regenerative braking rather than frictional braking. For instance, a motor (246) may be rotated in an opposite direction to thereby absorb mechanical energy from the rotating rotor (250), thus minimizing mechanical wear of device components and maximizing available run time of motors (246).

Figure 26:
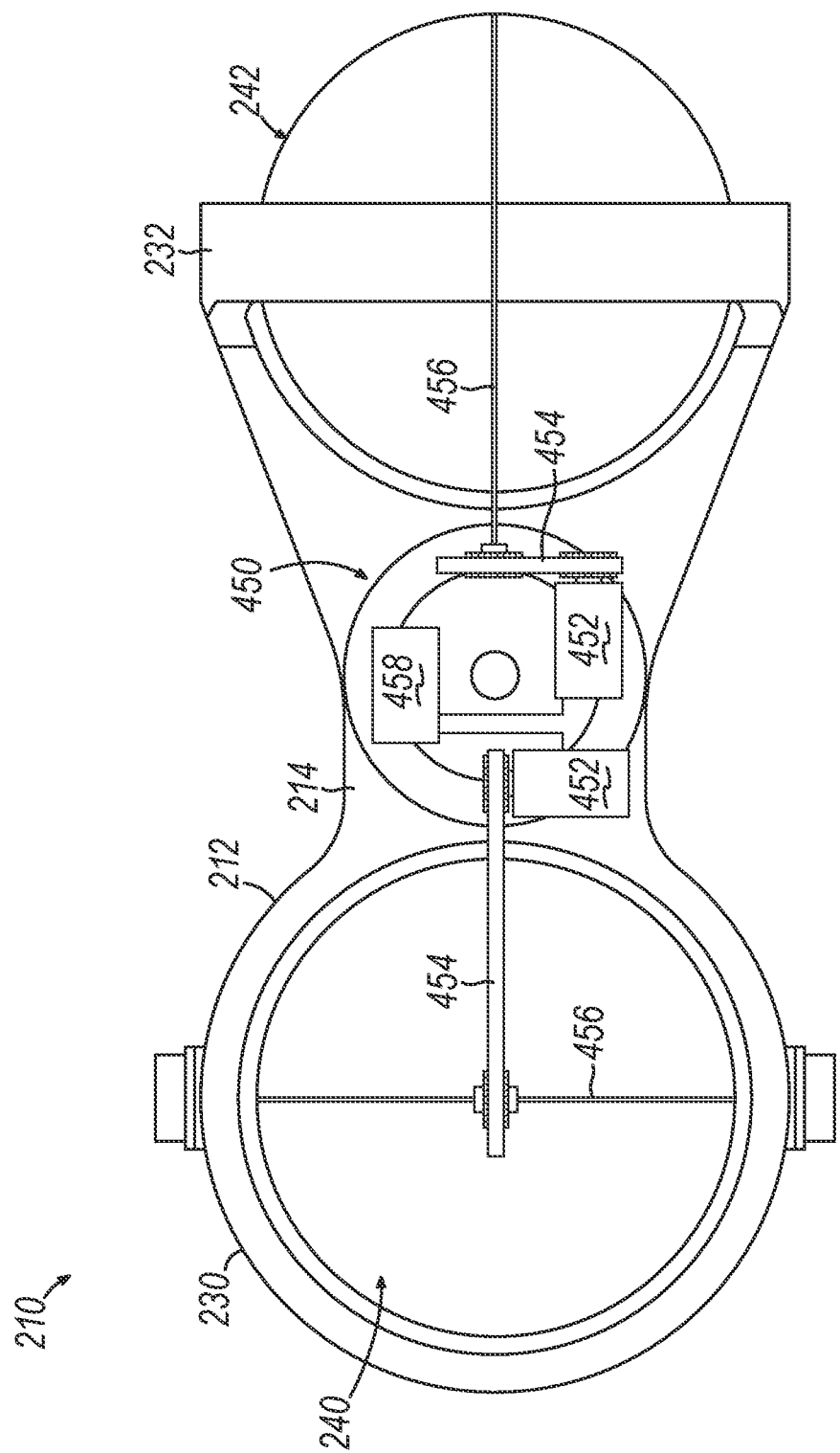
FIG. 26 depicts a schematic top plan view of another exemplary gyroscopic stabilizer having first and second precession control mechanisms.

FIG. 26 shows an exemplary version of gyroscopic stabilizer (210) that includes an active precession control mechanism (450) coupled with each gyroscope assembly (240, 242) (shown schematically). Each active precession control mechanism (450) includes a servo motor (452) and a belt (454) that couples servo motor (452) with a rotatable member (456) that extends along at least a portion of the respective precession axis (PA1, PA2). Mechanism (450) communicates with a printed circuit board assembly (458) that may incorporate processor (310) and stabilizer sensors (314), and which may communicate directly with central control system (302). Each servo motor (452) is operable to rotate the respective rotatable member (456) via the respective belt (454) at a precession rate dictated by either circuit board assembly (458) or central control system (302). Each servo motor (452) is further operable to rotate the respective rotatable member (456) so that the respective gyroscope assembly (240, 242) assumes and maintains a selected angular orientation, as dictated by either circuit board assembly (458) or central control system (302). This configuration provides active control over the magnitude and direction of stabilization torque generated by gyroscope assemblies (240, 242).

Figure 27:
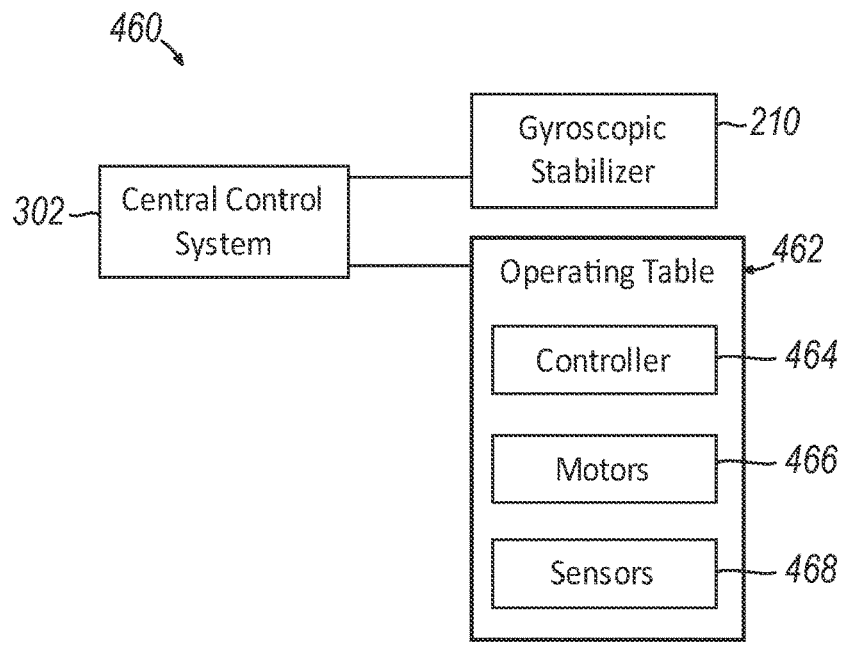
FIG. 27 depicts a schematic view of another exemplary gyroscopic surgical instrument stabilization system that includes an electric operating table.

FIG. 27 shows another exemplary gyroscopic surgical instrument stabilization system (460) having central control system (302), gyroscopic stabilizer (210), and an electric operating table (462). As shown schematically, operating table (462) may include a controller (464), one or more motors (466) operable to actuate operating table (462) between a plurality of positions, and one or more sensors (468). Operating table controller (464) communicates with central control system (302) via a wireless or wired connection.

Figure 28:
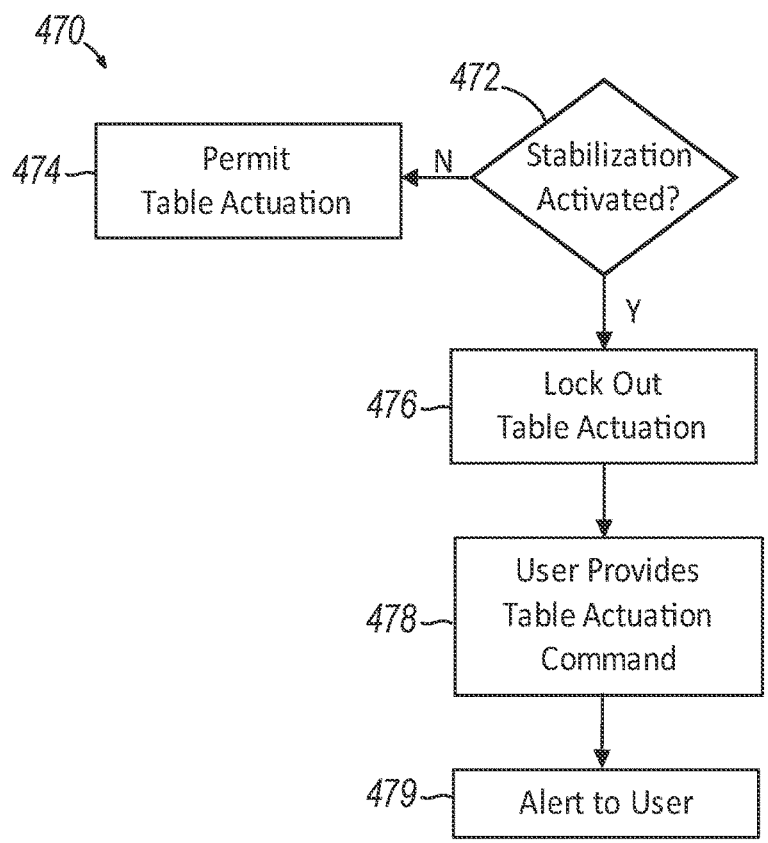
FIG. 28 depicts a diagrammatic view of an exemplary method of controlling the electric operating table of the system of FIG. 27.

FIG. 28 shows an exemplary method (470) of controlling electric operating table (462) with central control system (302). At step (472), control system (302) evaluates whether gyroscopic stabilizer (210) is currently activated in connection with a patient located on operating table (462). If "no" at step (472), control system (302) permits operating table (462) to be actuated to a new position at step (474). If "yes" at step (472), control system (302) inhibits actuation of operating table (462) at step (476). Accordingly, when a user provides a table actuation command at step (478), control system (302) provides an alert to the user at step (479) that gyroscopic stabilizer (210) is currently activated. This manner of controlling operating table (462) ensures that operating table (462) does not interfere with surgical instrument stabilization provided by gyroscopic stabilizer (210).

Figure 29:
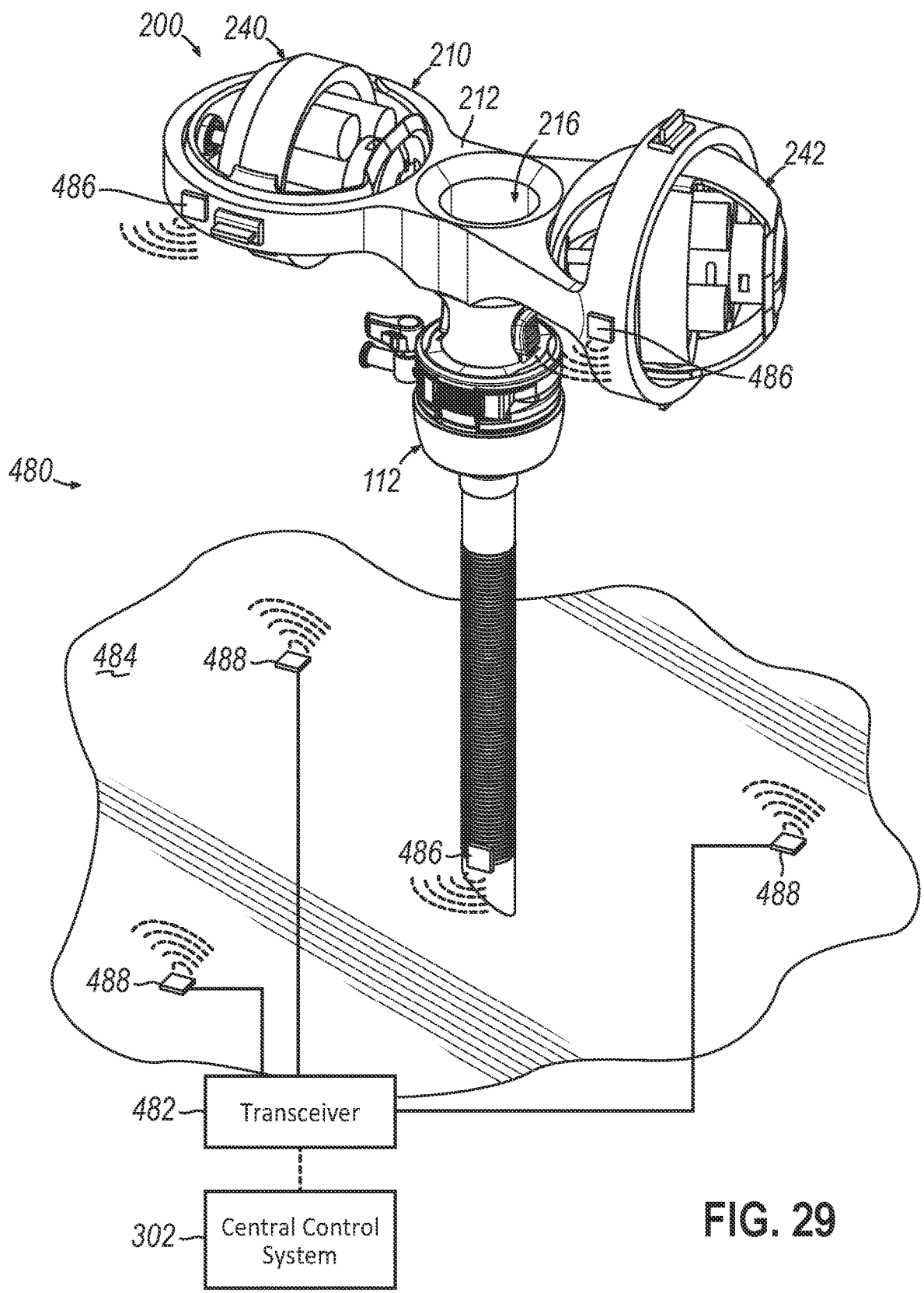
FIG. 29 depicts a schematic perspective view of another exemplary gyroscopic surgical instrument stabilization system that includes a plurality of position sensors.

FIG. 29 shows another exemplary gyroscopic surgical instrument stabilization system (480), which includes gyroscopic surgical instrument assembly (200), central control system (302), and a transceiver (482) in communication with central control system (302) via a wireless connection, such as Bluetooth. System (480) is configured to monitor and adjust an angular orientation (i.e., tilt) of gyroscopic surgical instrument assembly (200) relative to an operating table (484) to maintain a relative orientation therebetween when operating table (484) is repositioned. Operating table (484) may be similar to operating table (462) described above. In the present example, at least three plurality of trackable elements (486) (shown schematically) are coupled to gyroscopic stabilizer (210) and to cannula assembly (112). Specifically, in the present version, a first trackable element (486) is coupled to first ring member (230) of stabilizer frame (212); a second trackable element (486) is coupled to second ring member (232) of stabilizer frame (212); and a third trackable element (486) is coupled to a distal end of cannula assembly (112). Trackable elements (486) are configured to communicate wirelessly with a corresponding at least three transceiver pads (488) arranged on operating table (484). Transceiver pads (448) are coupled to and communicate with transceiver (482) so that control system (302) may monitor a three-dimensional angular orientation (i.e., attitude) of gyroscopic surgical instrument assembly (200) relative to operating table (484). In other words, the exemplary arrangement of trackable elements (486) and transceiver pads (488) enables central control system (302) to determine the angular tilt of gyroscopic surgical instrument assembly (200) via triangulation.

Figure 30:
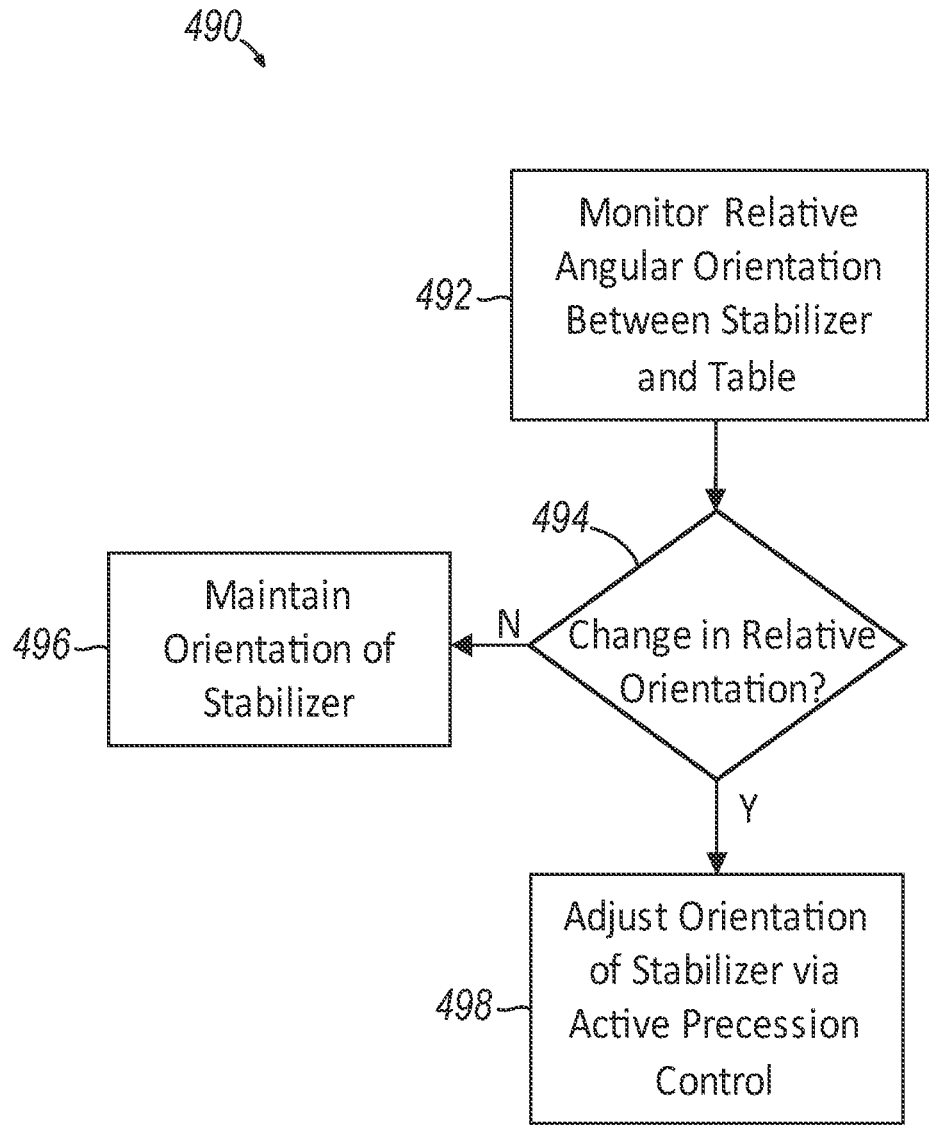
FIG. 30 depicts a diagrammatic view of an exemplary method of monitoring and adjusting an angular orientation of a gyroscopic surgical instrument assembly relative to an operating table of the system of FIG. 29.

FIG. 30 shows an exemplary method (490) of controlling gyroscopic stabilizer (210) with central control system (302) to maintain an angular orientation of gyroscopic surgical instrument assembly (200) relative to operating table (462). At step (492), control system (302) monitors a relative angular orientation between gyroscopic surgical instrument assembly (200) and operating table (484) based on the positional detection of trackable elements (486) by transceiver (482), via transceiver pads (488). At step (494), control system (302) evaluates if there has been a change in this relative angular orientation based on the positional data provided by transceiver (482). If "no" at step (494), control system (302) at step (496) controls gyroscopic stabilizer (210) to maintain the current angular orientation of gyroscopic surgical instrument assembly (200) relative to operating table (484). If "yes" at step (494), control system (302) at step (498) directs active precession control mechanism (450) of stabilizer (210) to vary the precession of gyroscope assemblies (240, 242) and thereby actively reorient gyroscopic surgical instrument assembly (200) to reassume and maintain the original angular orientation relative to operating table (484).

D. Exemplary Alternative Features for Safety and Compact Form of Gyroscopic Stabilizer In addition to various exemplary control features described above, it may be desirable to provide gyroscopic stabilizer (210) with additional or alternative features that promote safe operation and a compact configuration.

Figure 31A:
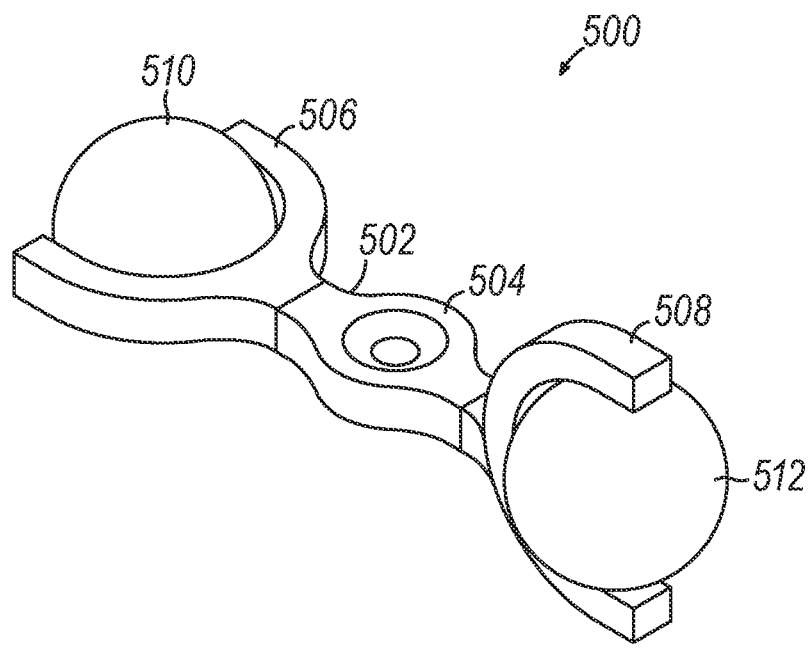
FIG. 31A depicts a schematic perspective view of another exemplary gyroscopic stabilizer having a frame with first and second gyroscope support members that are separable from a frame hub, showing the gyroscope support members attached to the frame hub.
Figure 31B:
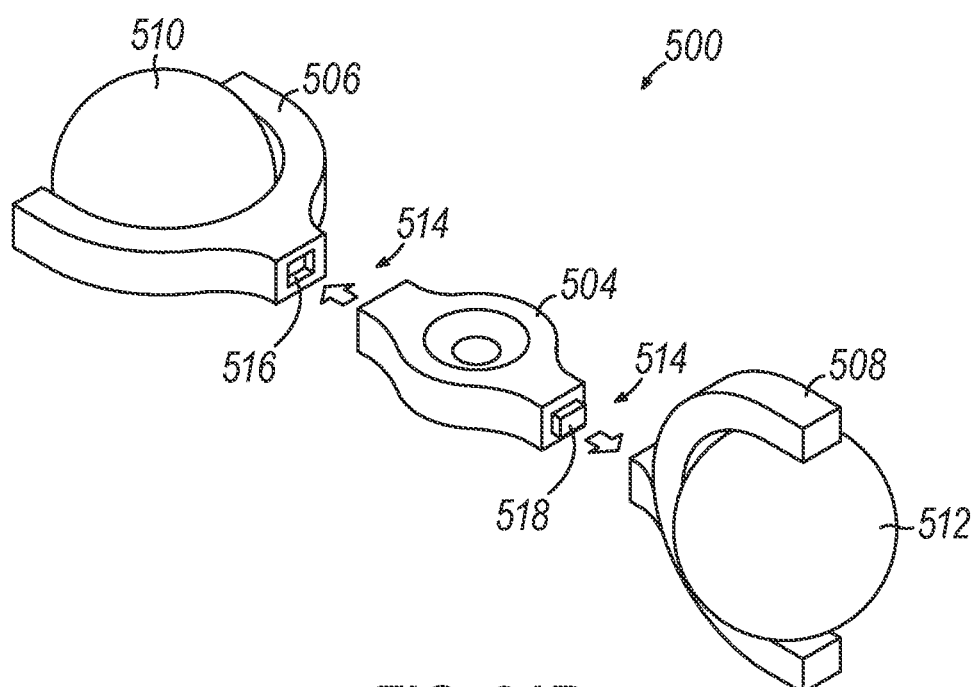
FIG. 31B depicts a schematic perspective view of the gyroscopic stabilizer of FIG. 31A, showing the first and second gyroscope support members being ejected outwardly from the frame hub.

FIGS. 31A-31B show another exemplary gyroscopic stabilizer (500) that is similar to gyroscopic stabilizer (210) described above except as otherwise described below. Stabilizer (500) includes a frame (502) having a central hub (504), a first gyroscope support member (506) and a second gyroscope support member (508) diametrically opposed from first gyroscope support member (506). A first gyroscope assembly (510) is pivotably supported by first gyroscope support member (506), and a second gyroscope assembly (512) is pivotably supported by second gyroscope support member (508).

Each gyroscope support member (506, 508) is releasably attached to hub (504) by a connection feature (514). Connection features (514) are configured to maintain a secure connection between each gyroscope support member (506, 508) and hub (504) under normal operating conditions of stabilizer (500). In an emergency stop situation, connection features (514) are configured to automatically release gyroscope support members (506, 508) from hub (504) so that gyroscope assemblies (510, 512) fall down to a floor and safely away from the surgeon and patient. Each connection feature (514) of the present version is shown including a recess (516) and a mating projection (518), though connection features (514) may take various other suitable forms in other versions, such as latches, magnets, and other functionally similar elements apparent to those of ordinary skill in the art.

Figure 32A:
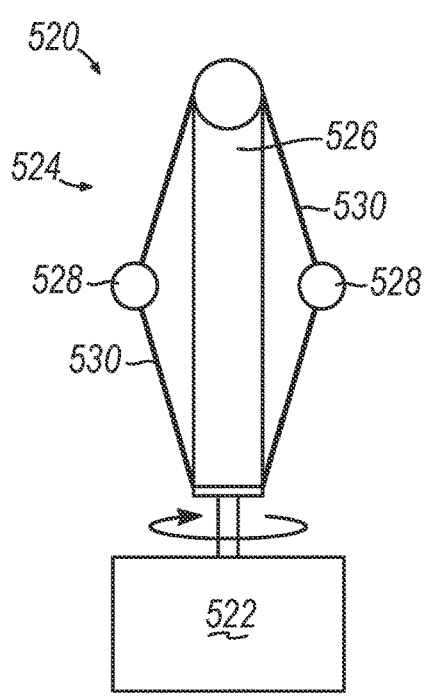
FIG. 32A depicts a perspective side view of a portion of an exemplary gyroscope assembly having a rotor with a selectively adjustable radius and resulting moment of inertia, showing the rotor with an exemplary small radius defining a low inertia state.
Figure 32B:
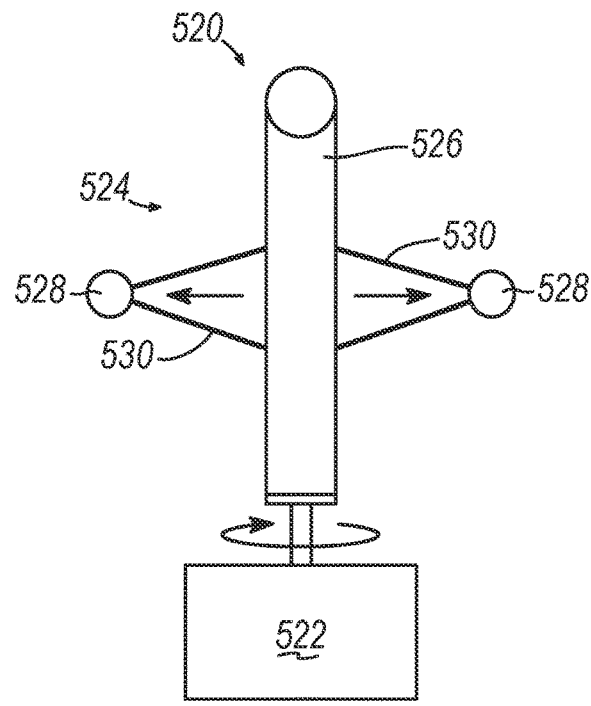
FIG. 32B depicts a perspective view of the portion of the gyroscope assembly of FIG. 32A, showing the rotor with an exemplary large radius defining a high inertia state.

FIGS. 32A and 32B schematically show a portion of an exemplary alternative gyroscope assembly (520) having an adjustable moment of inertia, and which is configured for use with any of the exemplary gyroscopic stabilizers described herein. Gyroscope assembly (520) includes a motor (522) and a rotor assembly (524) coupled with motor (522). Rotor assembly (524) includes a central shaft (526) and a pair of mass elements (528) coupled with first and second ends of central shaft (526) by a respective pair of tethers (530), which may be rigid or flexible and permit each mass element (528) to move radially relative to central shaft (526) between an inward position (FIG. 32A) and an outward position (FIG. 32B).

FIG. 32A shows gyroscope assembly (520) in a startup stage in which mass elements (528) are in the radially inward position. Rotation of rotor assembly (524) by motor (522) generates an angular momentum that is a function of the moment of inertia of mass elements (528). As described in detail above, this moment of inertia of mass elements (528) is determined by their combined mass, which is a fixed, and their effective radius relative to the spin axis defined central shaft (526), which is adjustable. Accordingly, in the radially inward position of FIG. 32A, mass elements (528) generate a relatively low amount of rotational inertia such that motor (522) must rotate rotor assembly (524) at a relatively high angular velocity in order for rotor assembly (524) to generate a sufficient magnitude of gyroscopic torque.

FIG. 32B shows gyroscope assembly (520) in a run stage in which mass elements (528) have been actuated by tethers (530) to their radially outward positions, thus increasing their effective radius relative to the spin axis defined by central shaft (526). Mass elements (528) thus generate a larger moment of inertia, and thus a resulting larger angular momentum and gyroscopic torque if the angular velocity of motor (522) is maintained from the startup stage of FIG. 32A. As a result, the angular velocity of motor (522) in the run stage may then be decreased while still maintaining the same angular momentum and gyroscopic torque output as in the startup stage of FIG. 32A, by virtue of the larger effective radius defined by mass elements (528) in the outward positions. Since motor (522) need only maintain the higher angular velocity temporarily during the startup stage, the size of motor (522) may be kept relatively small, thus providing gyroscope assembly (520) with an advantageously compact configuration and avoiding the need for a large motor while still achieving fast spin up times.

Figure 33:
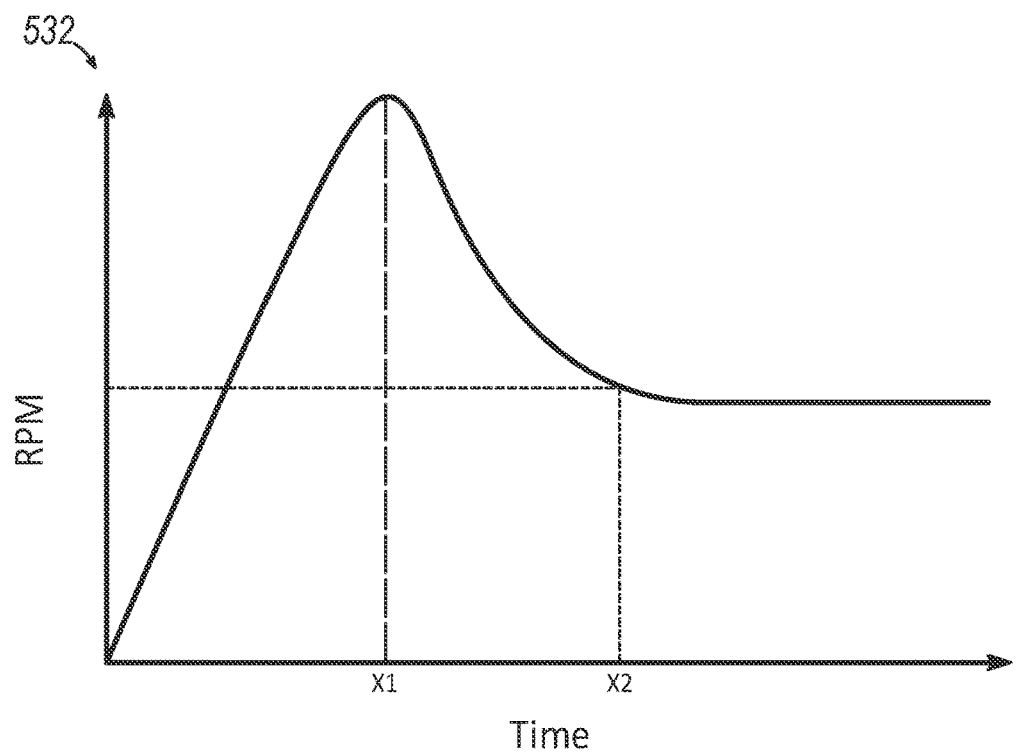
FIG. 33 depicts a line graph showing an exemplary progression of rotational speed of the rotor of FIG. 32A as the rotor transitions between the low inertia state of FIG. 32A and the high inertia state of FIG. 32B.

FIG. 33 shows an exemplary graph (532) illustrating the angular velocity of motor (522), in revolutions per minute (RPMs), as gyroscope assembly (520) transitions from the startup stage of FIG. 32A to the run stage of FIG. 32B. Point (X1) indicates the time at which a maximum angular velocity is achieved during the startup stage. This triggers gyroscope assembly (520) to transition to the run stage in which the angular velocity is decreased and reaches a plateau starting at point (X2), while still maintaining the same angular momentum and gyroscopic torque output as at point (X1).

Figure 34:
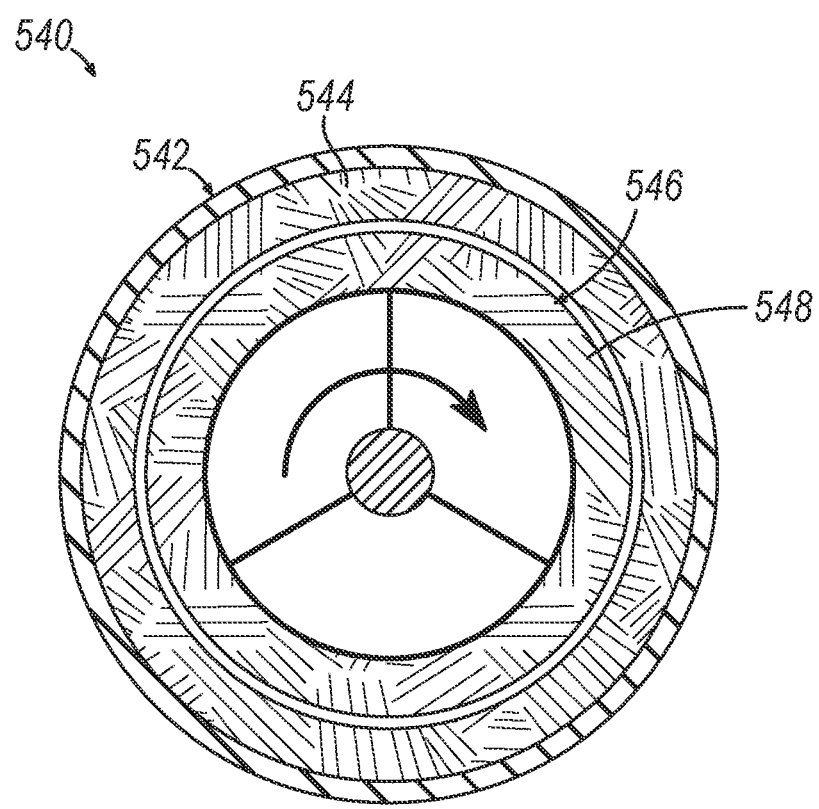
FIG. 34 depicts a schematic sectional view of a portion of another exemplary gyroscope assembly having an electric motor with an inner stator and an outer rotor that functions as a gyroscope rotor.

FIG. 34 shows another exemplary gyroscope assembly (540) having features that promote a compact configuration, and which may be used in place of gyroscope assemblies (240, 242) described above. Gyroscope assembly (540) is shown in the form of an electric motor having an outer stator (542) shaped as a spherical shell and including stator wire windings (544). Outer stator (542) may be configured to pivotably couple with stabilizer frame (212) in a manner similar to gyroscope assemblies (240, 242) described above. Gyroscope assembly (540) further includes an inner rotor (546) enclosed within outer stator (542) and having rotor wire windings (548). Inner rotor (546) is rotatably coupled with outer stator (542) about a spin axis (SA) and is configured to rotate relative to outer stator (542) in response to gyroscope assembly (540) being powered by a power source (not shown). Rotation of inner rotor (546) within outer stator (542) generates angular momentum and resulting gyroscopic torque.

E. Exemplary Gyroscope Assemblies Having Sterilizable and Hermetically Sealable Outer Shells In some instances, it may be desirable to removably house all of, or one or more portions of, gyroscopic stabilizer (210) within an outer shroud (also referred to as a shell) that may be sterilized to promote safe operating conditions for a patient. FIGS. 35-39 show various exemplary such configurations, each of which may have two or more separable shroud portions and a hermetic seal therebetween. It will be appreciated that any of these exemplary configurations may be implemented in connection with any of the exemplary gyroscopic stabilizers disclosed herein.

Figure 35:
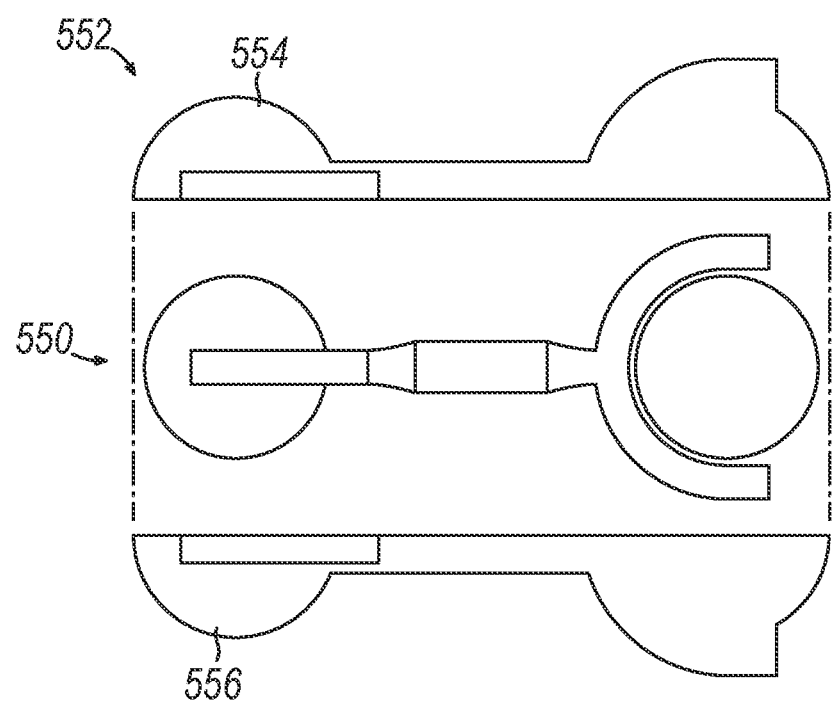
FIG. 35 depicts a schematic side elevational view of an exemplary gyroscopic stabilizer having a sterilizable outer shroud with first and second shroud halves that mate together with a hermetic seal to fully encapsulate a frame and first and second gyroscope assemblies of the stabilizer, showing the first and second shroud halves separated from one another.

FIG. 35 schematically shows an exemplary gyroscopic stabilizer (550), which may be similar to gyroscopic stabilizer (212) described above, in combination with a sterilizable outer shroud (552). Outer shroud (552) includes an upper shroud half (554) and a lower shroud half (556) that are configured to mate together to thereby encapsulate gyroscopic stabilizer (550) and form a hermetic seal between the mating portions of shroud halves (554, 556). Though not shown, each shroud half (554, 556) may each include a central opening configured to align with a central axis of gyroscopic stabilizer (550) to permit passage of a shaft portion of a surgical instrument therethrough.

Figure 36:
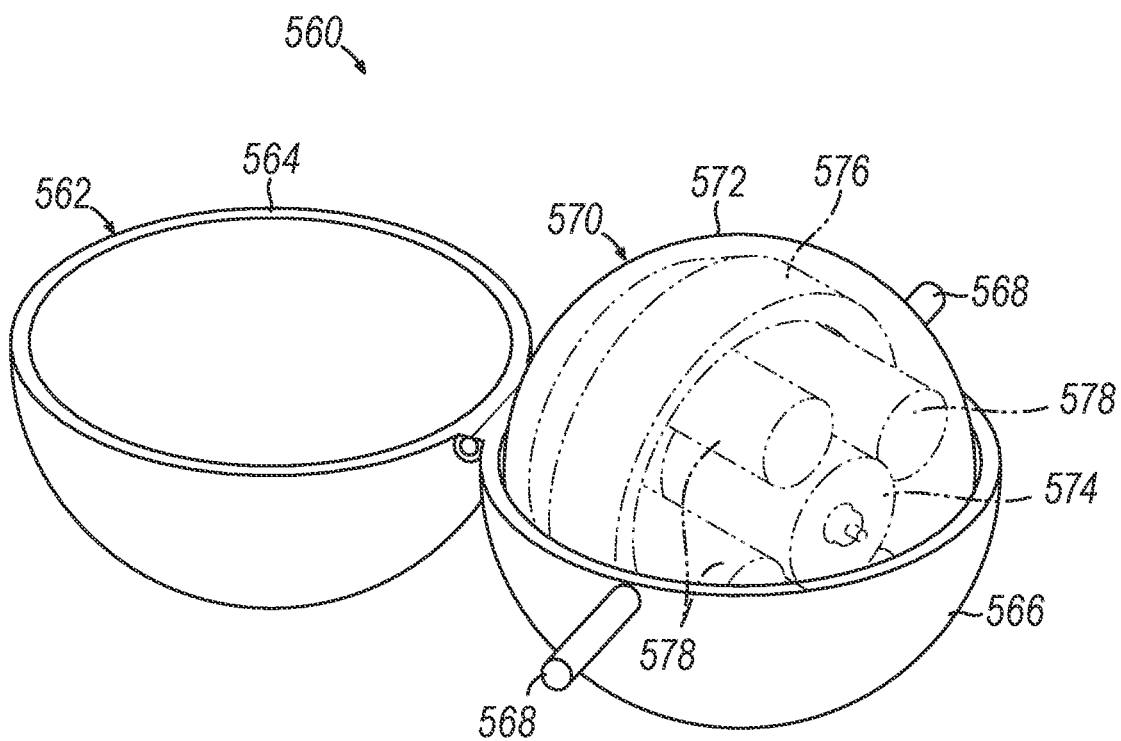
FIG. 36 depicts a schematic perspective view of an exemplary gyroscope assembly having components housed within a sterilizable and hermetically sealable outer shroud, showing a rotor, motor, and batteries of the gyroscope assembly in phantom.

FIG. 36 shows an exemplary gyroscope assembly (560) having a sterilizable outer shroud (562) and an orb assembly (570) configured to be fully encapsulated within clamshell outer shroud (562). Outer shroud (562) is configured as a clamshell having a first shroud half (564) and a second shroud half (566) hingedly coupled together, and a pair of pivot posts (568) configured to pivotably couple with a ring member (230, 232) of gyroscopic stabilizer frame (212). In that regard, clamshell outer shroud (562) is configured to function similar to gimbal (244) of gyroscope assemblies (240, 242).

Orb assembly (570) includes an outer structure (572), a motor (574) mounted to outer structure (572), a rotor (576) rotatably coupled with motor (574) and rotatably supported by outer structure (572), and a plurality of batteries (578). Each of these components may be similar to the corresponding components of gyroscope assemblies (240, 242) described above. Outer structure (572) is configured to seat within and remain stationary relative to outer shroud (562). In that regard, though not shown, one or more coupling features may be provided to fix outer structure (572) relative outer shroud (562) so that precession forces generated by rotor (576) are imparted to outer shroud (562), such that orb assembly (570) in its entirety may precess relative to gyroscopic stabilizer frame (212). Outer structure (572) may have a generally spherical shape as shown, or a variety of other suitable shapes that will be readily apparent to those of ordinary skill in the art. Outer shroud (562) may be sterilized and form a hermetic seal between its first and second shroud halves (564, 566). Between surgical procedures, outer shroud (562) may be replaced with another fresh, sterilized outer shroud (562), and orb assembly (570) may be reused.

Figure 37:
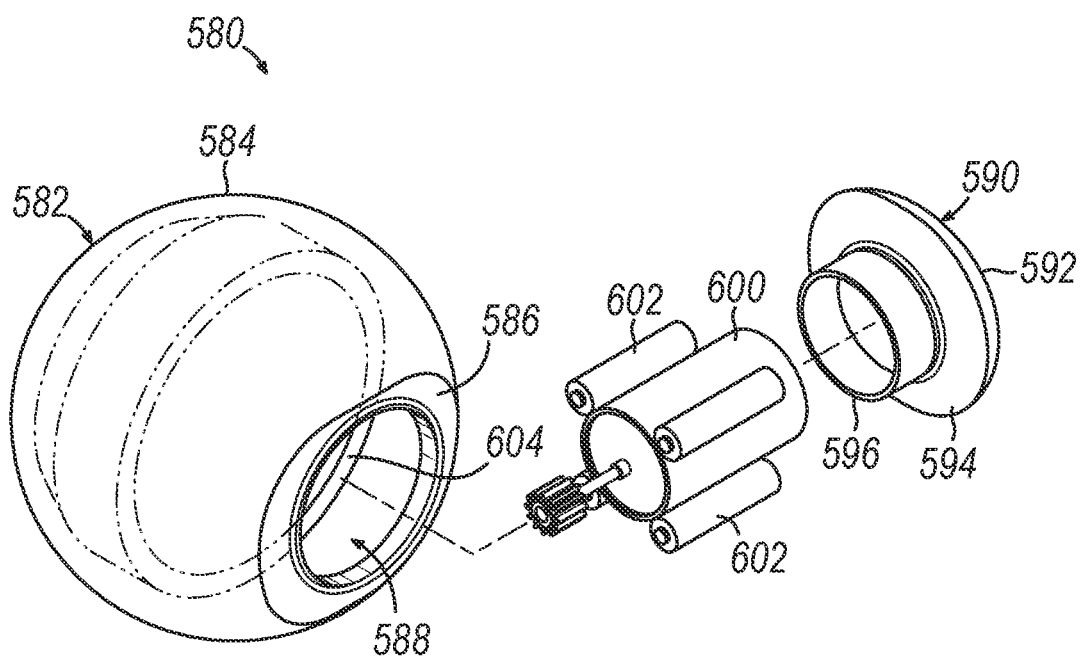
FIG. 37 depicts a schematic perspective view of an exemplary gyroscope assembly having a sterilizable and hermetically sealable outer shroud having first and second shroud portions, showing a rotor of the gyroscope assembly in phantom.

FIG. 37 shows another exemplary gyroscope assembly (580) having a sterilizable outer shroud (582) and gyroscope assembly components housed therein. Outer shroud (582) of the present version has a spherical main body portion (584) that includes a flat side face (586) and an opening (588) formed in the flat side face (586). Outer shroud (582) further includes a cap portion (590) having a spherical face (592), a flat face (594), and a collar (596) projecting outwardly from flat face (594). Collar (596) is configured to support a motor (600) and batteries (602), which may be similar to motor (246) and batteries (248) described above. A rotor (604) is rotatably housed within spherical main body portion (584) and is configured to couple with motor (600) through opening (588) when cap portion (590) is mated with spherical main body portion (584). By way of example only, rotor (604) may be similar to rotor (250) and may be configured to couple with motor (600) in manners similar to those described above in connection with FIGS. 10-12. Cap portion (590) may be separated from main body portion (584) between surgical procedures to recharge batteries (602).

Flat side face (586) of spherical main body portion (584) is configured to mate with flat face (594) of cap portion (590) to form a hermetic seal. Though not shown, outer shroud (582) may further include a pair of outwardly projecting pivot posts similar to pivot posts (568) of outer shroud (562), for pivotably coupling with gyroscopic stabilizer frame (212). Alternatively, outer shroud (582) may be seated within another structure configured to pivotably couple with gyroscopic stabilizer frame (212), such as outer shroud (562), for example.

Figure 38:
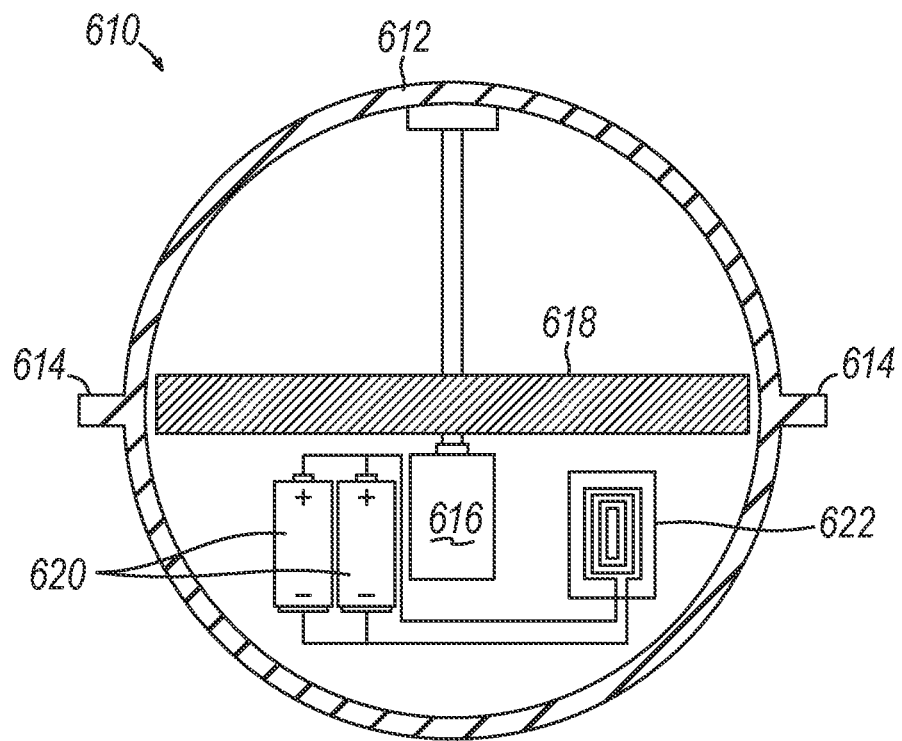
FIG. 38 depicts a schematic sectional view of another exemplary gyroscope assembly having a sterilizable and hermetically sealed outer shroud.

FIG. 38 shows yet another exemplary gyroscope assembly (610) having a sterilizable outer shroud (612) that houses internal gyroscope components, including a motor (616), a rotor (618), and a plurality of rechargeable batteries (620), each of which may be similar to the corresponding component of gyroscope assemblies (240, 242). Gyroscope assembly (610) further includes an induction charging circuit (622) electrically coupled with batteries (620) within outer shroud (612). Outer shroud (612) includes a pair of pivot posts (614) configured to pivotably couple with gyroscopic stabilizer frame (212), as shown schematically in FIG. 39. Additionally, outer shroud (612) may be formed as a unitary structure as shown, or alternatively of two or more separable portions that hermetically seal with one another.

Figure 39:
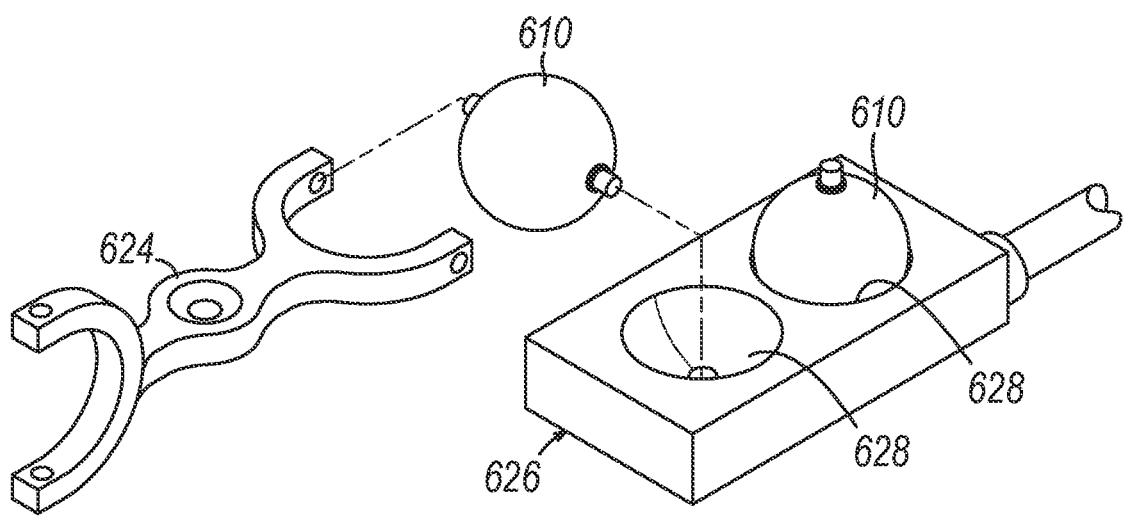
FIG. 39 depicts a schematic perspective view of two gyroscope assemblies according to the configuration of FIG. 38, showing the gyroscope assemblies separated from a gyroscopic stabilizer frame and being seated within respective charging ports of an electrical charging device.

Induction charging circuit (622) housed without outer shroud (612) enables recharging of batteries (620) without removing batteries (620) from outer shroud (612) or otherwise disassembling outer shroud (612) to access batteries (620), for example as shown in FIG. 39. More specifically, FIG. 39 shows gyroscope assemblies (610) separated from an exemplary gyroscopic stabilizer frame (624) and being seated within respective charging ports (628) of an exemplary induction charging device (626) for recharging batteries (620). Charging device (626) may be configured in various other manners that will be readily apparent to those of ordinary skill in the art in view of the teachings herein.

F. Exemplary Gyroscopic Stabilizer with Plurality of Gyroscope Assemblies

The exemplary gyroscope stabilizers shown and described above in connection with FIGS. 6-39 include only first and second gyroscope assemblies, which are diametrically opposed from one another. However, it will be appreciated that in other versions any of the gyroscopic stabilizers may be provided with three or more gyroscope assemblies, arranged circumferentially about the corresponding stabilizer hub with uniform circumferential spacing. In such configurations, each gyroscope assembly may be relatively smaller in size.

Figure 40:
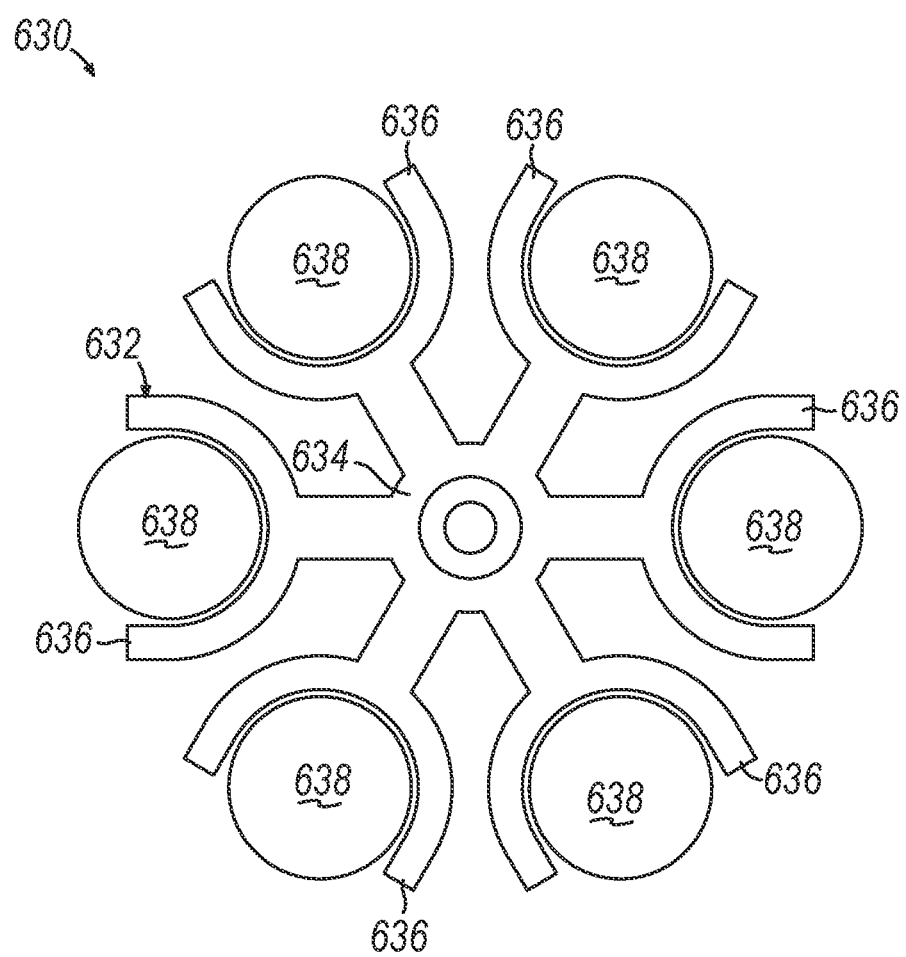
FIG. 40 depicts a schematic perspective view of an exemplary gyroscopic stabilizer having more than two gyroscope assemblies.

For instance, FIG. 40 shows an exemplary gyroscopic stabilizer (630) having a frame (632) with a central hub (634) and six gyroscope support members (636) arranged circumferentially about hub (634) with uniform circumferential spacing. Each gyroscope support member (636) pivotably supports a respective gyroscope assembly (638), which may be similar to any of the exemplary gyroscope assemblies described above. In some versions, one or more of gyroscope assemblies (638) may be equipped with an active precession control mechanism, for example similar to motorized belt drive mechanism (450) of FIG. 26 described above. In some such versions, a first group of gyroscope assemblies (638) may include such an active precession control mechanism, and a second group of gyroscope assemblies (638) omit active precession control so as to exit "passive" precession in which such gyroscope assemblies (638) are configured to process freely at a natural precession rate.

III. Exemplary Combinations

The following examples relate to various non-exhaustive ways in which the teachings herein may be combined or applied. It should be understood that the following examples are not intended to restrict the coverage of any claims that may be presented at any time in this application or in subsequent filings of this application. No disclaimer is intended. The following examples are being provided for nothing more than merely illustrative purposes. It is contemplated that the various teachings herein may be arranged and applied in numerous other ways. It is also contemplated that some variations may omit certain features referred to in the below examples. Therefore, none of the aspects or features referred to below should be deemed critical unless otherwise explicitly indicated as such at a later date by the inventors or by a successor in interest to the inventors. If any claims are presented in this application or in subsequent filings related to this application that include additional features beyond those referred to below, those additional features shall not be presumed to have been added for any reason relating to patentability.

Example 1

A gyroscope stabilizer configured to stabilize a surgical instrument relative to a patient, comprising: (a) a frame, wherein the frame includes a hub that extends about a central axis and is configured to releasably couple with a surgical instrument such that the gyroscopic stabilizer is configured to be supported by the surgical instrument above a patient; (b) a first gyroscope assembly coupled with a first frame portion of the frame, wherein the first gyroscope assembly includes: (i) a first gimbal pivotably coupled with the first frame portion about a first precession axis, (ii) a first motor, and (iii) a first rotor rotatably coupled with the first motor about a first spin axis perpendicular to the first precession axis; and (c) a second gyroscope assembly coupled with a second frame portion of the frame, wherein the second gyroscope assembly includes: (i) a second gimbal pivotably coupled with the second frame portion about a second precession axis, (ii) a second motor, and (iii) a second rotor rotatably coupled with the second motor about a second spin axis perpendicular to the second precession axis, wherein the first gyroscope assembly is operable to rotate the first rotor with the first motor about the first spin axis to generate a first torque in a first torque plane that contains the first spin axis and the first precession axis, wherein the first torque is configured to resist rotation of the gyroscopic stabilizer relative to the patient about a first device axis perpendicular to the central axis, wherein the second gyroscope assembly is operable to rotate the second rotor with the second motor about the second spin axis to generate a second torque in a second torque plane that contains the second spin axis and the second precession axis, wherein the second torque is configured to resist rotation of the gyroscopic stabilizer relative to the patient about a second device axis perpendicular to the central axis and the first device axis.

Example 2

The gyroscope stabilizer of Example 1, herein the first gyroscope assembly is disposed on a first side of the central axis, wherein the second gyroscope assembly is disposed on a second side of the central axis.

Example 3

The gyroscope stabilizer of Example 2, wherein the first and second gyroscope assemblies are spaced equidistantly apart from each other about the central axis.

Example 4

The gyroscope stabilizer of any of the preceding Examples, wherein the first and second precession axes are angled relative to one another.

Example 5

The gyroscope stabilizer of Example 4, wherein the first and second precession axes are angled relative to one another by 90 degrees.

Example 6

The gyroscope stabilizer of any of the preceding Examples, wherein the first frame portion comprises a first ring member defining a first enclosed space, wherein the second frame portion comprises a second ring member defining a second enclosed space, wherein the first gimbal is pivotably coupled with the first ring member and is pivotable about the first precession axis within the first enclosed space, wherein the second gimbal is pivotably coupled with the second ring member and is pivotable about the second precession axis within the second enclosed space.

Example 7

The gyroscope stabilizer of any of the preceding Examples, wherein the first motor is supported by the first gimbal, wherein the second motor is supported by the second gimbal.

Example 8

The gyroscope stabilizer of any of the preceding Examples, further comprising at least one battery supported by the frame, wherein the at least one battery is configured to power the first and second motors.

Example 9

The gyroscope stabilizer of any of the preceding Examples, wherein each of the first and second rotors includes an inner cavity, wherein each of the first and second motors is disposed at least partially within the inner cavity of the respective rotor such that each rotor is rotatable about the respective motor.

Example 10

The gyroscope stabilizer of Example 9, wherein each of the first and second gyroscope assemblies further includes a battery configured to power the respective motor, wherein each battery is disposed at least partially within the inner cavity of the respective rotor.

Example 11

The gyroscope stabilizer of any of the preceding Examples, wherein the surgical instrument comprises a surgical cannula, wherein the hub includes a central passage configured to slidably receive a shaft of a second surgical instrument therethrough along the central axis.

Example 12

A gyroscopic stabilization system comprising: (a) the gyroscopic stabilizer of any of the preceding Examples; and (b) a controller in communication with the gyroscopic stabilizer, wherein the controller is arranged separately from the gyroscopic stabilizer.

Example 13

The gyroscope stabilizer of Example 12, wherein the controller is configured to communicate with the processor wirelessly.

Example 14

The gyroscope stabilizer of any of Examples 12 through 13, wherein the controller is operable to control a rotational speed of at least one of the first motor or the second motor.

Example 15

The gyroscope stabilizer of any of Examples 12 through 14, wherein at least one of the first gyroscope assembly or the second gyroscope assembly includes a precession control mechanism controllable by the controller, wherein the precession control mechanism is operable to vary at least one of: (i) a rate of pivoting motion of the respective gimbal relative to the respective frame portion about the respective precession axis, or (ii) an angular orientation of the respective gimbal relative to the respective frame portion about the respective precession axis.

Example 16

A gyroscopic surgical instrument assembly comprising: (a) a surgical instrument; and (b) a gyroscopic stabilizer coupled with the surgical instrument, wherein the gyroscopic stabilizer includes: (i) a frame, (ii) a gimbal pivotably coupled with the frame about a precession axis, (iii) a motor, and (iv) a rotor rotatably coupled with the motor about a spin axis perpendicular to the precession axis, wherein the rotor is rotatable by the motor about the spin axis to generate a stabilization torque in a torque plane that contains the spin axis and the precession axis, wherein the gyroscopic stabilizer is operable to generate stabilization torque in the torque plane sufficient to counteract an external torque due to gravity exerted on the surgical instrument and thereby maintain a selected angular orientation of the surgical instrument relative to a patient.

Example 17

The gyroscopic surgical instrument assembly of Example 16, wherein the surgical instrument includes an elongate portion defining a longitudinal axis, wherein gyroscopic stabilizer is coupled with the surgical instrument such that a central axis of the gyroscopic stabilizer is aligned coaxially with the longitudinal axis.

Example 18

A method of stabilizing a surgical instrument with a gyroscopic stabilizer that includes a frame, a gimbal pivotably coupled with the frame about a precession axis, and a rotor rotatable relative to the gimbal about a spin axis perpendicular to the precession axis, the method comprising: (a) engaging a portion of the surgical instrument with the gyroscopic stabilizer to inhibit relative movement therebetween; (b) rotating the rotor about the spin axis and thereby generating a stabilization torque in a torque plane that contains the spin axis and the precession axis; and (c) via the stabilization torque, counteracting an external torque due to gravity exerted on the surgical instrument and thereby maintaining a selected angular orientation of the surgical instrument relative to a patient.

Example 19

The method of Example 18, wherein the gyroscopic stabilizer further includes a motor, wherein rotating the rotor about the spin axis includes rotating the rotor with the motor.

Example 20

The method of any of Examples 18 through 19, further comprising adjusting the stabilization torque by selectively varying at least one of (i) a rotational speed of the rotor about the spin axis, (ii) a rate of pivoting motion of the gimbal relative to the frame about the precession axis, or (iii) an angular orientation of the gimbal relative to the frame about the precession axis.

IV. Miscellaneous

It should be understood that any one or more of the teachings, expressions, embodiments, examples, etc. described herein may be combined with any one or more of the other teachings, expressions, embodiments, examples, etc. that are described herein. The above-described teachings, expressions, embodiments, examples, etc. should therefore not be viewed in isolation relative to each other. Various suitable ways in which the teachings herein may be combined will be readily apparent to those of ordinary skill in the art in view of the teachings herein. Such modifications and variations are intended to be included within the scope of the claims.

Furthermore, any one or more of the teachings herein may be combined with any one or more of the teachings disclosed in U.S. patent application Ser. No. 17/213,302, entitled "Pinch-To-Release Cannula Depth Limiter," filed on Mar. 26, 2021, issued as U.S. Pat. No. 11,633,211 on Apr. 25, 2023; U.S. patent application Ser. No. 17/213,304, entitled "Multi-Diameter Cannula Depth Limiter," filed on Mar. 26, 2021, published as U.S. Pub. No. 2021/0338273 on Nov. 4, 2021; U.S. patent application Ser. No. 17/213,401, entitled "Pinch-To-Clamp Cannula Depth Limiter," filed on Mar. 26, 2021, published as U.S. Pub. No. 2021/033273 on Nov. 4, 2021; U.S. patent application Ser. No. 17/213,409, entitled "Universal Size Multi-Walled Elastomer Cannula Depth Limiter," filed on Mar. 26, 2021, published as U.S. Pub. No. 2021/0338282 on Nov. 4, 2021; U.S. patent application Ser. No. 17/213,415, entitled "Threaded Cannula Depth Limiter," filed on Mar. 26, 2021, published as U.S. Pub. No. 2021/0338274 on Nov. 4, 2021; U.S. patent application Ser. No. 17/213,426, entitled "Tilting Tang Cannula Depth Limiter," filed on Mar. 26, 2021, issued as U.S. Pat. No. 11,712,267 on Aug. 1, 2023; U.S. patent application Ser. No. 17/213,431, entitled "Two Piece Separable Obturator," filed on Mar. 26, 2021, published as U.S. Pub. No. 2021/0338275 on Nov. 4, 2021; U.S. patent application Ser. No. 17/213, 431, entitled "Latchless Obturator with Interference Fit Feature," filed on Mar. 26, 2021, published as U.S. Pub. No. 2021/0338269 on Nov. 4, 2021; U.S. patent application Ser. No. 17/213,437, entitled "Balancing Feature for Reusable Trocar," filed on Mar. 26, 2021 issued as U.S. Pat. No. 11 559,329 on Jan. 24, 2023; and/or U.S. patent application Ser. No. 17/213,508, entitled "Airflow Channels and Patterns in Lumen for Cannula," filed on Mar. 26, 2021, published as U.S. Pub. No. 2021/0338278 on Nov. 4, 2021. The disclosure of each of these patent applications is incorporated by reference herein.

It should be appreciated that any patent, publication, or other disclosure material, in whole or in part, that is said to be incorporated by reference herein is incorporated herein only to the extent that the incorporated material does not conflict with existing definitions, statements, or other disclosure material set forth in this disclosure. As such, and to the extent necessary, the disclosure as explicitly set forth herein supersedes any conflicting material incorporated herein by reference. Any material, or portion thereof, that is said to be incorporated by reference herein, but which conflicts with existing definitions, statements, or other disclosure material set forth herein will only be incorporated to the extent that no conflict arises between that incorporated material and the existing disclosure material.

Versions of the devices described above may have application in conventional medical treatments and procedures conducted by a medical professional, as well as application in robotic-assisted medical treatments and procedures. By way of example only, various teachings herein may be readily incorporated into a robotic surgical system such as the DAVINCI™ system by Intuitive Surgical, Inc., of Sunnyvale, California. Similarly, those of ordinary skill in the art will recognize that various teachings herein may be readily combined with various teachings of any of the following: U.S. Pat. No. 5,792,135, entitled "Articulated Surgical Instrument For Performing Minimally Invasive Surgery With Enhanced Dexterity and Sensitivity," issued Aug. 11, 1998, the disclosure of which is incorporated by reference herein; U.S. Pat. No. 8,783,541, entitled "Robotically-Controlled Surgical End Effector System," issued Jul. 22, 2014, the disclosure of which is incorporated by reference herein; U.S. Pat. No. 8,479,969, entitled "Drive Interface for Operably Coupling a Manipulatable Surgical Tool to a Robot," issued Jul. 9, 2013; U.S. Pat. No. 8,800,838, entitled "Robotically-Controlled Cable-Based Surgical End Effectors," issued Aug. 12, 2014, the disclosure of which is incorporated by reference herein; and/or U.S. Pat. No. 8,573,465, entitled "Robotically-Controlled Surgical End Effector System with Rotary Actuated Closure Systems," issued Nov. 5, 2013, the disclosure of which is incorporated by reference herein.

Versions of the devices described above may be designed to be disposed of after a single use, or they can be designed to be used multiple times. Versions may, in either or both cases, be reconditioned for reuse after at least one use. Reconditioning may include any combination of the steps of disassembly of the device, followed by cleaning or replacement of particular pieces, and subsequent reassembly. In particular, some versions of the device may be disassembled, and any number of the particular pieces or parts of the device may be selectively replaced or removed in any combination. Upon cleaning and/or replacement of particular parts, some versions of the device may be reassembled for subsequent use either at a reconditioning facility, or by a user immediately prior to a procedure. Those skilled in the art will appreciate that reconditioning of a device may utilize a variety of techniques for disassembly, cleaning/replacement, and reassembly. Use of such techniques, and the resulting reconditioned device, are all within the scope of the present application.

By way of example only, versions described herein may be sterilized before and/or after a procedure. In one sterilization technique, the device is placed in a closed and sealed container, such as a plastic or TYVEK bag. The container and device may then be placed in a field of radiation that can penetrate the container, such as gamma radiation, x-rays, or high-energy electrons. The radiation may kill bacteria on the device and in the container. The sterilized device may then be stored in the sterile container for later use. A device may also be sterilized using any other technique known in the art, including but not limited to beta or gamma radiation, ethylene oxide, or steam.

Having shown and described various embodiments of the present invention, further adaptations of the methods and systems described herein may be accomplished by appropriate modifications by one of ordinary skill in the art without departing from the scope of the present invention. Several of such potential modifications have been mentioned, and others will be apparent to those skilled in the art.

For instance, the examples, embodiments, geometries, materials, dimensions, ratios, steps, and the like discussed above are illustrative and are not required. Accordingly, the scope of the present invention should be considered in terms of the following claims and is understood not to be limited to the details of structure and operation shown and described in the specification and drawings.

We claim:

1. A gyroscopic stabilizer configured to stabilize a surgical instrument relative to a patient, comprising:
   (a) a frame, wherein the frame includes a hub that extends about a central axis and is configured to releasably couple with a surgical instrument such that the gyroscopic stabilizer is configured to be supported by the surgical instrument above a patient;
   (b) a first gyroscope assembly coupled with a first frame portion of the frame, wherein the first gyroscope assembly includes:
      (i) a first gimbal pivotably coupled with the first frame portion about a first precession axis,
      (ii) a first motor, and
      (iii) a first rotor rotatably coupled with the first motor about a first spin axis perpendicular to the first precession axis; and
   (c) a second gyroscope assembly coupled with a second frame portion of the frame, wherein the second gyroscope assembly includes:
      (i) a second gimbal pivotably coupled with the second frame portion about a second precession axis,
      (ii) a second motor, and
      (iii) a second rotor rotatably coupled with the second motor about a second spin axis perpendicular to the second precession axis,
   wherein the first gyroscope assembly is operable to rotate the first rotor with the first motor about the first spin axis to generate a first torque in a first torque plane that contains the first spin axis and the first precession axis, wherein the first torque is configured to resist rotation of the gyroscopic stabilizer relative to the patient about a first device axis perpendicular to the central axis,
   wherein the second gyroscope assembly is operable to rotate the second rotor with the second motor about the second spin axis to generate a second torque in a second torque plane that contains the second spin axis and the second precession axis, wherein the second torque is configured to resist rotation of the gyroscopic stabilizer relative to the patient about a second device axis perpendicular to the central axis and the first device axis.

2. The gyroscopic stabilizer of claim 1, wherein the first gyroscope assembly is disposed on a first side of the central axis, wherein the second gyroscope assembly is disposed on a second side of the central axis.

3. The gyroscopic stabilizer of claim 2, wherein the first and second gyroscope assemblies are spaced equidistantly apart from each other about the central axis.

4. The gyroscopic stabilizer of claim 1, wherein the first and second precession axes are angled relative to one another.

5. The gyroscopic stabilizer of claim 4, wherein the first and second precession axes are angled relative to one another by 90 degrees.

6. The gyroscopic stabilizer of claim 1, wherein the first frame portion comprises a first ring member defining a first enclosed space, wherein the second frame portion comprises a second ring member defining a second enclosed space, wherein the first gimbal is pivotably coupled with the first ring member and is pivotable about the first precession axis within the first enclosed space, wherein the second gimbal is pivotably coupled with the second ring member and is pivotable about the second precession axis within the second enclosed space.

7. The gyroscopic stabilizer of claim 1, wherein the first motor is supported by the first gimbal, wherein the second motor is supported by the second gimbal.

8. The gyroscopic stabilizer of claim 1, further comprising at least one battery supported by the frame, wherein the at least one battery is configured to power the first and second motors.

9. The gyroscopic stabilizer of claim 1, wherein each of the first and second rotors includes an inner cavity, wherein each of the first and second motors is disposed at least partially within the inner cavity of the respective rotor such that each rotor is rotatable about the respective motor.

10. The gyroscopic stabilizer of claim 9, wherein each of the first and second gyroscope assemblies further includes a battery configured to power the respective motor, wherein each battery is disposed at least partially within the inner cavity of the respective rotor.

11. The gyroscopic stabilizer of claim 1, wherein the surgical instrument comprises a surgical cannula, wherein the hub includes a central passage configured to slidably receive a shaft of a second surgical instrument therethrough along the central axis.

12. A gyroscopic stabilization system comprising:
   (a) the gyroscopic stabilizer of claim 1; and
   (b) a controller in communication with the gyroscopic stabilizer, wherein the controller is arranged separately from the gyroscopic stabilizer.

13. The gyroscopic stabilization system of claim 12, wherein the controller is configured to communicate with the processor wirelessly.

14. The gyroscopic stabilization system of claim 12, wherein the controller is operable to control a rotational speed of at least one of the first motor or the second motor.

15. The gyroscopic stabilization system of claim 12, wherein at least one of the first gyroscope assembly or the second gyroscope assembly includes a precession control mechanism controllable by the controller, wherein the precession control mechanism is operable to vary at least one of:
   (i) a rate of pivoting motion of the respective gimbal relative to the respective frame portion about the respective precession axis, or
   (ii) an angular orientation of the respective gimbal relative to the respective frame portion about the respective precession axis.

16. A gyroscopic surgical instrument assembly comprising:
   (a) a surgical instrument; and
   (b) a gyroscopic stabilizer coupled with the surgical instrument, wherein the gyroscopic stabilizer includes:
      (i) a frame,
      (ii) a gimbal pivotably coupled with the frame about a precession axis,
      (iii) a motor, and
      (iv) a rotor rotatably coupled with the motor about a spin axis perpendicular to the precession axis,
      wherein the rotor is rotatable by the motor about the spin axis to generate a stabilization torque in a torque plane that contains the spin axis and the precession axis,
      wherein the gyroscopic stabilizer is operable to generate stabilization torque in the torque plane sufficient to counteract an external torque due to gravity exerted on the surgical instrument and thereby maintain a selected angular orientation of the surgical instrument relative to a patient.

17. The gyroscopic surgical instrument assembly of claim 16, wherein the surgical instrument includes an elongate portion defining a longitudinal axis, wherein gyroscopic stabilizer is coupled with the surgical instrument such that a central axis of the gyroscopic stabilizer is aligned coaxially with the longitudinal axis.

18. A method of stabilizing a surgical instrument with a gyroscopic stabilizer that includes a frame, a gimbal pivotably coupled with the frame about a precession axis, and a rotor rotatable relative to the gimbal about a spin axis perpendicular to the precession axis, the method comprising:
(a) engaging a portion of the surgical instrument with the gyroscopic stabilizer to inhibit relative movement therebetween;
(b) rotating the rotor about the spin axis and thereby generating a stabilization torque in a torque plane that contains the spin axis and the precession axis; and
(c) via the stabilization torque, counteracting an external torque due to gravity exerted on the surgical instrument and thereby maintaining a selected angular orientation of the surgical instrument relative to a patient.

19. The method of claim 18, wherein the gyroscopic stabilizer further includes a motor, wherein rotating the rotor about the spin axis includes rotating the rotor with the motor.

20. The method of claim 18, further comprising adjusting the stabilization torque by selectively varying at least one of:
(i) a rotational speed of the rotor about the spin axis,
(ii) a rate of pivoting motion of the gimbal relative to the frame about the precession axis, or
(iii) an angular orientation of the gimbal relative to the frame about the precession axis.

* * * * *